(12) United States Patent
Gogotsi et al.

(10) Patent No.: US 11,918,723 B2
(45) Date of Patent: Mar. 5, 2024

(54) METHODS OF USING GRAPHINE NANOPLATELETS OR POLYMER-DERIVED CERAMIC CARBIDE-DERIVED CARBON TO REMOVE PROTEINS FROM BLOOD AND TO TREAT SEPSIS

(71) Applicant: Drexel University, Philadelphia, PA (US)

(72) Inventors: Yury Gogotsi, Ivyland, PA (US); Vadym Mochalin, Rolla, MO (US); Nicholas Pescatore, Ambler, PA (US)

(73) Assignee: Drexel University, Philadelphia, PA (US)

( * ) Notice: Subject to any disclaimer, the term of this patent is extended or adjusted under 35 U.S.C. 154(b) by 55 days.

(21) Appl. No.: 17/402,856

(22) Filed: Aug. 16, 2021

(65) Prior Publication Data
US 2021/0379263 A1 Dec. 9, 2021

Related U.S. Application Data

(62) Division of application No. 16/303,687, filed as application No. PCT/US2017/034635 on May 26, 2017, now Pat. No. 11,123,465.

(60) Provisional application No. 62/353,078, filed on Jun. 22, 2016, provisional application No. 62/341,661, filed on May 26, 2016.

(51) Int. Cl.
*A61M 1/34* (2006.01)
*B01J 20/20* (2006.01)
*B01J 20/28* (2006.01)
*B01J 20/32* (2006.01)

(52) U.S. Cl.
CPC .......... *A61M 1/3486* (2014.02); *B01J 20/205* (2013.01); *B01J 20/28083* (2013.01); *B01J 20/28085* (2013.01); *B01J 20/321* (2013.01); *A61M 2202/0445* (2013.01); *A61M 2202/07* (2013.01)

(58) Field of Classification Search
CPC ........ A61M 1/3486; A61M 2202/0445; A61M 2202/07; B01J 20/205; B01J 20/28083; B01J 20/28085; B01J 20/321
See application file for complete search history.

(56) References Cited

U.S. PATENT DOCUMENTS

| | | |
|---|---|---|
| 2004/0228829 A1 | 11/2004 | Roberts et al. |
| 2009/0258782 A1 | 10/2009 | Gogotsi et al. |
| 2013/0072845 A1 | 3/2013 | Tennison et al. |

FOREIGN PATENT DOCUMENTS

| | | |
|---|---|---|
| CN | 103533830 A | 1/2014 |
| JP | 04-314456 A | 11/1992 |
| JP | 2009-518277 A | 5/2009 |
| JP | 2014-502971 A | 2/2014 |
| WO | 2007/070455 A2 | 6/2007 |

OTHER PUBLICATIONS

Gogotsi Y, et al. (Sep. 2003) Nature Materials. 2(9):591-594. (http://dx.doi.org/10.1038/nmat957).*
Presser V, et al. (2011) Adv Funct Mater. 21:810-833 (DOI: 10.1002/adfm.201002094).*
Yeon S-H, et al. (2010). Carbon. 48:201-210. (doi:10.1016/j.carbon.2009.09.004).*
https://us-nano.com/inc/sdetail/18480 (Graphene Nanoplatelets / Graphene NanoPowder (95+%, Thickness 2-8nm, 3-6 layers)).*
Xinjiao Zhang, "Molecular dynamics studies on the interaction between nanodroplets and alkane modified graphite surfaces", Chinese Doctoral Dissertation & Master's Theses Engineering Science and Technology I, Feb. 15, 2014, 2 Pages.
Brunauer et al., "Adsorption of Gases in Multimolecular Layers", Journal of the American Chemical Society, 1938, vol. 60, 309-319.
Chaudhry, H., et al. Role of Cytokines as a double-edged sword in sepsis. In Vivo, 27(6), pp. 669-684, 2013 (Year: 2013).
Dyatkin et al., "Effects of structural disorder and surface chemistry on electric conductivity and capacitance of porous carbon electrodes," Faraday Discussions, 2014, vol. 172, pp. 139-162.
Dyatkin et al., "Influence of Structure and Surface Chemistry of Porous Carbon Electrodes on Supercapacitor Performance", Drexel University, Dissertation/Thesis, 2016, 24 pages.
Gambro. Hemoperfusion—Renal intensive care self-learning module, Copyright Feb. 2009, 36 pages (Year: 2009).
Ho et al., "Pseudo-second order model for sorption processes", Process Biochemistry, 1999, vol. 34, 451-465.
Lastoskie et al., "Pore size heterogeneity and he carbon slit pore: a density functional theory model", Langmuir, 1993, vol. 9, 2693-2702.
Lee et al., "Sea-Urchin-Inspired 3D Crumpled Graphene Balls Using Simultaneous Etching and Reduction Process for High-Density Capacitive Energy Storage", Advanced Functional Materials, 2015, vol. 25, 3606-3614.
Lowell et al., "Figure 3.1 from Adsorption isotherms", Powder Surface Area and Porosity, 1991, 1 page.
Osswald et al., "Monitoring oxidation of multiwalled carbon nanotubes by Raman Spectroscopy", Journal of Raman Spectroscopy, 2007, vol. 38, 728-736.
Osswald et al., "Porosity control in nanoporous carbide-derived carbon by oxidation in air and carbon dioxide", Journal of Solid State Chemistry, 2009, vol. 182, 1733-1741.

(Continued)

*Primary Examiner* — Robert S Landsman
(74) *Attorney, Agent, or Firm* — BakerHostetler

(57) ABSTRACT

The present disclosure is directed to methods of removing proteins, including cytokines, from blood and blood products, the methods comprising contacting the blood or blood product with a form of carbon having high graphitic contents and slit-shaped mesopores and macropores, the pore size dimensions chosen to be comparable to the size of the proteins, wherein the contacting results in the removal of high levels of the protein from the blood or blood product in minutes or hours.

17 Claims, 56 Drawing Sheets

(56) References Cited

OTHER PUBLICATIONS

Portet et al., "Impact of synthesis conditions on surface chemistry and structure of carbide-derived carbons", Thermochimica Acta, 2010, 497, 137-142.
Walpole et al., "The weight of nations: an estimation of adult human biomass", BMC Public Health, 2012, vol. 12,439, 6 pages.
Wanci, S., et al. Expanded graphite—A new kind of biomedical material. Carbon, 37, pp. 351-358, 1999 (Year: 1999).
Xie et al., "MoS2 Nanosheets Vertically Aligned on Carbon Paper: A Freestanding Electrode for Highly Reversible Sodium-Ion Batteries", Advanced Energy Materials, 2016, vol. 6, 1502161, 7 pages.
Yachamaneni et al., "Mesoporous carbide-derived carbon for cytokine removal from blood plasma", Biomaterials, Jun. 2010, 31(18), 4789-4794.
Yakovlev et al., "Thermally Expanded Graphite: Synthesis, Properties, and Prospects for Use", Russian J. of Appl. Chem., 2006, 79(11).
Yushin et al., "Mesoporous carbide-derived carbon with porosity tuned for efficient adsorption of cytokines", Biomaterials, 2006, 27(34), 5755-5762.

\* cited by examiner

| Material – GNP C-500 | Weight % | | |
|---|---|---|---|
| | C | O | N |
| As-received | 95 | 5 | -- |
| Vacuum Annealed | 98 | 2 | -- |
| Vacuum Annealed (10 days later) | 98 | 2 | -- |
| ARC-500 Acid Oxidized | 89 | 11 | -- |
| ARC-500 Aminated | 90 | 8 | 2 |

| Material – GNP C-500 | Atomic % | | |
|---|---|---|---|
| | C 1s | O 1s | N 1s |
| ARC-500 | 94.04 | 5.96 | -- |
| Vacuum Annealed | 99.38 | 0.62 | -- |
| Vacuum Annealed, Acid Oxidized | 87.27 | 12.73 | -- |
| Vacuum Annealed, Air Oxidized, Aminated | 97.53 | 1.10 | 1.37 |

FIG 26A  FIG 26B
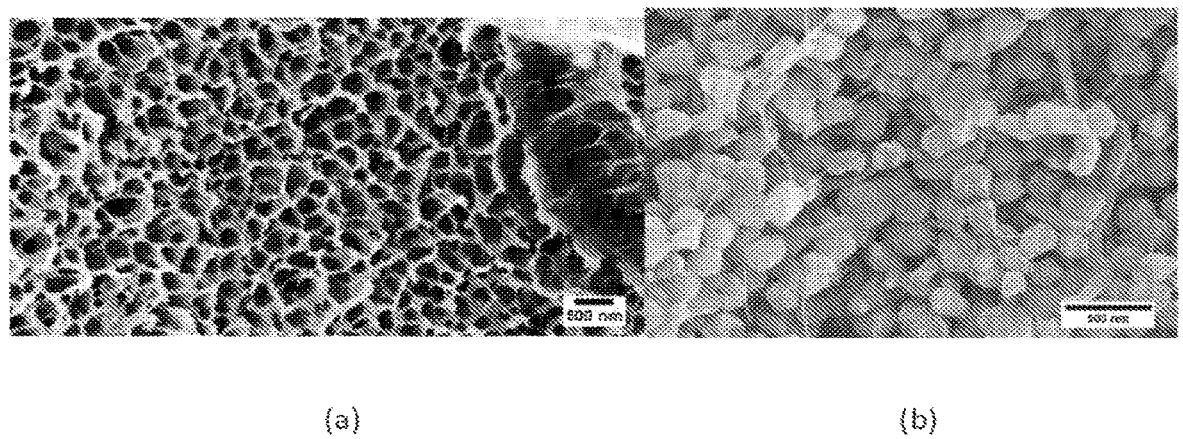
(a)  (b)
FIG 27A
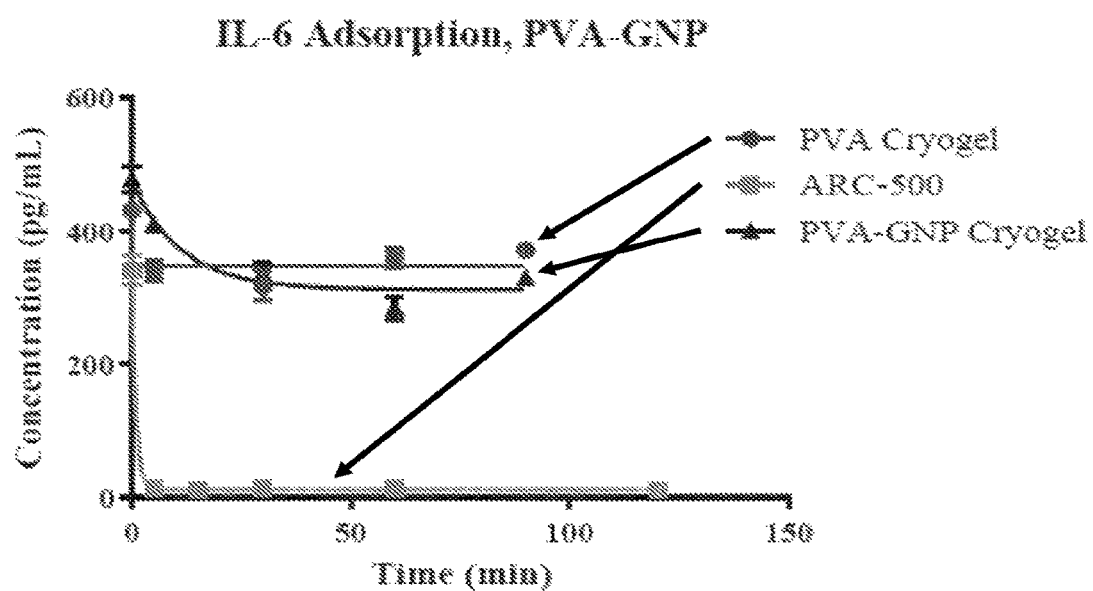

|  |  | 0 to 5 minutes | 0 to 60 minutes |
|---|---|---|---|
| Controls | IL-6 | ns | ns |
|  | IL-8 | ns | ns |
|  | TNF-α | ns | ns |
| PTFE | IL-6 | ns | ns |
|  | IL-8 | ns | ns |
|  | TNF-α | ns | ns |
| Baked-Vacuum Annealed GNP | IL-6 | **** | **** |
|  | IL-8 | **** | **** |
|  | TNF-α | **** | **** |
| PTFE-GNP | IL-6 | ns | *** |
|  | IL-8 | * | **** |
|  | TNF-α | ns | * |
| PVA Cryogel | IL-6 | ns | ns |
|  | IL-8 | **** | **** |
|  | TNF-α | ns | *** |
| ARC-500 | IL-6 | **** | **** |
|  | IL-8 | **** | **** |
|  | TNF-α | **** | **** |
| PVA-GNP | IL-6 | ** | **** |
|  | IL-8 | ns | **** |
|  | TNF-α | ns | ** |

| Legend: | |
|---|---|
| ns (not significant) | $p > 0.05$ |
| * | $p \leq 0.05$ |
| ** | $p \leq 0.01$ |
| *** | $p \leq 0.001$ |
| **** | $p \leq 0.0001$ |

FIG 32

| Material | IL-6 ms (g) | IL-8 ms (g) | TNF-α ms (g) | Total Mass (g) |
|---|---|---|---|---|
| ARC-750 | 198.6 | 77.0 | 157.2 | 432.8 |
| ARC-500 | 191.8 | 79.5 | 150.9 | 422.3 |
| ARC-300 | 205.6 | 78.3 | 210.4 | 494.3 |
| ARC-500 Vacuum Annealed | 208.1 | 71.7 | 258.0 | 537.9 |
| ARC-500 Vacuum Annealed, Acid Oxidized | 554.1 | 93.2 | 271.5 | 918.8 |
| ARC-500 Vacuum Annealed, Air Oxidized, Aminated | 216.1 | 73.9 | 268.9 | 558.9 |
| C500 Baked GNP | 394.4 | 258.5 | 460.6 | 1113.5 |
| Carbon Bead A | 78626.7 | 3151.6 | 746.1 | 82524.3 |
| Carbon Bead B | 2719.1 | 1987.2 | 595.4 | 5301.6 |
| PDC-CDC A Low MW | 1687.7 | 396.6 | 1700.1 | 3784.5 |
| PDC-CDC B High MW | 595.5 | 192.2 | 2100.8 | 2888.5 |
| PVA Cryogel | 1378.4 | 348.4 | 610.1 | 2336.9 |
| PVA-GNP | 1844.6 | 1736.4 | 593.8 | 4174.8 |
| PTFE-GNP | 1746.9 | 844.9 | 3003.5 | 5595.3 |
| PTFE | 12162.0 | 1683.6 | 1454.4 | 15300.0 |

US 11,918,723 B2

METHODS OF USING GRAPHINE NANOPLATELETS OR POLYMER-DERIVED CERAMIC CARBIDE-DERIVED CARBON TO REMOVE PROTEINS FROM BLOOD AND TO TREAT SEPSIS

CROSS-REFERENCE TO RELATED APPLICATIONS

This application is a divisional of U.S. patent application Ser. No. 16/303,687, filed Nov. 21, 2018, now U.S. Pat. No. 11,123,465, which is the National Stage Application filed under 35 U.S.C. § 371 of International Application No. PCT/US2017/034635 filed May 26, 2017, which claims priority to U.S. Provisional Patent Application No. 62/341,661, filed May 26, 2016, and to U.S. Provisional Patent Application No. 62/353,078, filed on Jun. 22, 2016. Each of these applications is incorporated by reference herein in its entirety.

GOVERNMENT RIGHTS

This invention was made with government support under Contract No. #1518999 awarded by the National Science Foundation. The government has certain rights in the invention.

TECHNICAL FIELD

This disclosure is directed to the purification of blood and blood products by the removal of cytokines from same.

BACKGROUND

High levels of pro-inflammatory cytokines are associated with high fatality of such severe conditions as sepsis and the Ebola virus disease. While being produced by human body and performing cell signaling and communication functions in physiological conditions, in pathology the quickly elevating level of cytokines, a condition also known as the "cytokine storm," results in devastating effects.

Sepsis is a life threatening condition caused by the body's dysregulated host response to infection. Sepsis symptoms (e.g. fever, hypothermia, organ dysfunction) quickly progress as a function of the cytokine cascade known as "cytokine storm", an exaggerated and skewed immune response to the incident infection. High concentrations of pro-inflammatory cytokines, such as IL-6, IL-8, and TNF-α, play a role in the development of sepsis in patients. Between 1993 and 2003, the number of hospitalizations for severe sepsis doubled in the United States. Sepsis is the primary cause of death for children and infants, and the number of incidences were estimated at 19 million cases worldwide. Current treatment methods focus on the remediation of the underlying infection and mediating the effects of over-inflammation through fluid resuscitation, broad-spectrum antibiotics, and hemodialysis. Research efforts for sepsis treatment entail immunotherapies that target pro-inflammatory cytokines, and extracorporeal hemoperfusion that adsorbs excess cytokine concentrations. Rapid reduction of blood cytokine levels back to normal is very important as the clinicians have only a few hours time to stop the fatal cytokine storm.

Therefore, there is a need for materials and techniques capable of quickly removing cytokines from blood.

SUMMARY

Certain embodiments of the present disclosure provide methods of removing proteins from blood and blood products. In some of these embodiments, the method comprises contacting the blood or blood product with a form of carbon having slit-shaped mesopores and macropores, the pore size dimensions chosen to be comparable to the size of the proteins. In some aspects, the contacting results in the removal of at least 80% of the protein from the blood or blood product in less than 120 minutes. Other rates of removal are also considered.

The carbon forms contemplated in this disclosure include thermally expanded graphite (TEG), graphene nanoplatelets (GNPs), and polymer derived ceramic carbide-derived carbon (PDC-CDC). These carbon forms may be applied in free form, films, or polymer composites (e.g., PTFE composites).

The methods are operable for a range of proteins, including those having number averaged molecular weights in a range of from 5 to 100 kDa. The methods are not necessarily limited by the molecular weights of the proteins, provided that proteins may fit within the pores of the carbon form. As such, the molecular weights of the proteins may be defined by ranges having endpoints larger or smaller than those described above and/or may be defined in ranges representing subsets of those described above.

In some embodiments, the protein is a cytokine. In exemplary examples, the cytokine can be a chemokine, interferon, interleukin, lymphokine, tumour necrosis factor, or a combination thereof. In alternative independent embodiments, the protein is independently IL-6, IL-8, TNF-α, lymphotoxin-α (aka TNF-β), or serum albumin, or a combination thereof.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIGS. 26A and 26B show SEM images of (FIG. 26A) PVA-GNP (Cryolgel-GNP) and (FIG. 26B) PTFE-GNP composites.

FIGS. 27A-27F show cytokine concentration and normalized adsorption on PVA-GNP (i.e., Cryogel-GNP) composite and its individual components.

FIG. 32 shows the mass of adsorbent for complete removal of cytokine from septic blood.

DETAILED DESCRIPTION OF ILLUSTRATIVE EMBODIMENTS

Figure 1A:
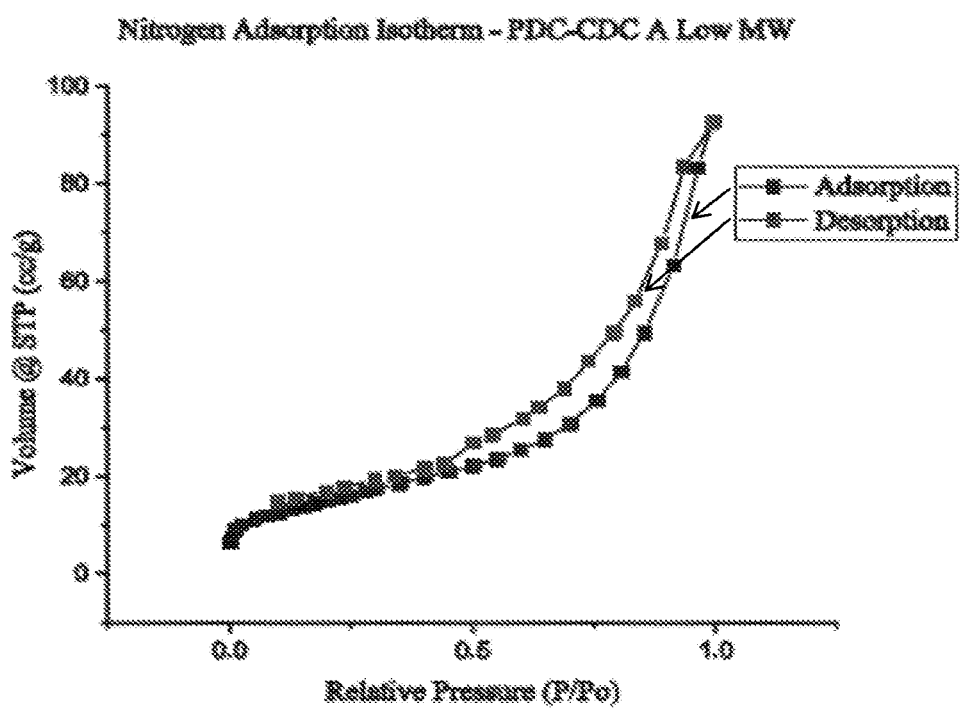
FIG. 1A shows the nitrogen adsorption isotherms for PDC-CDC A Low MW.

The present invention relates to methods of cleaning blood and blood products, the methods comprising contacting the blood or blood product with carbon forms having slit-shaped macroporosity.

Carbon is an attractive adsorbent for the hemoperfusion system, as its inert and tunable properties (e.g. porosity, surface area) allow for optimal adsorption of proteins with different dimensions. Adsorption is simple and potentially effective technique which can be performed in standard clinical environment by blood perfusion through a cartridge or column containing a material selective for cytokines, while leaving electrolytes and other small molecules in the blood stream. Recent work with carbon in the form of activated carbon (AC), cryogel-AC composites, and polymer-pyrolyzed carbon monoliths have shown that these materials are useful for adsorbing overexpressed cytokines and other toxins, but they operate too slowly and are too expensive to be practical.

The present inventors have recognized that open surface graphitic materials including thermally expanded graphite (TEG), a material made by the thermal expansion of graphite intercalated compounds (GIC), with slit-shaped macropores and large particle size (100-1000 μm), may provide the speed and efficiency for practical development, and that these materials may be used for treatment of patients suffering from the Ebola virus disease, sepsis, and other severe conditions associated with the "cytokine storm." The accordion-like structure of TEG is used as an adsorbent of crude oil in aqueous oil emulsions, adsorbing up to 70 times its mass of crude oil. A new category of low-cost graphene materials, called graphene nanoplatelets (GNP), have been developed from the delamination of TEG. GNP's have stacks of graphene layers 1-5 nanometers in thickness, and length and width dimensions between submicron and ~100 μm depending on processing. Synthesis methods include mechanical exfoliation of TEG through ultrasonication, and chemical reduction of graphene oxide. These nonporous platelets have an openly accessible and large specific surface area (~500-750 $m^2/g$), depending on the aspect ratio.

The data presented herein results from the use of GNP as an adsorbent material for hemoperfusion applications. In addition, polymer derived ceramic carbide-derived carbon (PDC-CDC) with mesoporous slit-shaped pores were investigated for their adsorption efficiency. A large and openly accessible surface of GNP's is necessary for rapid adsorption, while PDC-CDCs rely on the entrapment of proteins with pore sizes comparable to the pro-inflammatory protein size. These data suggest that a broad range of graphenic materials are excellent and selective adsorbents of proteins, including cytokines. In place of traditional pores, characteristic of activated carbons and other materials used for blood cleansing, this family of adsorbents offer open and hydrophobic surface fully available for proteins which can adapt conformations where their hydrophobic domains are directed to the hydrophobic surface and stick to it through multivalent hydrophobic interactions, while small molecules also present in blood, majority of which are hydrophilic, do not attach to graphenic surface.

The present invention may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to compositions and methods of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially" of. For those embodiments provided in terms of "consisting essentially of," the basic and novel characteristic(s) is the operability of the methods (or the compositions or devices derived therefrom) as providing a means of adsorbing cytokines, whose adsorption relies only or predominantly on the recited materials.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Throughout this specification, words are to be afforded their normal meaning, as would be understood by those skilled in the relevant art. However, so as to avoid misunderstanding, the meanings of certain terms will be specifically defined or clarified.

Again, the present disclosure is directed to methods of removing proteins from blood and blood products using specific forms of graphitic carbon. In some of these embodiments, the method or methods comprising contacting the blood or blood product with a form of carbon having slit-shaped mesopores and macropores, the pore size dimensions chosen to be comparable to the size of the proteins. According to IUPAC notation, microporous materials have pore diameters of less than 2 nm and macroporous materials have pore diameters of greater than 50 nm; the mesoporous category thus lies in the middle. Depending on the nature of the carbon forms and the specific proteins, the contacting may remove, in independent embodiments, at least 60%, 70%, 80%, 90%, or at least 95% of protein from the blood or blood product in minutes or hours, in most cases less than 2 hours (120 minutes). In other aspects, the contacting accomplished at ambient or near ambient temperatures (e.g., 10 to 35° C.), though higher or lower temperatures may also be used. In still other embodiments, the contacting is done in a dialysis arrangement, in which the blood or blood product, having been removed from a patient, is treated outside of the body of a patient and returned to the patient or separately stored for later providing to a patient or subject. Such an arrangement allows administration of natural proteins back to the patient, which natural proteins have been inadvertently or coincidentally removed from the blood or blood product.

As used herein, the terms "blood and/or blood products" refers to human or other mammalian blood, or products derived therefrom, for example platelet-depleted blood and plasma, as is commonly understood in the medical profession.

Also as used herein, the term "pore size dimensions chosen to be comparable to the size of the proteins" reflects the preference that the carbon forms readily adsorb/absorb the target proteins within the pores, or on the graphitic surfaces of these pores. Perhaps at least as important than any specific pore size is the size of the graphitic surfaces presented by the carbon forms. In some embodiments, the carbon forms have graphitic surface areas in a range of from 100 to 150 $m^2/g$, from 150 to 200 $m^2/g$, from 200 to 250 $m^2/g$, from 250 to 300 $m^2/g$, from 300 to 400 $m^2/g$, from 400 to 500 $m^2/g$, from 500 to 600 $m^2/g$, from 600 to 700 $m^2/g$, from 700 to 800 $m^2/g$, from 800 to 1000 $m^2/g$, or having a range defined by two or more of these ranges.

Figure 35:
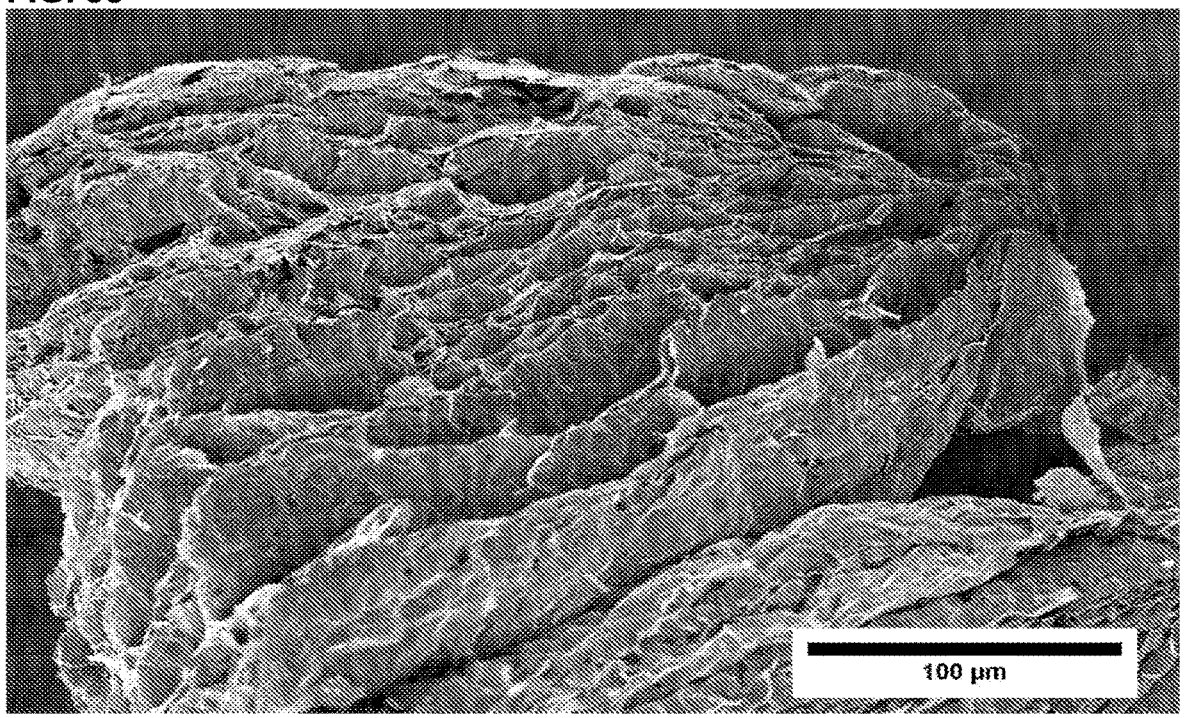
FIG. 35 shows an SEM micrograph of sample of expanded graphite.

Generally, the carbon forms of the current disclosure comprise high graphitic content. In some embodiments, the carbon form comprises thermally expanded graphite (TEG). TEG may be prepared from the thermal expansion of intercalated compounds (GIC), having particle sizes on the order of 100-1000 microns. The general principle underlying the various methods for making TEG consists of intercalating into graphite of substances or compounds such as nitric and sulfuric acid, alkali metals, and iron (III) chloride, etc., which either are themselves converted into high volume products or gas upon rapid heating or otherwise result in large volume expansion in the interlayer spaces of graphite. See e.g., A. V. Yakovlev, et al., "Thermally Expanded Graphite: Synthesis, Properties, and Prospects for Use," *Russian J. of Appl. Chem,* 79 (11) 2006). Expanded graphite may also be made by numerous other ways, for instance, by immersing natural flake graphite in a bath of chromic acid, then concentrated sulfuric acid, which forces the crystal lattice planes apart, thus expanding the graphite. Expanded graphite particles may be characterized by their worm-like appearance and characteristic, so-called "accordion" structure, formed by the stacks of dozens to hundreds graphene sheets separated by meso- and macropores of slit geometry See. e.g., FIG. 35. The surface area of the expanded graphites can be ca. 60 $m^2$ per gram of material, or higher, depending on level of further processing (e.g., ball milling). The surfaces of these adsorbents are hydrophobic, which in combination with large pores, which are much larger than typically achieved with many other adsorbents, make these materials ideal for sorption of large molecular weight hydrophobic molecules, especially of large biopolymers, i.e., proteins.

In other embodiments, the carbon form comprises graphene nanoplatelets (GNPs). Such GNPs are available from the delamination of TEG materials, comprising stacks of graphene layers 1-5 nanometers in thickness, with length and width dimensions ranging from 0.5 to 100 microns, depending on processing. These materials have openly accessible and large specific surface areas (up to 500-750 $m^2/g$) depending on the aspect ratios. Specific embodiments include those having typical surface area of 120-150 $m^2/g$ (designated Grade M); having an average thickness of approximately 2 nanometers, a diameter between 1-2 microns, and a surface area selected from 300, 500, or 750 $m^2/g$ (designated Grade C); having a typical surface area of 50 to 80 $m^2/g$, with average particle diameters of 5, 15 or 25 microns (designated Grade H); or having an average thickness of approximately 2-10 nanometers, a diameter of ca. 5 microns, and a surface area selected at 20-40 $m^2/g$.

In still other embodiments, the adsorbents can be carbon forms comprising polymer derived ceramic carbide-derived carbon (PDC-CDC). In exemplary cases, PDC-CDCs can be synthesized by pyrolysis of silicon-organic polymers at moderate temperatures (600-800° C.) followed by chlorine treatment to remove silicon and to yield carbide-derived carbons (CDCs) with a narrow pore size distribution and an average pore diameter of approximately 3-4 nm. Other techniques, such as pyrolysis and carbonization of granulated organic polymers can also be used to produce PDC-CDC with desired porosity and particle size distribution.

The carbon forms contemplated in this disclosure may be applied to the blood or blood product in free form, as films, or polymer composites (e.g., PTFE composites). In some embodiments, these carbon forms may be suspended or slurried in the blood or blood product and then removed (for example by filtration or centrifugation) or the carbon form may be incorporated into a matrix (for example a porous film, or three-dimensional structure), through or around which the blood or blood product is made to flow. Intimate mixing is preferred for speed of adsorption, but this may be balanced with the ease of separating the final carbon form containing the protein from the treated blood or blood product.

As described elsewhere herein, the pore size dimensions are preferably chosen to be comparable to the size of the proteins to be removed. Since blood and blood products normally contain certain molecules necessary for human or mammalian existence—for example, serum albumin which is a major contributor to maintaining the osmotic pressure of plasma to assist in the transport of lipids and steroid hormones, globulins which transport ions, hormones, and lipids assisting in immune function, fibrinogen which is essential for blood clotting, and other regulatory proteins, such as enzymes, and pro-enzymes—the pore size dimensions are preferably chosen to interact with protein having a number averaged molecular weight in a range of from 5 to 10 kDa, from 10 to 20 kDa, from 20 to 30 kDa, from 30 to 40 kDa, from 40 to 50 kDa, from 50 to 60 kDa, from 60 to 70 kDa, from 70 to 80 kDa, from 80 to 90 kDa, from 90 to 100 kDa, or having a range defined by two or more of these ranges, for example from 5 to 60 kDa.

In preferred embodiments, the targeted proteins are cytokines, for example a chemokine, interferon, interleukin, lymphokine, tumour necrosis factor, or a combination thereof. In some embodiments, the protein is independently IL-6, IL-8, TNF-α, lymphotoxin-α (aka TNF-β), or serum albumin, or a combination thereof.

As shown in the Examples, the use of these disclosed carbon forms can provide remarkable removal rates for various proteins. These removal rates are believed to be typical of those achievable by the disclosed methods. In independent cases, at least 60%, 70%, 80%, or 90% of the protein may be removed from the blood or blood product in less than 60 minutes. In other embodiments, at least 80% of the protein may be removed in less than 40, 20, 10, or even 5 minutes. In still other embodiments, at least 90 or 95% of the protein is removed in less than 120, 60, 40, 20, 10, or 5 minutes. Each permutation of the foregoing is considered an independent embodiment of the present disclosure.

ADDITIONAL EMBODIMENTS

The following listing of embodiments is intended to complement, rather than displace or supersede, the previous descriptions.

Embodiment 1. A method of removing proteins from blood and blood products, the method comprising contacting the blood or blood product with a form of carbon having slit-shaped mesopores and macropores, the pore size dimensions chosen to be comparable to the size of the proteins. In some Aspects of this Embodiment, the contacting results in the removal of at least 80% of the protein from the blood or blood product in less than 120 minutes. In other Aspects, the contacting accomplished at ambient or near ambient temperatures (e.g., 10 to 35° C.), though higher or lower temperatures may also be used.

Embodiment 2. The method of Embodiment 1, wherein the carbon form comprises thermally expanded graphite (TEG). The various aspects of TEG are described elsewhere herein.

Embodiment 3. The method of Embodiment 1, wherein the carbon form comprises graphene nanoplatelets (GNPs).

Embodiment 4. The method of Embodiment 1, wherein the carbon form comprises polymer derived ceramic carbide-derived carbon (PDC-CDC).

Embodiment 5. The method of any one of Embodiments 1 to 4, wherein the protein has a molecular weight in a range of from 5 to 60 kDa.

Embodiment 6. The method of any one of Embodiments 1 to 5, wherein the protein is a cytokine.

Embodiment 7. The method of Embodiment 6, wherein the cytokine is independently a chemokine, interferon, interleukin, lymphokine, tumour necrosis factor, or a combination thereof.

Embodiment 8. The method of any one of Embodiments 1 to 7, wherein the protein is independently IL-6, IL-8, TNF-α, lymphotoxin-α (aka TNF-β), or serum albumin, or a combination thereof.

Embodiment 9. The method of any one of Embodiments 1 to 8, wherein at least 80% of the protein is removed from the blood or blood product in less than 60 minutes. In other Aspects of this Embodiment, at least 80% of the protein is removed in less than 40, 20, or 10 minutes. In still other Aspects, at least 90 or 95% of the protein is removed in less than 120, 60, 40, 20, 10, or 5 minutes.

Embodiment 10. The method of any of embodiments 1 to 9 wherein the carbon form is dispersed within a polymer composite.

Embodiment 11. The method of any of Embodiments 1 to 10 wherein the GNP is vacuum annealed C-500.

Embodiment 12. The method of Embodiment 11 wherein the C-500 has been vacuum annealed, air oxidized, and aminated.

Embodiment 13. The method of any of Embodiments 1 to 10 wherein the GNP is ARC-750.

Embodiment 14. The method of any of Embodiments 1 to 13 wherein the protein is IL-6.

Embodiment 15. The method of any of Embodiments 1 to 13 wherein the protein is IL-8.

Embodiment 16. The method of any of Embodiments 1 to 13 wherein the protein is TNF-α.

Embodiment 17. A method of treating sepsis in a patient in need thereof, comprising performing the method of any one of Embodiments 1-16 to the blood of the patient.

Embodiment 18. The method of Embodiment 17, wherein the blood or blood products are processed through a hemoperfusion cartridge.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Commercially purchased nanoplatelets were defunctionalized and characterized for their particle size, surface area, and cytokine adsorption performance. PDC-CDC was synthesized from the chlorination of high molecular weight and low molecular weight polymers. Rapid adsorption kinetics were observed for pro-inflammatory cytokines, as well as a larger albumin molecule, which is present in blood plasma and adsorbs onto the GNPs upon contact.

Example 1.1: Materials Synthesis

Graphene Nanoplatelets (GNPs): Graphene nanoplatelets were purchased commercially for experimental purposes (xGnP™, XG Sciences©, Lansing, Mich., USA). GNPs were synthesized using exfoliation of natural graphite to form thermally expanded graphite (TEG). Through ball milling of TEG, GNP powder with a particle size of ca. 1 μm (in lateral dimensions) is formed. GNPs also underwent heat treatment in flowing nitrogen gas.

Graphene nanoplatelets were purchased commercially for experimental purposes (xGnP™, XG Sciences©, Lansing, Mich., USA). These GNPs were synthesized through first creating thermally expanded graphite (TEG) by oxidation and intercalation followed by sonication and ball milling. The resulting GNP powder was controlled to yield an average nanoplatelet thickness of 2 nm, and while lateral dimensions varied by product. Three products were purchased, xGnP C-750, C-500, and C-300. Each number in the product name corresponds to the expected specific surface area of the material (e.g. 750 m$^2$/g, 500 m$^2$/g, and 300 m$^2$/g). These materials are referred to herein with an additional "AR" at the beginning of the name (e.g. ARC-750, ARC-500, ARC-300) to signify that it is "As-Received" from the vendor.

For some experiments, the GNPs were modified. First, defunctionalized and functionalized GNPs, were synthesized using a variety of high temperature processes. For all surface chemistry experiments, ARC-500 was used as the base material. For defunctionalization, 2 g of ARC-500 was placed in a graphite crucible and loaded into a vacuum furnace (Solar Atmospheres, PA, USA). The furnace was outgassed at 10$^{-6}$ torr for 24 hours, at room temperature. Following outgassing, the furnace was heated at 600° C./hour while still under vacuum to a peak temperature of 1400° C., above the graphitization temperature. Vacuum annealing protocols were adapted from B. Dyatkin and Y. Gogotsi, "Effects of structural disorder and surface chemistry on electric conductivity and capacitance of porous carbon electrodes," *Faraday Discussions*, vol. 172, pp. 139-162, 2014. The temperature and vacuum was held for 8 hours, and then cooled down to room temperature. Vacuum annealed samples experienced a mass loss of ~10% from impurity removal.

In some experiments, vacuum annealed GNPs were subjected to air oxidation to activate the surface, followed by anhydrous ammonia gas amination to add amine groups to the surface. Air oxidation parameters were adopted from S. Osswald, C. Portet, Y. Gogotsi, G. Laudisio, J. P. Singer, J. E. Fischer, et al., "Porosity control in nanoporous carbide-derived carbon by oxidation in air and carbon dioxide," *Journal of Solid State Chemistry*, vol. 182, pp. 1733-1741, 2009, and the oxidation temperature was determined by thermogravimetric analysis. Amination parameters were adopted from a number of sources, including C. Portet, D. Kazachkin, S. Osswald, Y. Gogotsi, and E. Borguet, "Impact of synthesis conditions on surface chemistry and structure of carbide-derived carbons," *Thermochimica Acta*, vol. 497, pp. 137-142, Jan. 10, 2010; and B. Dyatkin, I. U. G. Gogots i, and E. Drexel University. College of, "Influence of Structure and Surface Chemistry of Porous Carbon Electrodes on Supercapacitor Performance," Dissertation/Thesis, 2016. 50 mg of vacuum annealed GNPs was placed on a quartz crucible and loaded into a tube furnace. Under flowing argon gas (Ar) at 800 cc/min, the temperature was increased to 541° C. at 10° C./min, at which point the gas was changed immediately to flowing air at 800 cc/min. After 4 hours of air oxidation at 541° C., the air was turned off and Ar was turned on at 800 cc/min. The temperature was raised again to 600° C. at 10° C./min, and then was held while the gas was changed to ammonia at a flow rate of 800 cc/min. After 4 hours of ammonia treatment at 600° C., the gas was changed to Ar at a flow rate of 200 cc/min and the furnaces were cooled down overnight to room temperature. After the sample was removed from the furnace, it was massed and a 20% mass loss was seen, due to the etching of carbon atoms from oxidation and amination.

Acid oxidation of the GNPs was based on the parameters of acid oxidation from S. Osswald, M. Havel, and Y. Gogotsi, "Monitoring oxidation of multiwalled carbon nanotubes by Raman spectroscopy," *Journal of Raman Spectroscopy*, vol. 38, pp. 728-736, 2007. 150 mg of vacuum annealed C-500 GNPs was added to 15 mL of fuming nitric acid and 15 mL of 36 M sulfuric acid in a flask. The flask was heated at a rate of 1° C./min from room temperature to 70° C., at a mixing speed of 100 rpm. To prevent evaporation of acid, a reflux condenser was used with flowing water. After 4 hours of oxidation, the acid and sample was filtered, and then filtered again with ≥500 mL of distilled water. The sample was then dried overnight at ~100° C. in a drying oven. In order to ensure that all of the acid was removed, a more thorough washing process was performed after the sample was dry. All of the acid oxidized samples were distributed into microcentrifuge tubes and 1.5 mL of distilled water was added to each. After 10 seconds of vortex mixing of each and centrifuging, the supernatants of multiple samples were tested for pH using a pH strip. The tubes were centrifuged, the water was removed, and the process was repeated until the pH of multiple tubes was neutral. The samples were then suspended together into more distilled water, filtered, and dried again overnight.

GNP Composites:

GNP-PTFE film was prepared by mixing GNP with PTFE (60% w/w) solution (Sigma-Aldrich, US) at a ratio of 19:1 in the presence of ethanol. Evaporation of ethanol leaves a homogenous GNP-PTFE dense slurry; this was rolled out into a cohesive, freestanding film. The GNP powder used was the C-500 product from XG Sciences, but was previously baked in an inert environment to remove impurities after synthesis. This is known as "Baked-C500 GNP." The GNP was also vacuum annealed prior to adding to PTFE. GNP was put into a graphite crucible and placed into a vacuum furnace (Solar Atmospheres, PA, USA). The system was outgassed to $10^{-6}$ torr for 24 hours, gradually heated in isothermal steps between 300-1800° C., and held at 1800° C. for eight hours. This process removes functional groups and heals defects of the GNP.

Cryogel-GNP ARC-500 GNPs from XG Sciences (xGnP™, MI, USA) were used in the synthesis of the cryogel-GNP composite. Cryogel composites were synthesized by mixing 5 w/v % poly(vinyl) alcohol (PVA) (Sigma-Aldrich, Pool, UK) as the monomer, 0.5 w/v % glutaraldehyde (Sigma-Aldrich, Pool, UK) as the crosslinker, and 5 w/v % 500 nm ARC-500 in distilled water. After mixing, the solution was pipetted into glass syringes and frozen in an ethanol bath at −12° C. overnight. After freezing, cryogel samples were removed from the ethanol bath and thawed to room temperature. The cryogel composite is also referred to herein as PVA-GNP.

PDC-CDC: Polymer-derived carbide-derived carbon (PDC-CDC) was synthesized from either a high molecular weight or low molecular weight polymeric precursor. This precursor was treated at 1550° C. to form a ceramic, treated at 830° C. under flowing chlorine gas for 3 hours, and then hydrogenated at 630° C. for 2 hours under flowing hydrogen gas. The PDC-CDC prepared in this manner from the high molecular weight polymeric precursor is referred to herein as PDC-CDC B High MW. The PDC-CDC prepared in this manner from the low molecular weight polymeric precursor is referred to herein as PDC-CDC A Low MW.

Example 1.2: Materials Characterization

Nitrogen Sorption:

A Quadrasorb Pore Size Analyzer (Quantachrome, FL, USA) was used to characterize the porosity and surface area of the materials. This is accomplished by monitoring the adsorption and desorption of nitrogen gas and measuring the recorded volume adsorbed and desorbed as a function of the relative pressure in the system. The relative pressure is the pressure in the bulb divided by ambient environment or 760 torr. When the relative pressure equals one, the sample is saturated with gas and the gas is desorbed from the material by a pressure change in the system. One key assumption made in the experimental procedure is that adsorption is occurring in slit-shaped pores, due to the graphitic ordering of the materials used. Different models were used to calculate the specific surface area of the materials, including quenched solid density functional theory (QSDFT) and the Brunauer-Emmett-Teller theory (BET). QSDFT is also utilized to fit a pore width to the given adsorbed volume from model adsorbent systems and generate a pore size distribution. See S. Brunauer, P. H. Emmett, and E. Teller, "Adsorption of Gases in Multimolecular Layers," *Journal of the American Chemical Society*, vol. 60, pp. 309-319, 1938/02/01 1938; C. Lastoskie, K. E. Gubbins, and N. Quirke, "Pore size heterogeneity and the carbon slit pore: a density functional theory model," *Langmuir*, vol. 9, pp. 2693-2702, 1993/10/01 1993.

The Brunauer-Emmett-Teller equation (S. Brunauer, P. H. Emmett, and E. Teller, "Adsorption of Gases in Multimolecular Layers," Journal of the American Chemical Society, vol. 60, pp. 309-319, 1938/02/01 1938) was used to calculate the specific surface area and is a function of volume of gas adsorbed, equilibrium pressure, pressure given a certain volume, and the volume of gas required to form a monolayer. A linear regression of data points based on this equation and relative pressures between 0.05 and 0.30 $P/P_o$ were employed to find the surface area, and then normalized to find the specific surface area (SSA). This relative pressure range correspond to the relative pressures where a monolayer of gas is formed. QSDFT provided another SSA value, along with the pore size distribution.

For PDC-CDC, 50-60 mg of PDC-CDC A Low MW and PDC-CDC B High MW were added to glass sample holders, and put under vacuum at 100 millitorr at 120° C. for 24 hours to remove contaminants and gas molecules from the pores. After degassing, the glass cells were backfilled for five seconds with nitrogen gas to prevent air from entering the adsorbents, and added to the Quadrasorb analyzer. The volume of adsorbed nitrogen was measured as the relative pressure started ~0 and reached ~1, then desorption occurred. Calculations for surface area and pore volume were performed assuming that the system is at 77K, so the sample holder is suspended in a liquid nitrogen dewar during the adsorption experiment. Liquid nitrogen is used because adsorption of nitrogen is more energetically favorable in the liquid state than the gaseous state, so the nitrogen gas used is liquefied before adsorption [128]. The data was analyzed using Quantachrome's data analysis software (Quantachrome QuadraWin™ 5.1).

For GNPs, the nitrogen sorption experiments were performed similarly. 3-150 mg was used for the nitrogen adsorption experiments, and the SSA was calculated using both BET and QSDFT models. The specific surface area (SSA) of GNP was measured through nitrogen sorption at −196° C., using a Quadrasorb pore size analyzer (Quantachrome, FL, USA). Adsorption isotherms were analyzed using the Brunauer-Emmet-Teller (BET) method, in a relative pressure range of 0.05-0.3 $P/P_o$. Quenched solid density functional theory (QSDFT) was also used to calculate the SSA. Slit-shaped pores were assumed for the calculations. A scanning electron microscope (Zeiss Supra 50VP field-emission SEM) were used to produce high-resolution imaging. A Malvern Zetasizer Nano ZS was used for particle size measurements by dynamic light scattering.

A Quadrasorb Pore Size Analyzer (Quantachrome, FL, USA) was used to measure the adsorbed and desorbed volumes of nitrogen by the test samples at relative pressures between $2.46 \cdot 10^{-3}$ and 0.995 at 77.4 K. 0.08 grams of GNP were loaded into glass cells, outgassed under 100 millitorr at 120° C. for 24 hours before analysis. The data was analyzed using Quantachrome data analysis software (Quantachrome QuadraWin™ 5.1). The specific surface areas were calculated using the Brunauer, Emmett and Teller (BET) method while the pore size distribution was estimated using quenched solid density functional theory (QSDFT).

For GNP Composites, the nitrogen sorption experiments were performed similarly. 80-95 mg of sample was used to create nitrogen adsorption isotherms after outgassing for 24 hours, and the SSA was calculated with the BET equation and QSDFT model. The pore size distribution was calculated using the QSDFT model, assuming slit-shape shaped pores.

Dynamic Light Scattering.

Dynamic light scattering (DLS) using a Malvern Zetasizer Nano ZS (Malvern Instruments Ltd, Malvern, UK) was used for particle size measurements.

For PDC-CDC, low concentrations of PDC-CDC A Low MW and B High MW were added to plastic cuvettes (DTS0012, Malvern Instruments Ltd, Malvern, UK) at 25° C. Three measurements, each of 10 scans, were taken and averaged to obtain the Z-average particle size. Polydispersity index (PDI) values were also determined.

For GNPs, a similar procedure was used. In addition, particle size as a function of time was determined for particle stability analysis of ARC-750, ARC-500, and ARC-300. At 2-minute intervals, from 0 to 100 minutes, the particle size was measured. Zeta potential testing was conducted using an MPT-2 autotitrator which monitored changes in pH induced by the addition of acidic (pH=4) or basic (pH=10) buffer solutions. While a magnetic stir bar kept the sample circulated, titrations were controlled to cover a pH range of 6 and 8. Zeta potential was measured with a varied amount of data points (ranging from 12 to 33 runs), with the machine measuring Zeta potential 3 times per titration. Each data point presented is the average of the 3 runs per pH value, with standard error of mean error bars. Measurements were taken using a disposable capillary cell (DTS1070, Malvern Instruments Ltd, Malvern, UK) at 25° C.

Scanning Electron Microscopy

A scanning electron microscope (Zeiss Supra 50VP field-emission SEM) were used to produce high-resolution imaging. The surface and internal porous morphologies of GNP powder and GNP composites were characterized by scanning electron microscopy (SEM) (Zeiss Supra 50VP field-emission SEM, USA). For GNPs, a 5 kV accelerating voltage and working distance of 4.2 mm were used. For the PVA-GNP cryogel, a 5 kV accelerating voltage and working distance of 7.3 mm were used. For the PTFE-GNP film, a 5 kV accelerating voltage and working distance of 8.6 mm were used.

Transmission Electron Microscopy

A transmission electron microscope (TEM) captured images of individual GNP nanoplatelets and agglomerates using a JEM 2100 TEM with a 200 kV accelerating voltage. Samples were dropped onto a lacey carbon grid by dispersion in ethanol and pipetting onto the grid.

Raman Spectroscopy

Raman spectra of the GNPs were created from a Raman microspectrometer (InVia, Renishaw plc, Gloucestershire, UK) using a He/Ne ion laser with a wavelength of 633.2 nm. Reflected light from the sample was guided to the detector by a grating with 1200 lines/mm. The resolution of the results is ~2 cm-1. Raman spectra were collected and then plotted as Raman shift with respect to peak intensity. X. Xie, T. Makaryan, M. Zhao, K. L. Van Aken, Y. Gogotsi, and G. Wang, "MoS2 Nanosheets Vertically Aligned on Carbon Paper: A Freestanding Electrode for Highly Reversible Sodium-Ion Batteries," Advanced Energy Materials, vol. 6, pp. n/a-n/a, 2016. Peak positions and intensities of G and D were fitted using a mixed Gaussian-Lorentzian distribution.

Thermogravimetric Analysis (TGA)

Thermogravimetric analysis (TGA) was used to identify the optimal air oxidation temperature. A TA Q50 TGA analyzer (TA Instruments, DE, USA) was used, and a very small amount of vacuum annealed C-500 GNP (5-10 mg) was put into the sample holder. The flow rate of air was 10 cc/min, and the sample was heated at a rate of 10° C./min. The percent of mass remaining was then plotted with respect to the temperature. After impurities were removed at I 10° C. and the sample was equilibrated, the mass remaining was normalized to 100% again. The temperature at which 0.9% mass loss occurred after reaching 110° C. was defined as the onset of oxidation.

X-Ray Photoelectron Spectroscopy (XPS)

X-ray photoelectron spectroscopy (XPS) and energy dispersive spectroscopy (EDS) were used as complimentary techniques to identify surface composition of the materials. A Physical Electronics VersaProbe 5000 (ULVAC-PHI, MN, USA) XPS was used. Each survey scan for composition was completed with a pass energy of 117.4 eV, energy step of 0.5 eV, time of 150 ms per step, and repeated twice. Elemental composition by atomic percent was then calculated for each sample. To find and identify functional groups and their characteristic binding energies, a pass energy of 23.5 eV, energy step of 0.05 eV, time of 300 ms per step, and 10 repeats was used. The raw data set for the nitrogen peaks of aminated samples was analyzed by fitting the peaks to a Voight profile, which is a mix of Gaussian and Lorentzian distributions. See E. Josyula, "8.3.2 Line Shape of Emission Lines and Line Broadening," in *Hypersonic Nonequilibrium Flows—Fundamentals and Recent Advances—Progress in Astronautics and Aeronautics*, Volume 247, ed: American Institute of Aeronautics and Astronautics/Aerospace Press. Each peak corresponds to an intensity of counts per second, or CPS, detected at a certain binding energy. Characteristic peaks of bonds between nitrogen containing groups are observed and fitted. EDS uses the setup for SEM previously described, with a SE2 detector used and scanning 1 mm$^2$ of each sample for 30 seconds. The atomic and weight percent compositions were calculated by INCA software by Oxford Instruments (OxfordInstruments, Oxfordshire, UK).

Example 1.3: Biological Characterization

Cytokine Adsorption Experiments

Fresh frozen blood plasma (StemCell Technologies, NJ, USA and Cambridge Bioscience Ltd., Cambridge, UK) was used for experiments. For the blood purchased from Cambridge Bioscience, sodium citrate anticoagulant was added (Cambridge Bioscience Ltd., Cambridge, UK) and for the blood from StemCell, acid citrate dextrose (ACDA) anticoagulant was used (StemCell Technologies, NJ, USA). Recombinant human cytokines IL-6, IL-8, and TNF-α (BD Biosciences, NJ, USA) were purchased to add excess concentrations of these cytokines to the blood plasma. The amounts of each cytokine added are physiologically relevant to sepsis conditions. IL-6, IL-8, and TNF-α were separately reconstituted at a concentration of 1 µg/mL into a solution of BSA (Sigma-Aldrich, MO, USA) in 1×PBS (ThermoFisher, MA, USA) at a concentration of 10 mg/mL. All three cytokines were split into 40 µL aliquots at a concentration of 1 µg/mL and stored at −80° C. 35 µL of each cytokine at this concentration was added to 35 mL of blood plasma. The starting concentration of each cytokine in the 35 mL plasma was about 1,000 µg/mL.

Enzyme-linked immunosorbent assay (ELISA) is an immunoassay technique used to characterize the concentrations of cytokines. The assay uses a capture antibody adsorbed to a hydrophobic plastic plate to bind to a specific antigen, in this case, either IL-6, IL-8, or TNF-α. After capturing the cytokine, a conjugated antibody is added to complete the "sandwich." This "detection antibody" is conjugated with biotin; after adding an enzyme, a chromogenic substrate is used to precipitate products that emit a blue color. J. R. Crowther, The ELISA Guidebook. Totowa, N.J.: Humana Press, 2000. The optical density or absorbance of light can be measured using a spectrophotometer at the wavelength of blue light, 450 nm. Based on a standard curve, the concentration of a cytokine can be calculated as a function of the absorbance in accordance with Beer's Law, which states that there is a linear relationship between absorbance and concentration.

A sandwich ELISA was used to characterize the concentration of cytokines in the blood. BD Biosciences' OptEIA™ Human IL-8, IL-6, and TNF-α kits were purchased. Lyophilized cytokine standards were reconstituted at concentrations instructed by the technical data sheet, and serial dilutions of these standards were completed in the plate. These standards were originally reconstituted into 1 mL of distilled water, stored at −80° C. and diluted in assay diluent to an appropriate starting concentration for the standard curve. Blood plasma samples were also diluted in assay diluent for their concentrations to fall within the standard curve. Multiple washing steps were used between assay steps to remove excess antibodies and reagents.

The overall ELISA protocol was as follows:

1) Coat plates overnight with diluted capture antibody in coating buffer (100 µL/well).

2) Wash plates three times with ≥300 µL/well washing buffer, add 200 µL/well of assay diluent to each well, then incubate at room temperature for one hour.

3) Wash plates three times with ≥300 µL/well washing buffer, add 100 µL/well of serial dilutions of standards in plate, dilute plasma samples in assay diluent in the respective well, then incubate at room temperature for two hours.

4) Wash plates five times with ≥300 µL/well, add 100 µL/well "working detector" (detection antibody+streptavidin-horseradish peroxidase conjugate), then incubate at room temperature for one hour.

5) Wash plates seven times with ≥300 µL/well, soaking 30 seconds to 1 minute between each wash. Next, add 100 µL/well substrate solution of tetramethylbenzidine (TMB) and hydrogen peroxide, then incubate at room temperature for 30 minutes in the dark.

6) Add 50 µL/well of stop solution (1M $H_3PO_4$) to the wells.

7) Read absorbance using a Tecan Infinite @0 200 NanoQuant Spectrophotometer (Tecan Austria GmbH, Austria), at a wavelength of 450 nm.

Samples were repeated in two wells for replicates, and empty wells with just assay diluent were used to monitor background noise from the spectrophotometer. During washing steps, plates were flicked after filling wells and then tapped multiple times after the last wash in order to fully remove the wash buffer. The plates used were Costar® polystyrene medium-binding 96-well plates with low evaporation lids (Corning Incorporated, Corning, N.Y., USA).

After the ELISA assays were completed, standard curves based on the methodology discussed previously were generated. These standard curves used a linear regression with an R2 value of −0.99. A two-way ANOVA multiple comparisons test using GraphPad Prism 6 (GraphPad Software, CA, USA) was utilized to determine statistical significance between concentration over time for plasma that was not incubated with the adsorbents. To analyze the concentration versus time and normalized adsorption data (in units of mass of cytokine per unit mass of adsorbent), two regressions were used. An exponential decay regression is seen in Equation 4.1, which shows the general equation. $C_0$ (or $q_0$) is the initial concentration, $C_\infty$ (or $q_\infty$) is the concentration at infinite time, k is a rate constant, and time in minutes is expressed as t. In order to calculate the equilibrium concentration of adsorption normalized by an adsorbent mass, $q_e$, Ho and McKay's pseudo second-order kinetic model was applied. Y. S. Ho and G. McKay, "Pseudo-second order model for sorption processes," *PROCESS BIOCHEMISTRY*, vol. 34, pp. 451-465, 1999. Equations 4.2 and 4.3 show the calculations for $q_t$ and finding $q_e$ based on the pseudo second-order model. $V_p$ is the volume of plasma, $C_0$ is the original concentration of cytokine, $C_t$ is the concentration at time t and $m_a$ is the adsorbent mass. For equation 4.2, a linear correlation is derived where $y=t/q_t$, $n=1/q_e$ and $b=1/(k*q_{e2})$.

$$C_t = \frac{C_0 - C_\infty}{e^{k+t}} + C_\infty \quad (4.1)$$

$$q_t = \frac{(C_0 - C_t)*V_p}{m_a} \quad (4.2)$$

$$\frac{t}{q_t} = \left(\frac{1}{k*q_e^2}\right) + \left(\frac{1}{q_e}\right)*t \quad (4.3)$$

For GNPs, the following six samples were tested with a ratio of 10 mg to 1 mL spiked plasma: ARC-750, ARC-500, ARC-300, vacuum annealed C-500, vacuum and acid oxidized C-500, and vacuum annealed, air oxidized, and aminated C-500. Another three samples were tested for cytokine adsorption with 25, 50, and 100 mg of adsorbent to 1 mL spiked plasma. All nine variations of GNPs were tested in triplicate, and incubated with plasma at 37° C. and were shaken at 125 rpm for 0, 5, 15, 30, 60, and 120 minutes. Samples were centrifuged at 13,000 G at each time point. Plasma supernatant was collected and stored at −20° C. for storage prior to ELISA. An important note is that as-received GNP powder did not disperse well in plasma when incubated. To mitigate lack of uniform contact with the powder, all as-received samples were pipetted up and down in blood plasma and vortex mixed for 15 seconds to ensure dispersion. Defunctionalized and functionalized samples were also vortex mixed for 20 seconds, but not pipetted, due to particles sticking to the inside of pipette tips when attempting to pipette up and down. ELISA assays were conducted on the plasma supernatants of all samples. Dilutions were completed for blood plasma samples to fall within the standard curve with an R2 value of 0.99.

Fresh frozen human blood plasma with sodium citrate anticoagulant (Cambridge Bioscience Ltd., Cambridge, UK) was defrosted and augmented with recombinant human cytokines (IL-8, IL-6, TNF-α) (BD Biosciences, NJ, USA) at concentrations of 1000 μg mL$^{-1}$ for each cytokine. 0.23 g of GNP, or 1 mL of GNP, was added to 9 mL of PBS and equilibrated overnight in vacuum. After centrifugation, 100 μl of GNP was added to 900 μl of spiked plasma in Eppendorf tubes. 0.20 g of PDC-CDC samples were incubated with 1 mL of spiked plasma in Eppendorf tubes. Adsorbents were incubated at 37° C. while shaking at 150 rpm. At 5, 30, 60, 90, and 1200-minute time points, samples were centrifuged at 3500 rpm. The supernatant was collected and stored at −20° C. prior to ELISA analysis (BD Biosciences, NJ, USA) for cytokine concentration. Adsorption studies were completed in triplicate (n=3), and plasma with excess cytokine concentration was used as a positive control.

In some experiments, the cytokine markers adsorption profile of GNP was evaluated by incubating 10% w/v of GNP with fresh frozen human blood plasma (Cambridge Bioscience Ltd., Cambridge, UK) spiked with I ng/ml IL-8, IL-10, IL-6, IL-10 and TNF-α (BD Biosciences, UK) for 60 minutes. Concentrations of the selected cytokine marker were determined using BD Cytometric Bead Array (CBA) Human Inflammatory Cytokines Kit (BD Biosciences, UK). The GNP-PTFE film adsorption kinetics of selected cytokine markers IL-8, IL-6 and TNF-α, were compared with PTFE film and GNP powder. The selected cytokine marker concentrations were measured by the enzyme-linked immunosorbent assay (ELISA) using a BD Biosciences ELISA set. Two-way ANOVA statistical analysis was performed using Prism 6.05 (PraphPad Software, Inc.).

For GNP Composites, 20 mg of either composite was massed, preconditioned in 1×PBS for 24 hours, and added to 1 mL of spiked blood plasma in microcentrifuge tubes. The plasma and adsorbents were incubated at 37° C. while shaking at 125 rpm. Samples were collected at 5, 30, 60, and 90 minutes, and were compared against positive (spiked plasma without adsorbents) and negative controls (plasma without excess cytokines or adsorbent). After their respective time points, samples were taken out of the shaker, centrifuged at 13,000 G for 5 minutes, and the plasma supernatant was removed and stored at −20° C. for ELISA assays. ELISA assays were conducted on the plasma supernatants of all samples. Dilutions were similarly completed on plasma samples to fall within the standard curve with an R2 value of 0.99.

For PDC-CDC, 20 mg of PDC-CDC A Low MW and PDC-CDC B High MW were added to five non-stick microcentrifuge tubes each (VWR®, PA, USA). All samples were preconditioned in 1 mL of 1× phosphate buffered saline (PBS) (ThermoFisher, MA, USA) overnight to prevent adsorption of environmental contaminants in the air and removal of any surface contaminants. Samples in PBS were then centrifuged at 13,000 G to remove the PBS supernatant. For studies using PDC-CDC carbon, the plasma from Cambridge Bioscience Ltd was used. 1 mL of the "spiked" blood plasma was added to each tube that contained 20 or 10 mg of adsorbent, vortex mixed for full contact with the plasma, and then shaken at 125 rpm at 37° C. The samples in plasma were taken out of the shaker at 5 minutes, 15 minutes, 30 minutes, 60 minutes, and 90 or 120 minutes. After centrifugation at 13,000 G for 5 minutes, the plasma supernatant was taken out and stored at −20° C. In an effort to monitor any external effects to cytokine concentration, each microcentrifuge tube was paired with an additional tube filled with 1 mL of spiked blood plasma, but without the adsorbent. An additional tube of plasma was also tested that did not have any excess cytokines added in. These experiments were all tested in triplicate (n=3).

Example 1.4: Biocompatibility Assessment

A colorimetric cell proliferation assay was conducted to determine the interaction of the adsorbents with cells. This is determined through a conversion of the compound MTS tetrazolium, which is digested by cells through metabolic activity. The conversion product is a colored solution, which is then read via a spectrophotometer for its optical density. The cell viability with the adsorbent was determined by the amount of metabolic activity occurring from the MTS conversion. See "CellTiter 96@ AQeuous One Solution Cell Proliferation Assay," Promega, Madison, Wis. TB245, 2012.

Human hepatic epithelial cell line HepG2 (CRL-11997™, ATCC®, VA, USA) was selected for assessing the cytotoxicity of GNP powder. The HepG2 cell line was maintained by passaging at 80% confluency and suspension in Eagle's Minimum Essential Medium (MEM) (Sigma-Aldrich, Pool, UK) supplemented with 10% fetal calf serum (FCS) (Sigma-Aldrich, UK). For the in vitro cytotoxicity assessment, GNP powder (10% v/v) was washed with phosphate-buffered saline solution (PBS) and followed by pre-conditioning in culture medium for 24 hours. HepG2 cells were harvested and seeded to 96 well plates at a density of $1\times10^5$ cells/well. The plates underwent incubation for 18 hours at 37° C. in a humidified environment with 5% $CO_2$ before they were treated with different concentrations of pre-conditioned GNP powder for 24 hours. Silver nanoparticles were included as a cytotoxic control, while culture medium was used as a non-cytotoxic control. HepG2 cell viabilities after treatments were determined by comparing cellular MTS conversion using CellTiter 96® Aqueous One Solution Cell Proliferation Assay (Promega, Southampton, UK).

ARC-500 GNP powder was dispersed in water in a 10% volume solution, and further diluted to 1% v/v solution for cell incubation. HepG2 cells were harvested and seeded to a 96 well plate at a density of $1*10^4$ cells/well. After incubation of the plates at 37° C. in a 5% $CO_2$ humidified environment for 24 hours, different concentrations of GNP-water solution were added to the plates, with silver nanoparticles included as acytotoxic positive control and MEM as a non-cytotoxic negative control. The CellTiter 96@ Aqueous One Solution Cell Proliferation Assay (Promega, Southampton, UK) was used to compare conversion of MTS by cells. Absorbency was measured using a Biotek ELx800 spectrophotometer, measuring absorbance at 490 nm (Biotek, VT, USA). Cell viability was calculated by comparing the relative absorbency to the negative control, cells incubated with just MEM culture medium.

Prior to incubation, PDC-CDC samples were massed (150 mg) and preconditioned in 1.5 mL of PBS overnight under vacuum. Cell counts were determined by staining cells using a 1:1 volume ratio of trypan blue to cell suspension in MEM and analyzing using a hemocytometer grid under a standard optical microscope. HepG2 cells were harvested and seeded at a density of 800,000 cells/mL in high-binding affinity 96 well plates (100 μL/well). The plates were incubated at 37° C. for 24 hours at 5% $CO_2$ in a humidified environment. After aspiration of the MEM and cell suspensions, 100 μL of 10% w/v solution of PDC-CDC powders and MEM was incubated in the plates. For the wells with seeded cells, an additional 100 μL of MEM was added in order to ensure ample access to nutrients. For controls, wells were incubated with adsorbent suspended in medium or with only medium. A positive cytotoxic control incubated with cells was PVC polymer containing 0.57% dibutyltin maleate (Hydro Polymers Ltd, London, UK). After 24 hours of incubation, the medium was aspirated from the wells, wells were washed and aspirated with PBS, and 120 μL/well of MTS reagent and MEM in a 1:5 volume ratio was added to the wells for 2 hours. 100 μL was taken out and transferred to a new plate, where the MTS protocol on the spectrophotometer was used, measuring absorbance at 490 nm. Cell MTS conversion was then calculated as a function of absorbency. The assay kit used was CellTiter 96 @) Aqueous One Solution Cell Proliferation Assay (Promega, Southampton, UK).

Example 1.5: BSA Adsorption Experiment

Bovine serum albumin (BSA) (Sigma-Aldrich, MO, USA) was added to distilled water in concentration of 1 mg $mL^{-1}$. GNP adsorbents were weighed (0.02 g) into 15 Eppendorf tubes, and incubated with 1 mL of BSA solution 37° C. while shaking at 200 rpm. At 5, 15, 30, 60, 120-minute time points, samples were centrifuged at 17,000 g, and the supernatants were collected. To improve purity of the nanoplatelets, GNP was vacuum annealed at 1400° C. for 8 hours prior to adsorption experiment. A NanoDrop 1000 spectrophotometer (Thermo Fisher Scientific, MA, USA) was used to measure the concentration of BSA in the supernatant. Adsorption studies were completed in triplicate (n=3).

Example 2: Results and Discussion

Figure 1B:
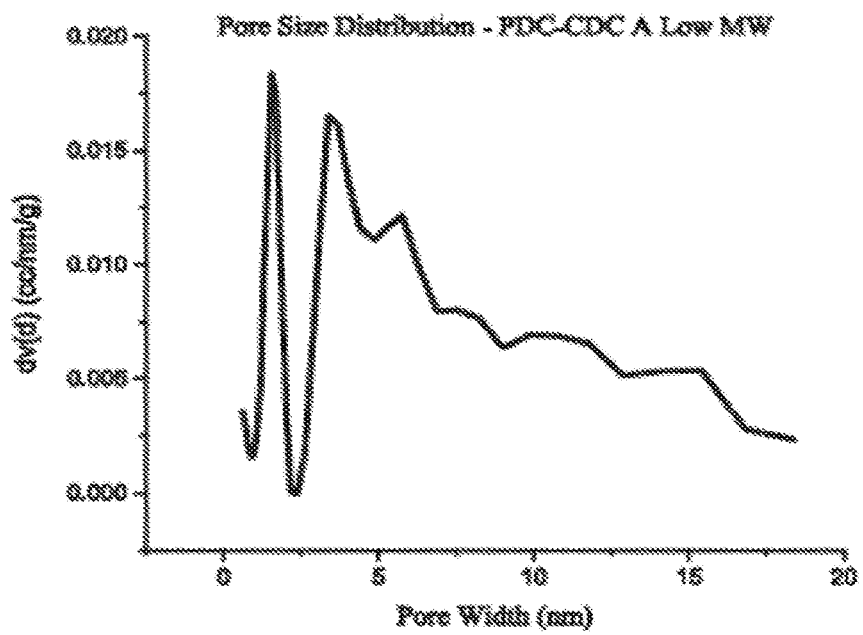
FIG. 1B shows the pore size distribution for carbide derived carbon materials PDC-CDC A Low MW.
Figure 1C:
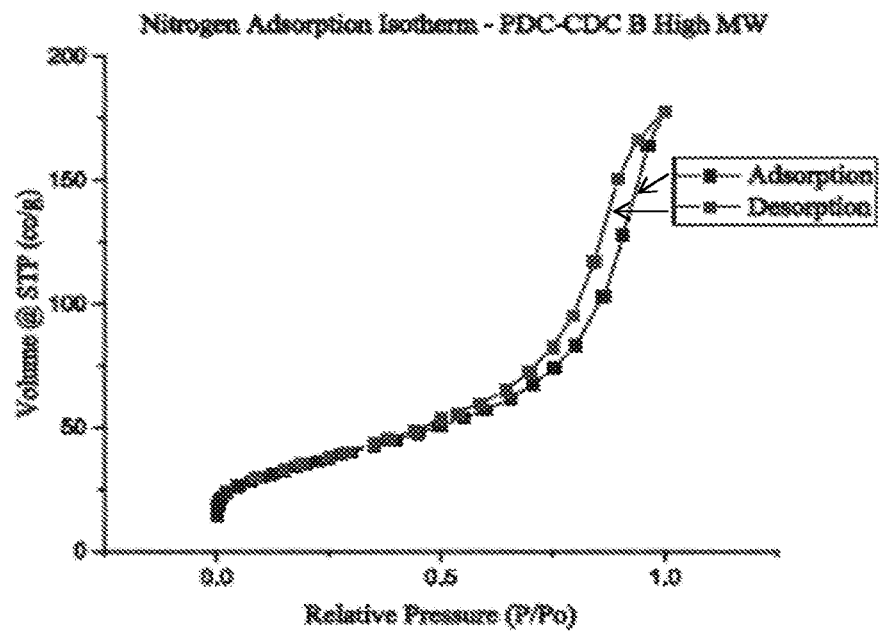
FIG. 1C shows the nitrogen adsorption isotherms for PDC-CDC B High MW.
Figure 1D:
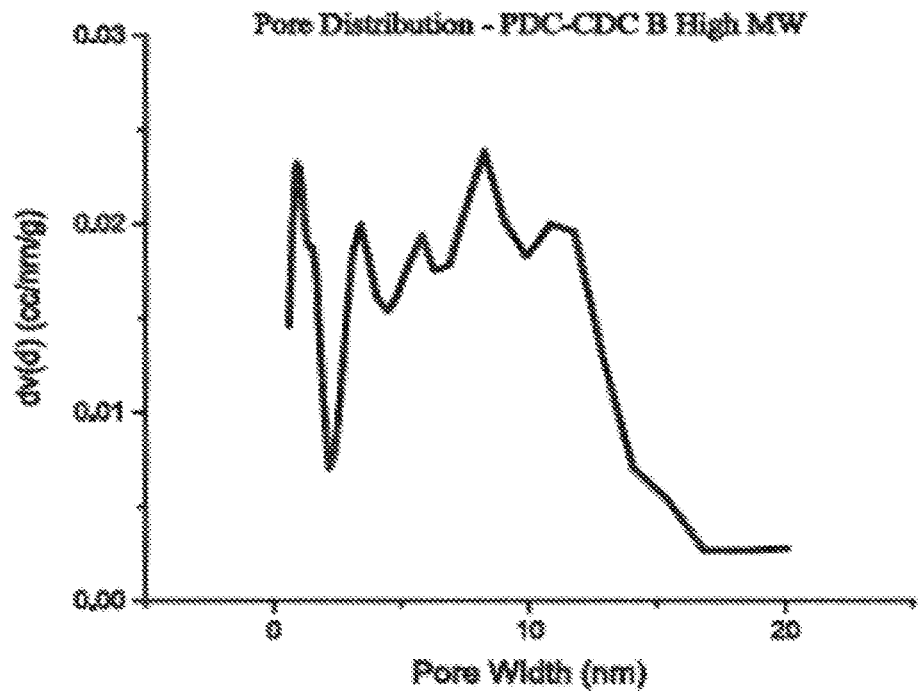
FIG. 1D shows the pore size distribution for carbide derived carbon materials PDC-CDC B High MW.

PDC-CDC:

FIGS. 1A and 1C shows the nitrogen adsorption isotherms for PDC-CDC A Low MW (FIG. 1A), and PDC-CDC B High MW (FIG. 1C). The nitrogen adsorption isotherms seen in PDC-CDC A Low MW, and PDC-CDC B High MW are indicative of a type iv isotherm. A type iv isotherm has the unique characteristic of a hysteresis, which is due to capillary condensation in larger pores such as mesopores. PDC-CDC materials have a broad mesoporous pore size distribution, with a mode pore width ranging from 1.54 to 8.23 nm. FIGS. 1B and 1D show the pore size distribution for PDC-CDC A Low MW (FIG. 1B), and PDC-CDC B High MW (FIG. 1D).

Figure 2A:
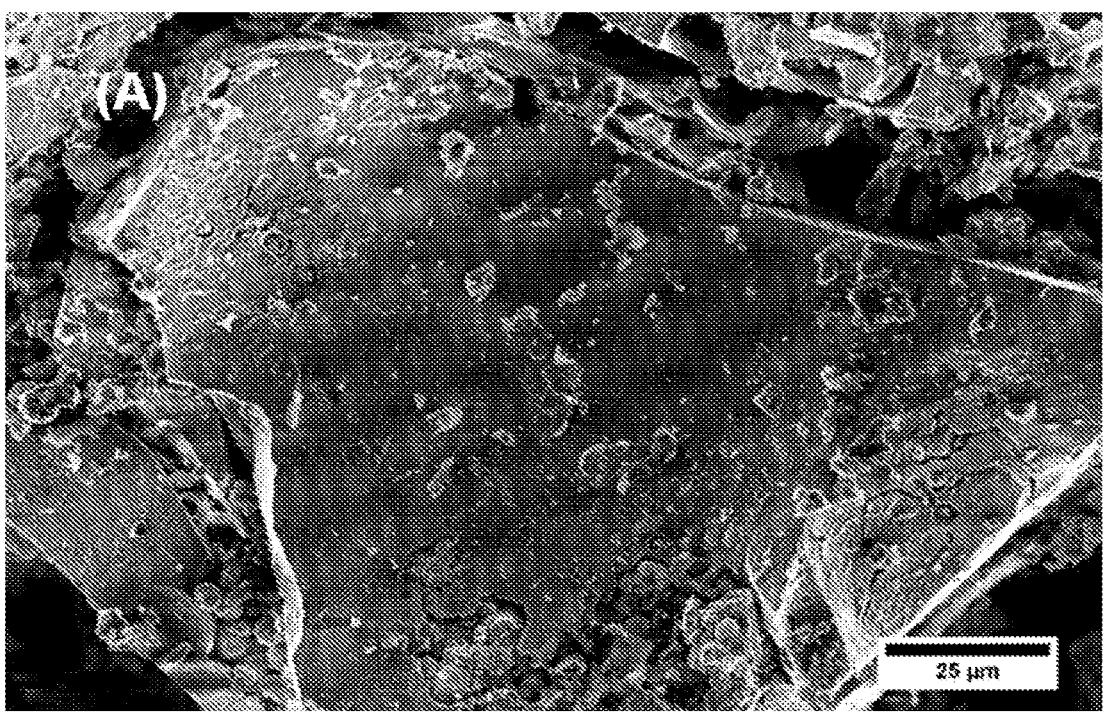
FIGS. 2A and 2B show SEM images of PDC-CDC A Low MW (FIG. 2A) and PDC-CDC B High MW (FIG. 2B) high MW precursor.
Figure 2B:
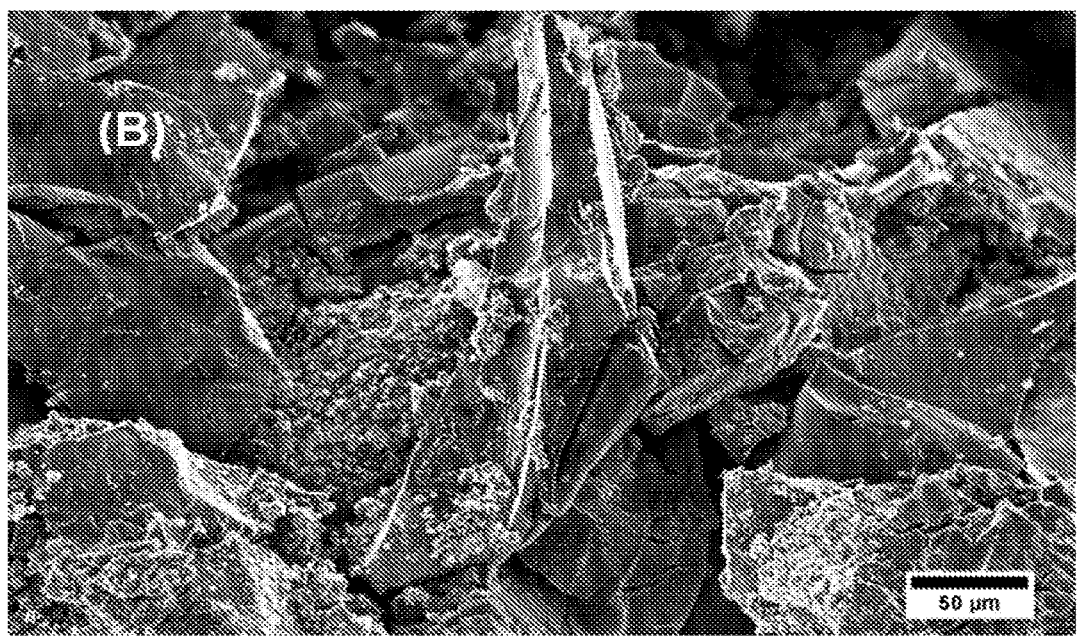

SEM images of both variations of PDC-CDC are in shown in current FIGS. 2A and 2B.

The surface area and particle size analysis data for PDC-CDC A Low MW, and PDC-CDC B High MW are shown in Table 1.

Figure 3:
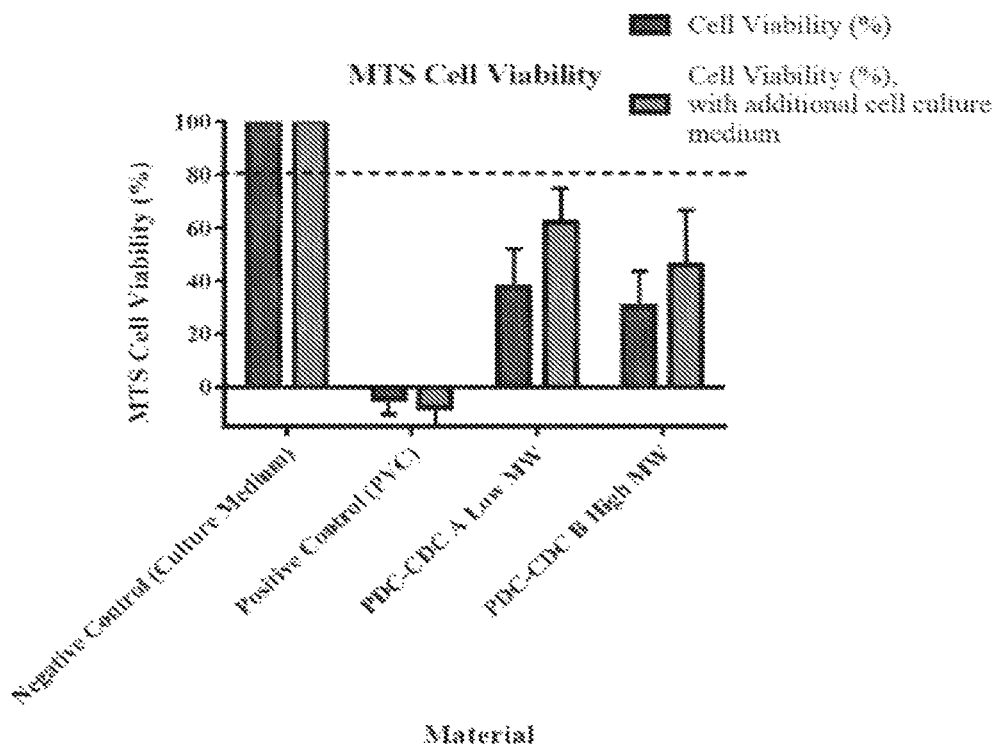
FIG. 3 shows cell viability for PDC-CDC A Low MW and PDC-CDC B High MW.

FIG. 3 shows cell cytotoxicity data for the PDC-CDC materials. From values around 40%, the cell viability increased to ~50% after additional cell culture medium was added. This is an indication that the powder may have prevented nutrients from the medium to reach the cells, and is from the powder's high density or adsorption of nutrients. The PDC-CDC materials are much more viable for cells relative the cytotoxic PVC polymer, but are cytotoxic to the HepG2 cells if an arbitrarily defined 80% cell viability level is used to regard a material as not cytotoxic.

Figure 4A:
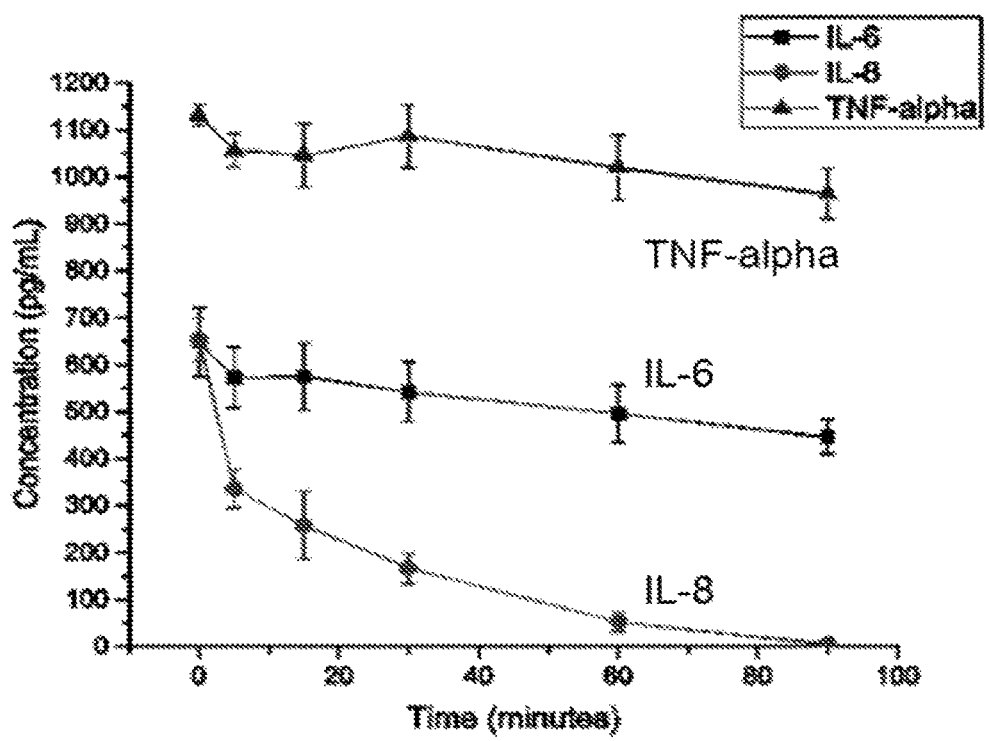
FIGS. 4A and 4B on shows cytokine adsorption on (FIG. 4A) PDC-CDC A Low MW and (FIG. 4B) PDC-CDC B High MW.
Figure 4B:
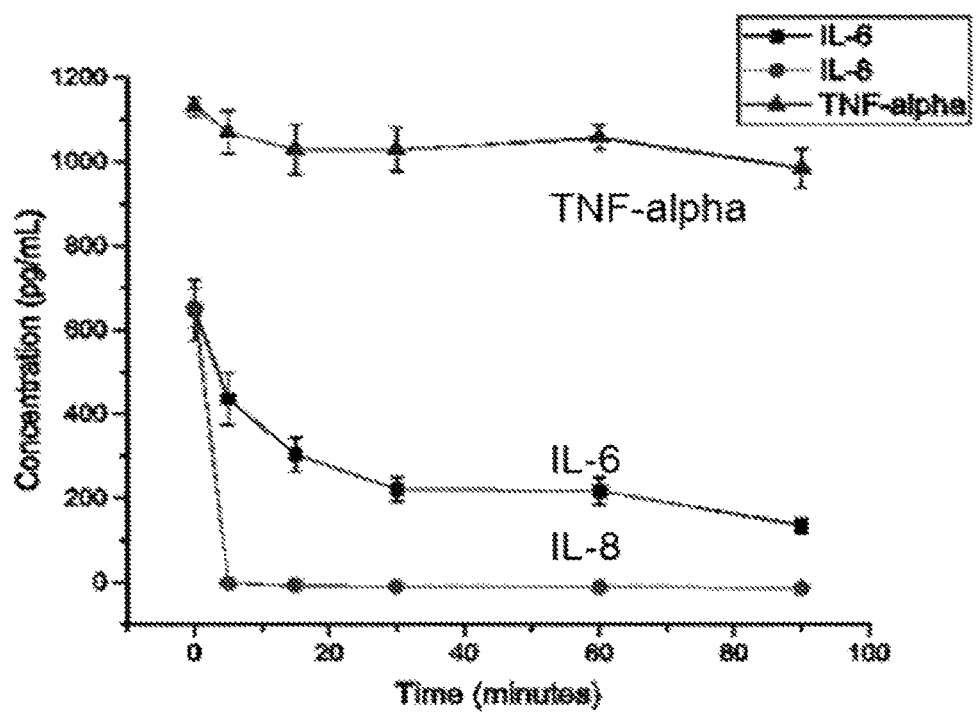
Figure 4C:
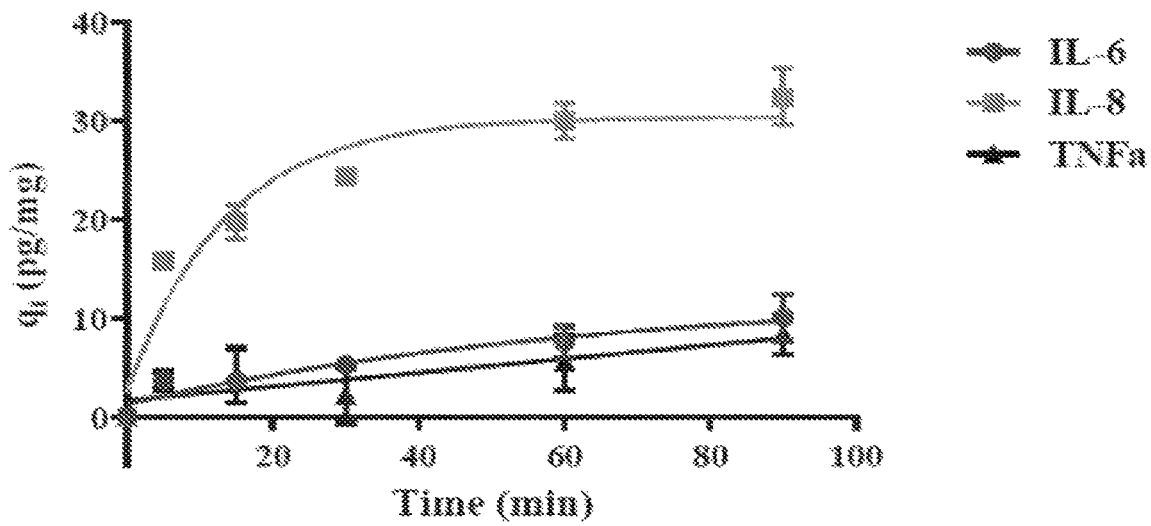
FIGS. 4C and 4D show normalized adsorption on (FIG. 4C) PDC-CDC A Low MW and (FIG. 4D) PDC-CDC B High MW.
Figure 4D:
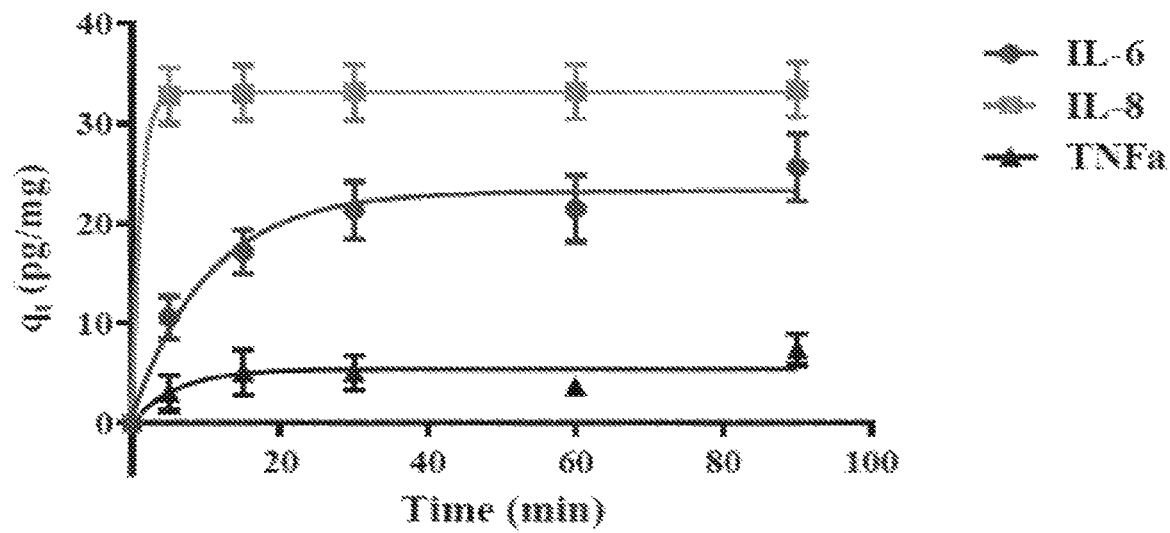
Figure 5A:
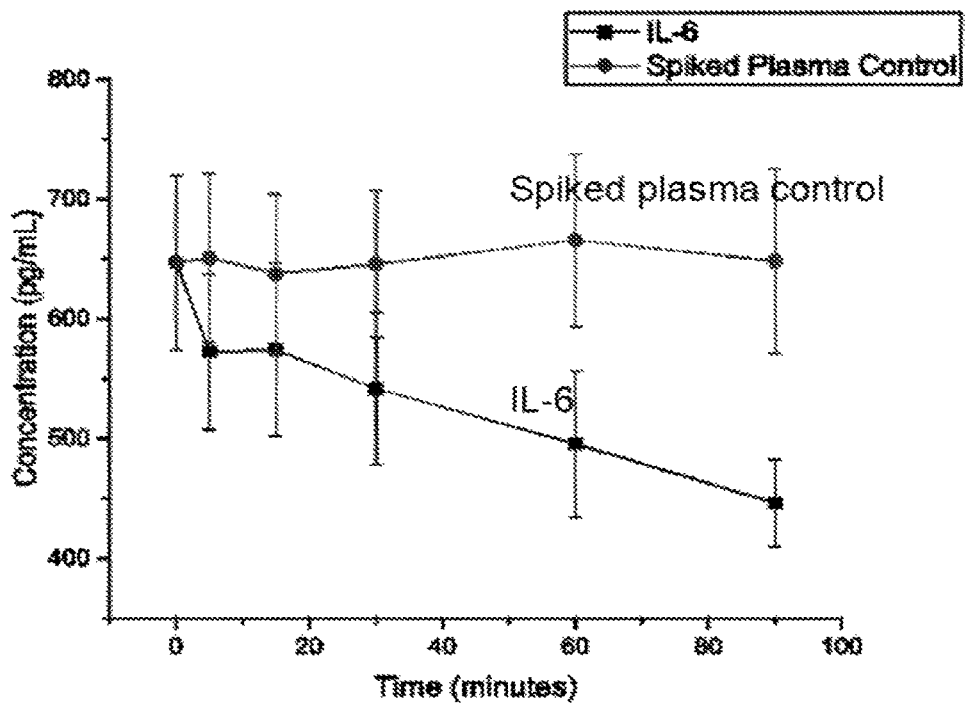
FIGS. 5A-5F illustrate cytokine adsorption of (FIGS. 5A-C) PDC-CDC A Low MW and (FIGS. 5D-F) PDC-CDC B High MW. When the excessive concentrations of proteins are added to the blood plasma for testing, it is considered "spiked plasma." The control is the protein concentration of this spiked blood plasma, but without contact with the material. This remains relatively constant, so no external factors are contributing to the decrease in concentration when the blood plasma is in contact with the material.
Figure 5B:
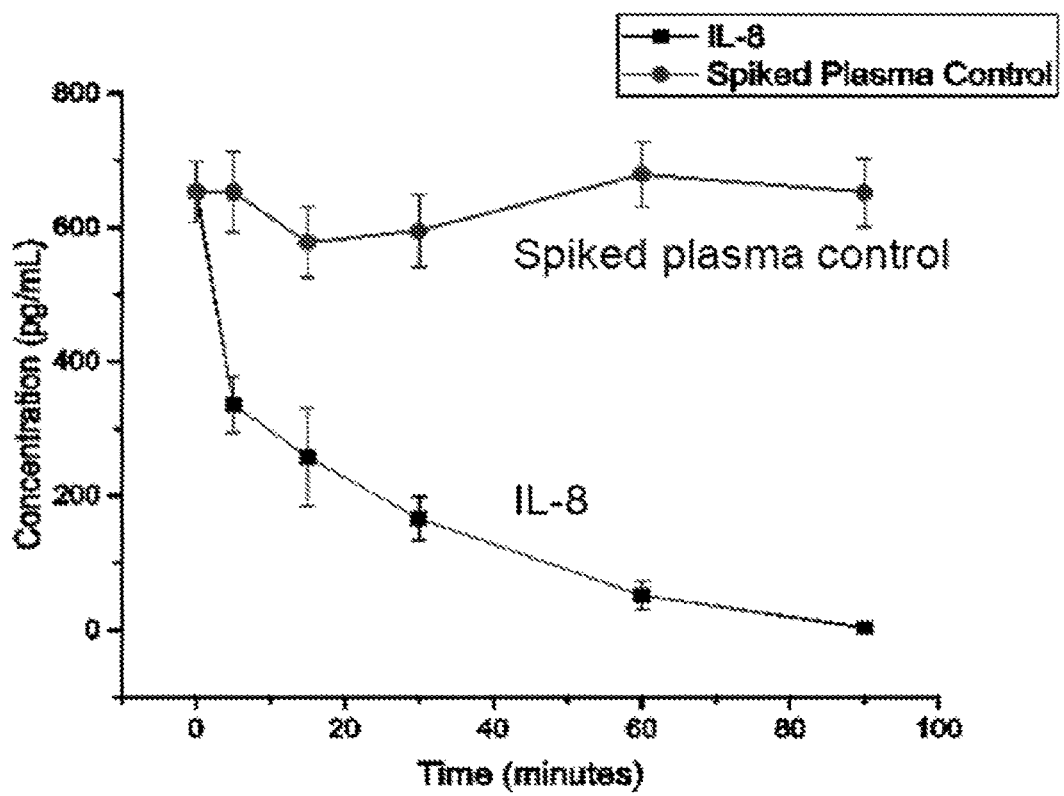
Figure 5C:
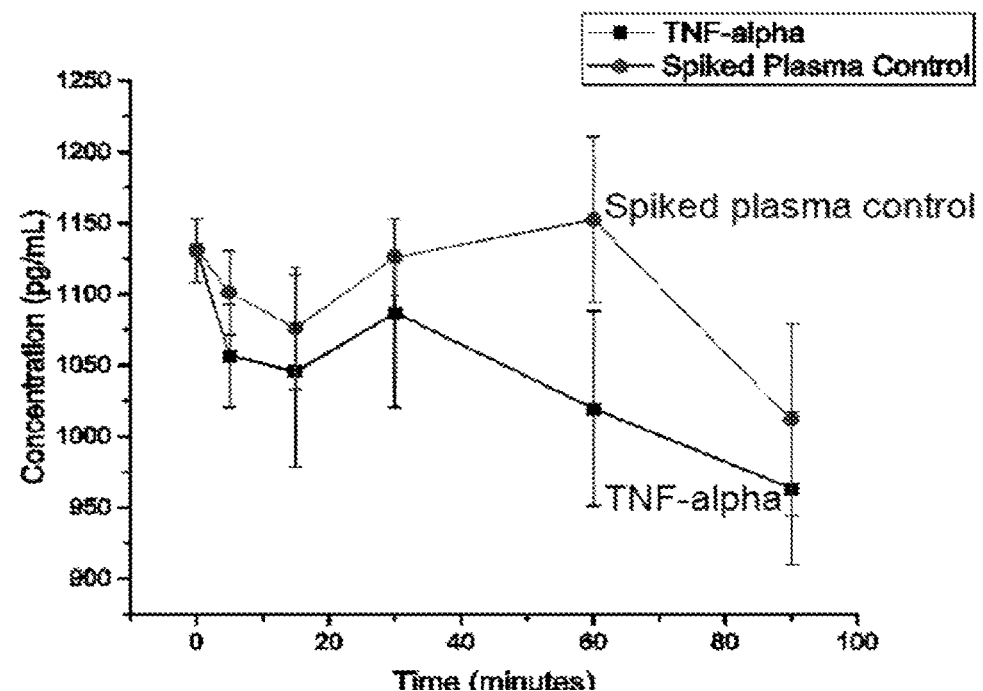
Figure 5D:
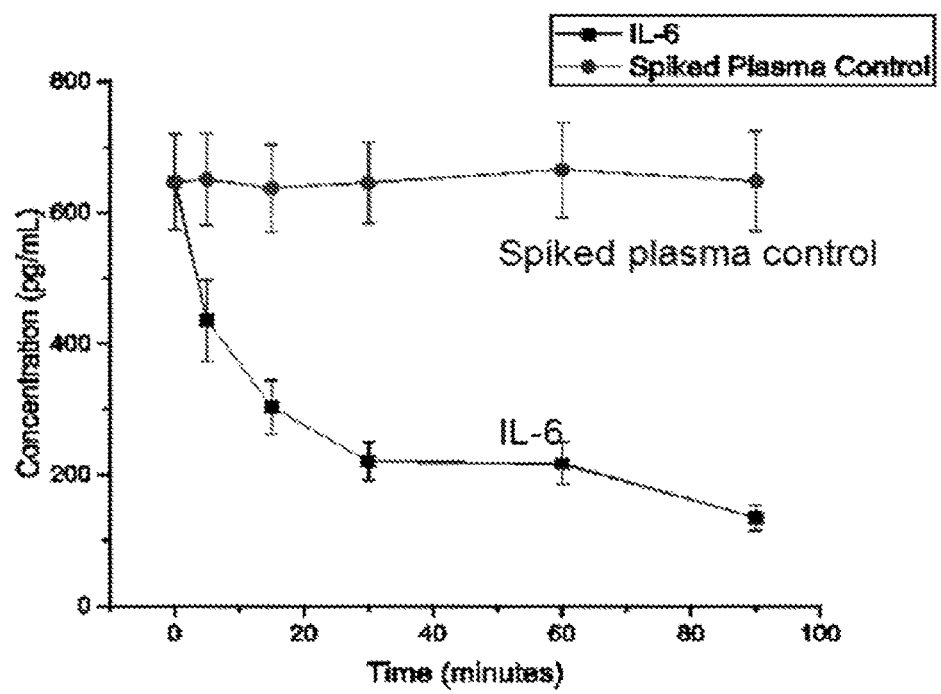
Figure 5E:
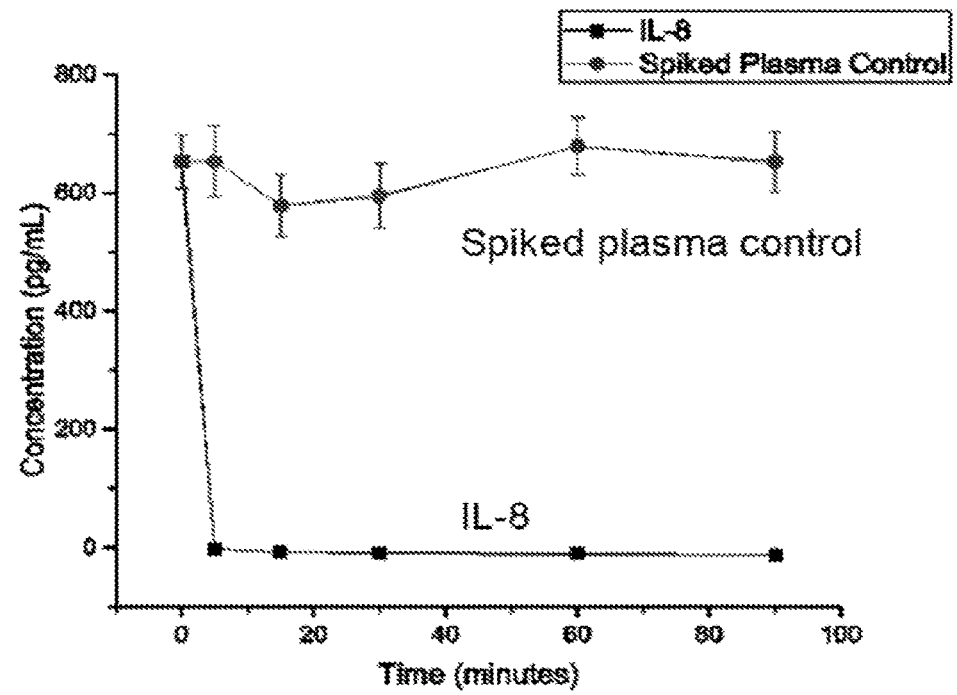
Figure 5F:
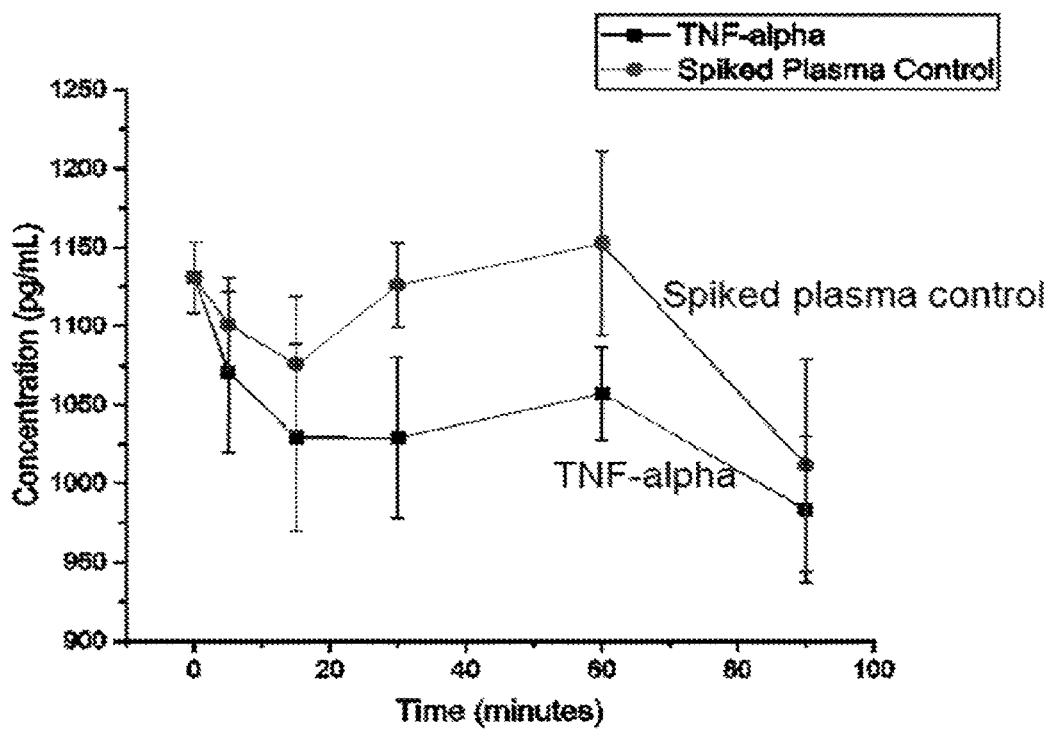
Figure 6A:
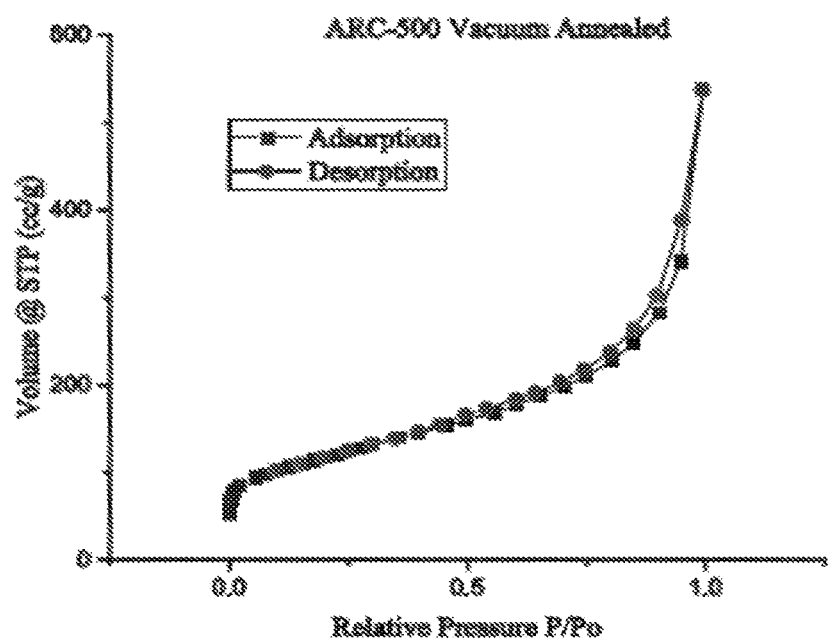
FIGS. 6A-6F show the nitrogen adsorption performance for six different GNPs: ARC-500 vacuum annealed (FIG. 6A); ARC-500 vacuum annealed, acid oxidized (FIG. 6B); ARC-500 vacuum annealed, air oxidized, aminated (FIG. 6C); ARC-750 (FIG. 6D); ARC-500 (FIG. 6E); ARC-300 (FIG. 6F).
Figure 6B:
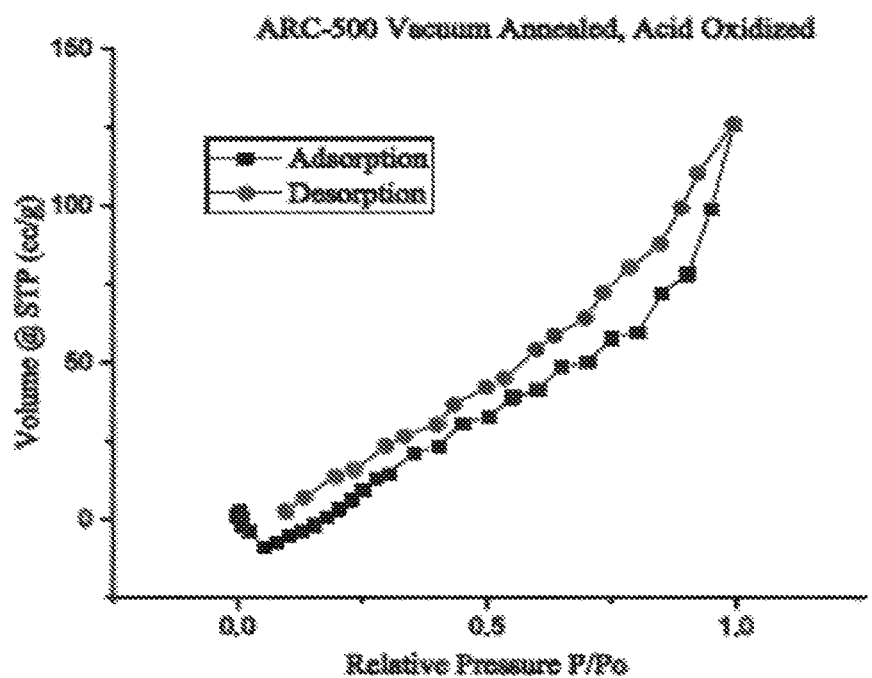
Figure 6C:
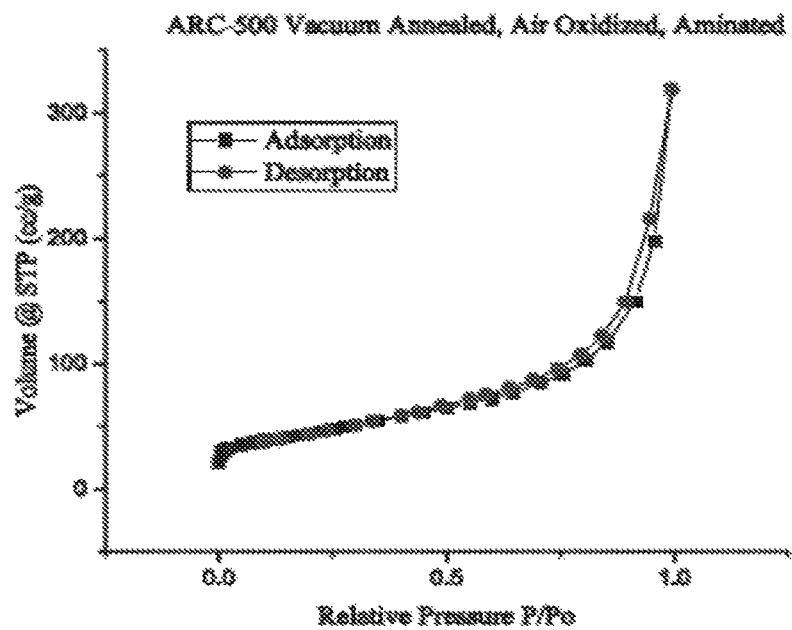
Figure 6D:
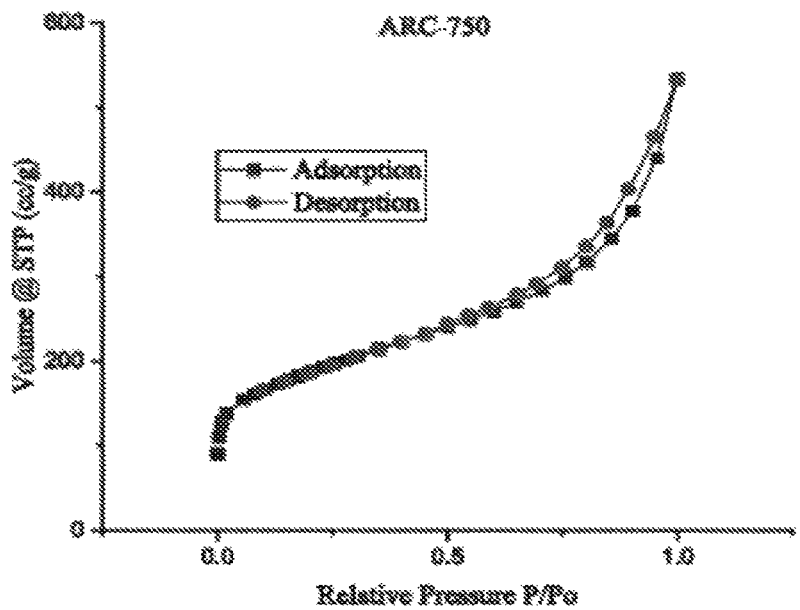
Figure 6E:
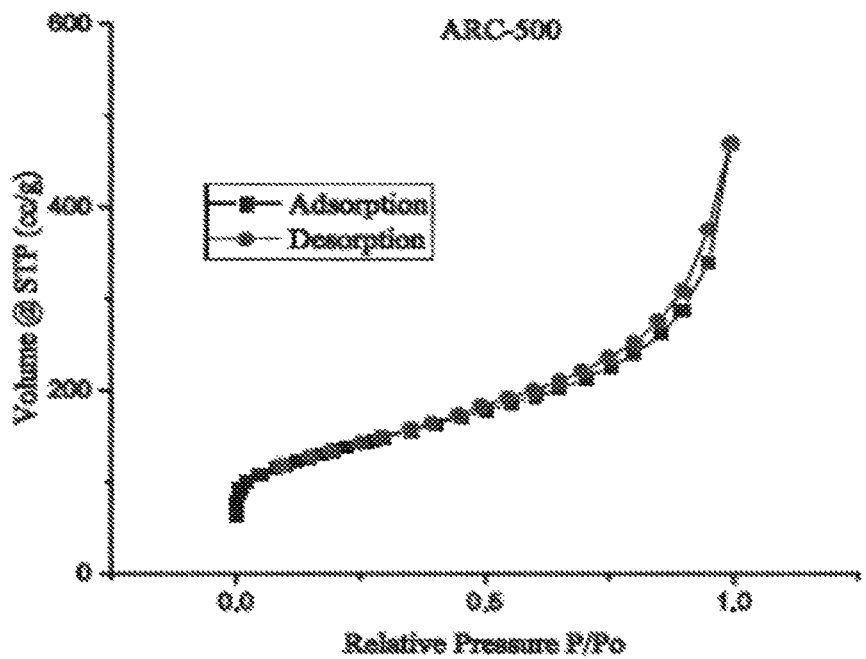
Figure 6F:
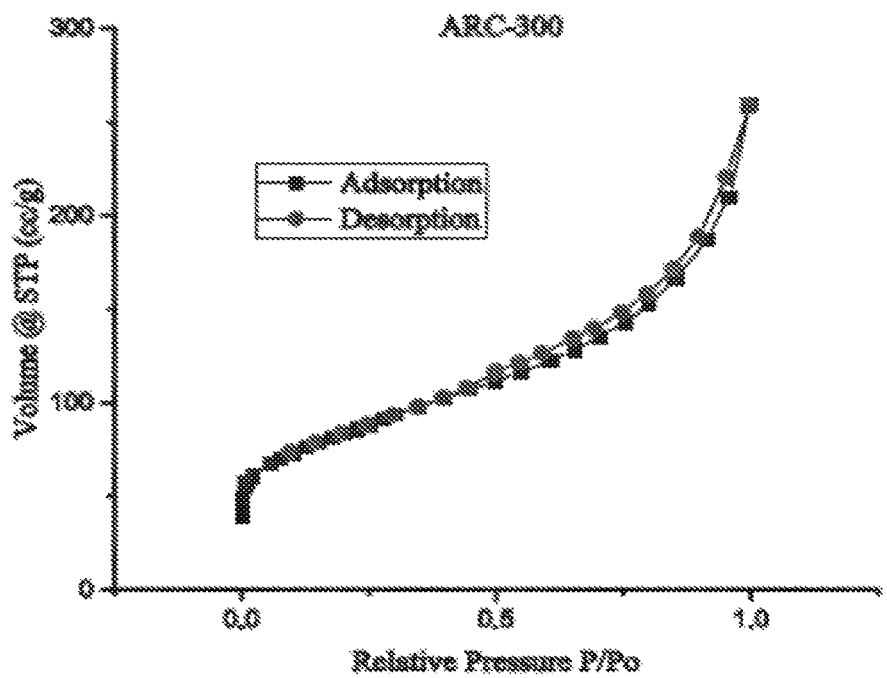

FIGS. 4A-4D show the adsorption of cytokines by PDC-CDC A Low MW, and PDC-CDC B High MW. Within a 95% confidence interval, controls were not statistically different between all-time points. A breakdown of the values for the exponential decay and pseudo second order equations are in Tables 3-8, and FIGS. 4C and 4D show the values of concentration versus time and normalized adsorption per mass for the polymer-derived porous carbons. Tables 3-5 displays the exponential decay variables for the normalized adsorption. Errors bars are displayed as plus or minus the standard error of mean. Overall, mesoporous PDC-CDC carbons saw a gradual decrease in cytokine concentration over the adsorption study. A clear trend was observed for adsorption capacity with respect to protein size. The largest protein, TNF-α, saw the lowest normalized adsorption capacity, qt (mass of cytokine adsorbed per unit mass of adsorbent), while IL-8 had the largest qt. Both materials were able to remove IL-8 concentrations to negligible levels. Ho and McKay's pseudo second order model fit the best for the PDC-CDC materials, fitting to the normalized adsorption qt of each cytokine with an $R^2$ value of ≥0.9. See Tables 6-8.

FIGS. 5A-5F shows adsorption of individual cytokines including their respective positive controls.

Graphene Nanoplatelets (GNPs):

FIGS. 6A-6F show the nitrogen adsorption performance for six different GNPs: ARC-500 vacuum annealed (6A); ARC-500 vacuum annealed, acid oxidized (6B); ARC-500 vacuum annealed, air oxidized, aminated (4C); ARC-750 (6D); ARC-500 (6E); ARC-300 (6F). Most of the isotherms are indicative Type II or nonporous isotherms. The vacuum annealed C-500, ARC-500, and ARC-750 have the highest adsorption of nitrogen.

Figure 7:
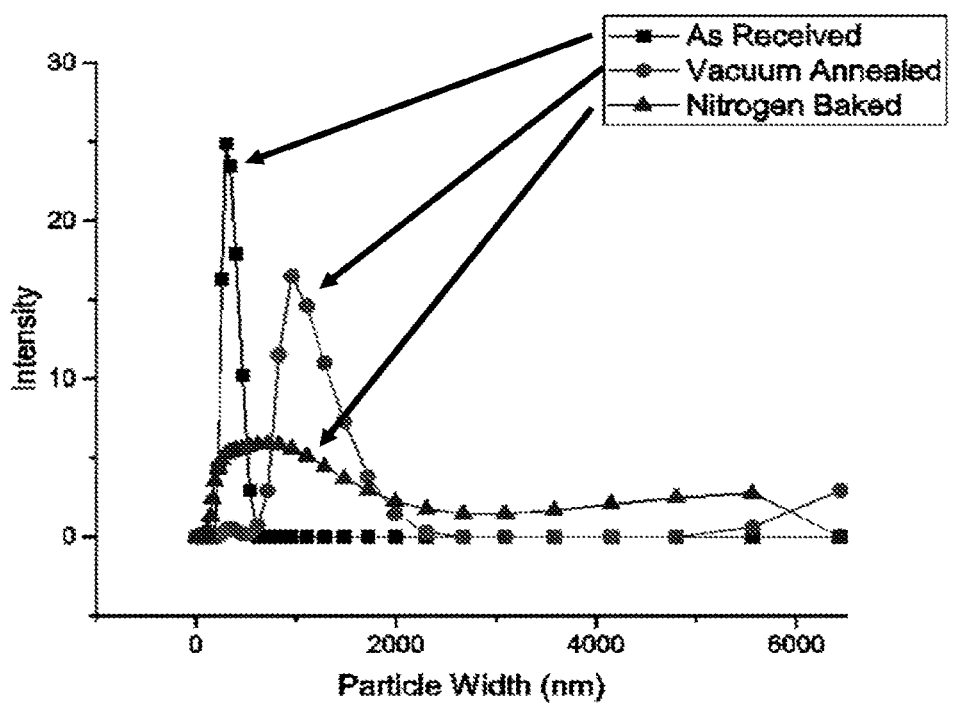
FIG. 7 shows particle size distributions of GNP.

Materials characterization was primarily completed on nanoplatelets, due to their excellent adsorption efficiency. Particle size distribution data for several GNPs is shown in FIG. 7. An effect on particle size and surface area is observed between the as received GNP and nitrogen baked GNP. This decrease in average particle size has increased the specific surface area (SSA), allowing for larger number of sites for adsorption. Table 1 displays surface area data of all materials from nitrogen adsorption experiments, based on BET and QSDFT calculations.

Figure 8A:
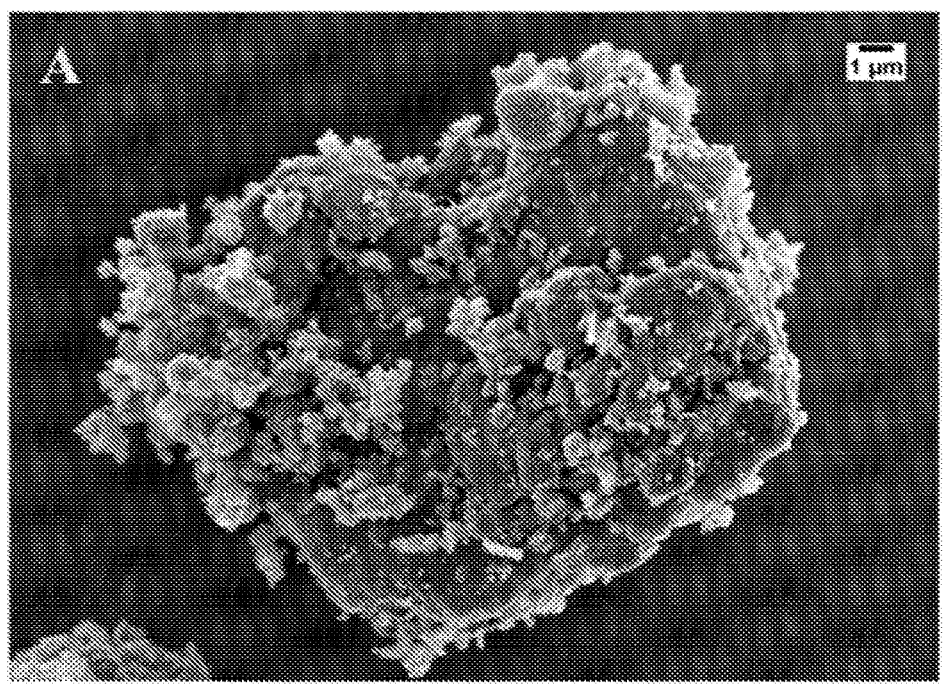
FIGS. 8(A-D) shows SEM and TEM images of graphene nanoplatelet agglomerates (FIGS. 8A, 8C), which are made of submicron sized particles (FIG. 8B), while a single graphene nanoplatelet particle consists of stacks of graphene layers seen under TEM imaging (FIG. 8D).
FIG. 8E shows a TEM image of a cross section of a GNP. This unique structure enables the large surface of the GNP to be exposed for cytokine adsorption, as represented in FIG. 8F.
FIG. 8G shows schematic representations of the protein adsorption process, with the porous material on the left (carbide derived carbons) and the nonporous material (graphene nanoplatelets) on the right.
Figure 8B:
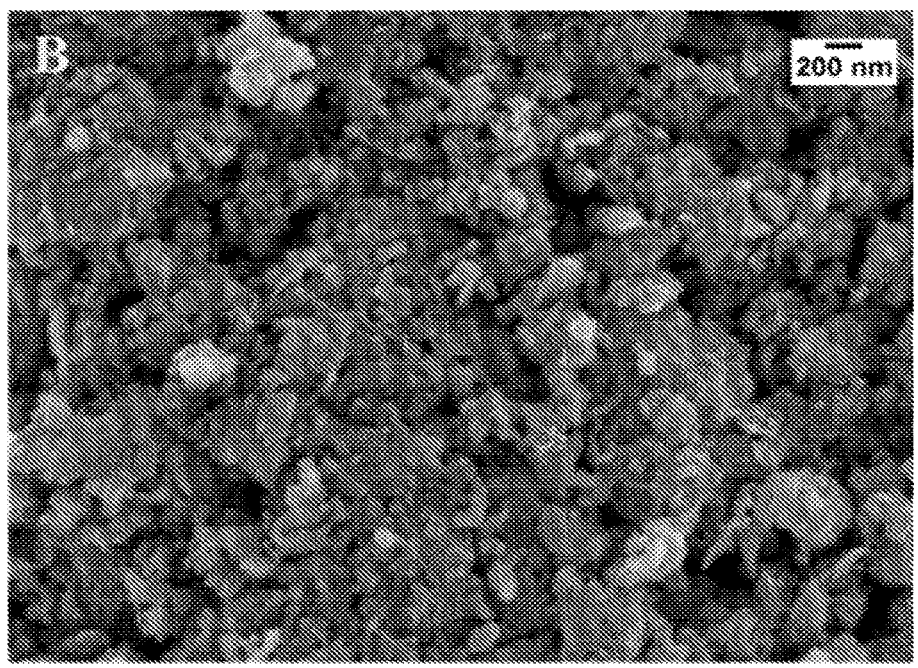
Figure 8C:
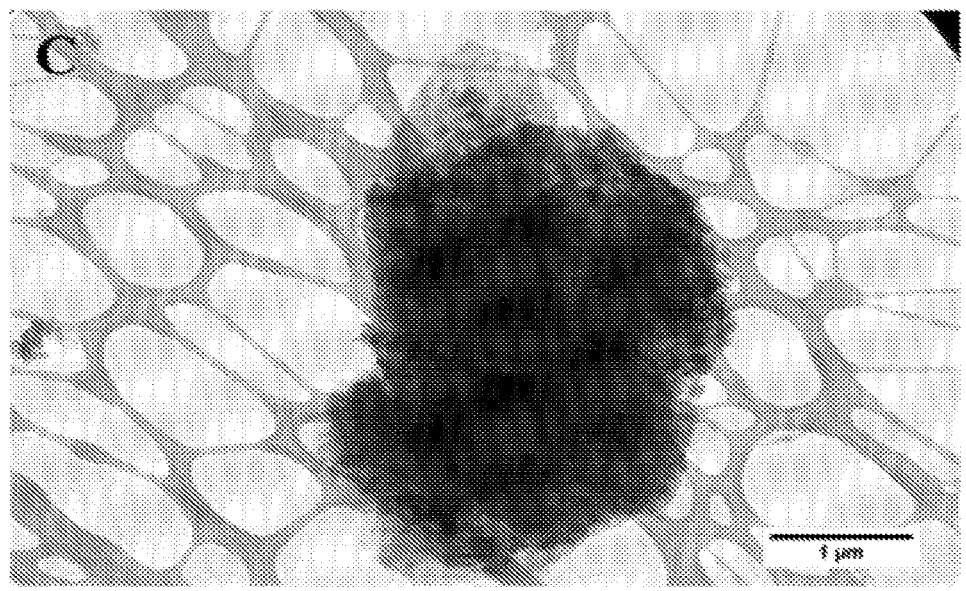
Figure 8D:
Figure 8E:
Figure 8F:
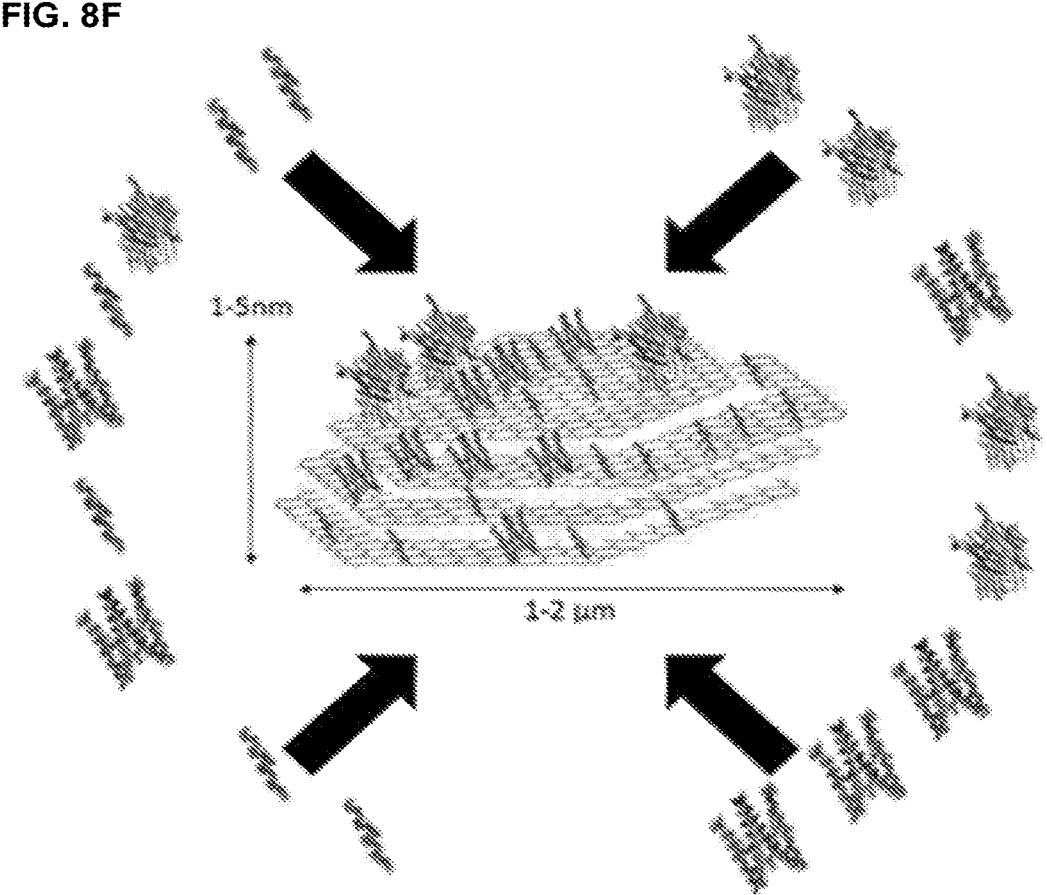
Figure 8G:
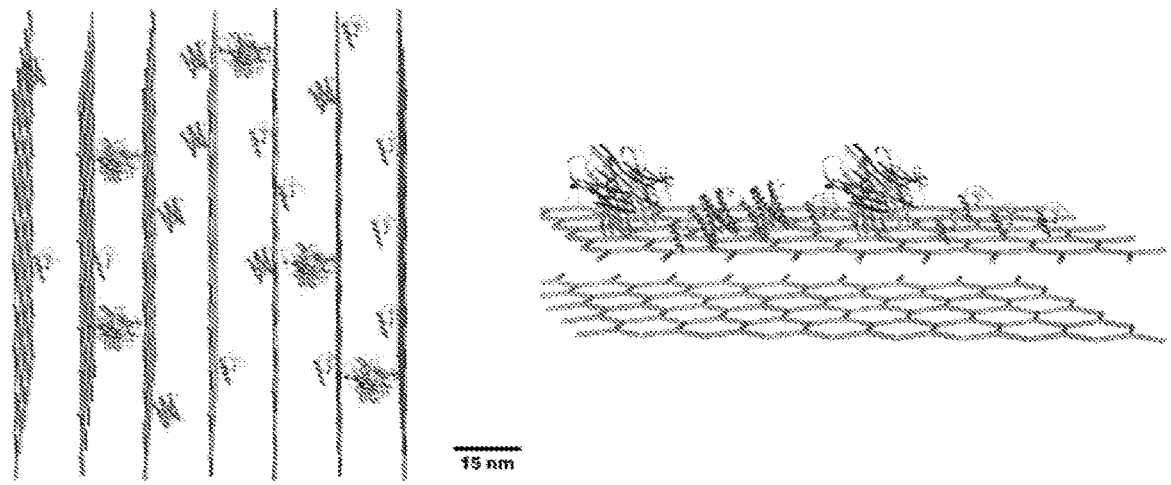

Loose agglomerates of GNP can be observed under SEM (FIG. 8A); at a higher magnification SEM image revealed that this agglomerate consisted of submicron size particles (FIG. 8B). After sonication using ethanol as a solvent, smaller agglomerates of GNP were observed under TEM (FIG. 8C), revealing its multi-layer-stacked graphene structure. Under higher magnification of TEM images, a single nanoplatelet can be observed from a top-down perspective (FIG. 8D). FIG. 8E is a TEM image of a cross section of a GNP.

Figure 9A:
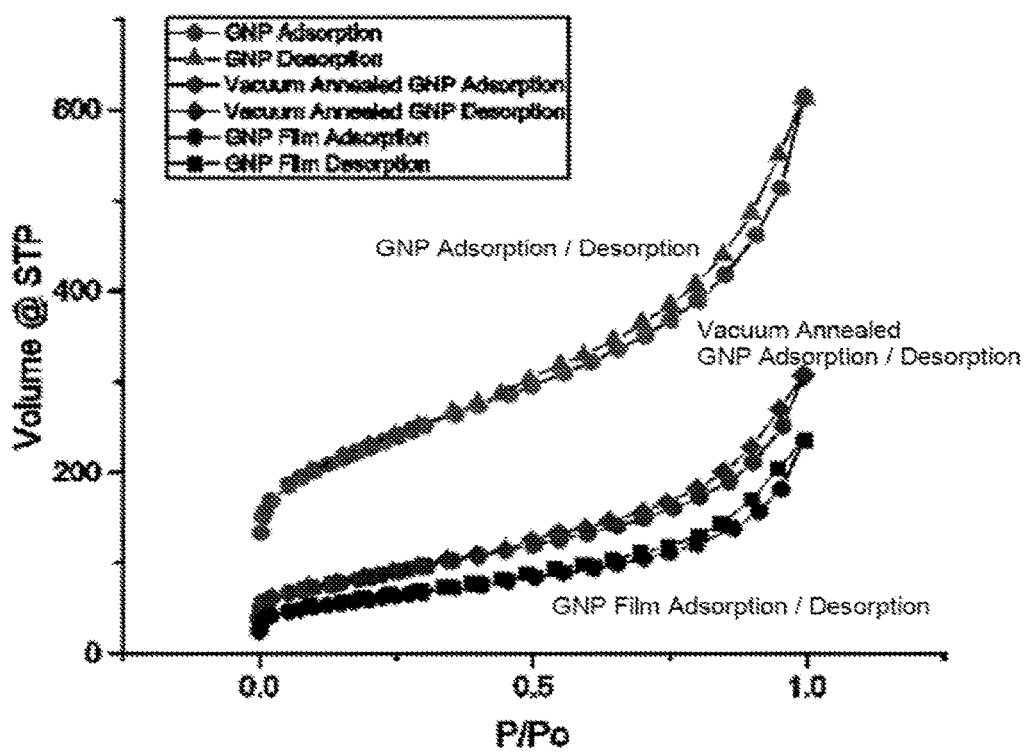
FIGS. 9(A-B) shows nitrogen adsorption isotherms (FIG. 9A) and pore size distribution (FIG. 9B) of the graphene nanoplatelet (GNP), vacuum annealed graphene nanoplatelet (VA-GNP) and graphene nanoplatelet polytetrafluoroethylene composite film (GNP-PTFE).
Figure 9B:
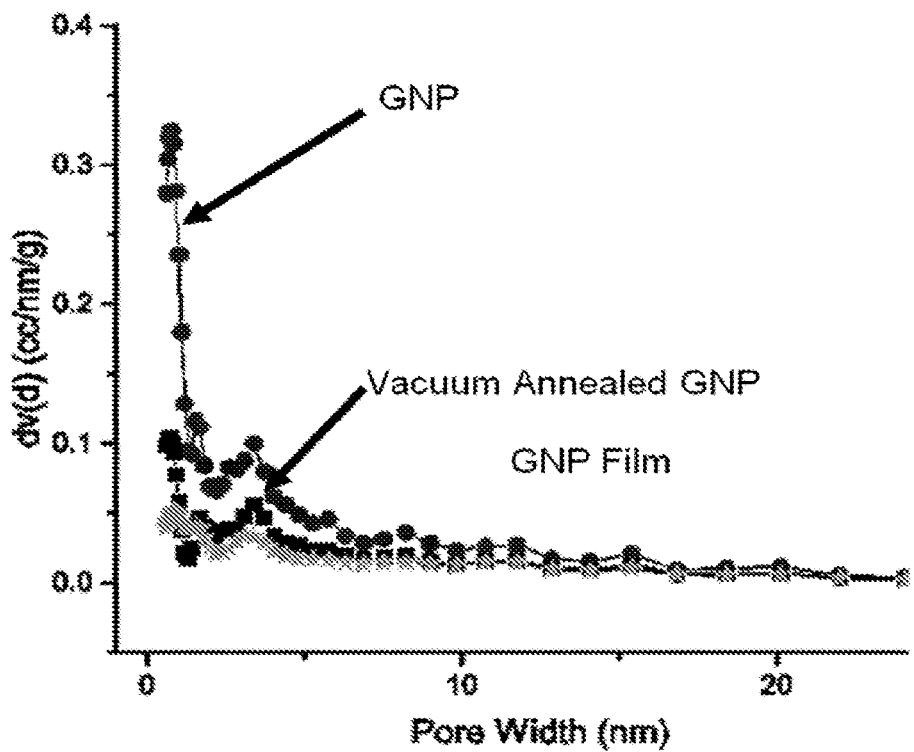

The adsorption isotherms of GNP, vacuum annealed GNP, and GNP PTFE film exhibit a rapid increase of adsorbed nitrogen volume at the low $P/P_o$ region and are all of a type II nonporous isotherms, as shown in FIG. 9A. QSDFT was utilized with the assumption of slit-shaped pores to estimate the pore size distribution, given the graphitic nature of the material (FIG. 9B & Table 1). GNP exhibits a specific surface area as high as 797.4 $m^2/g$ determined by nitrogen adsorption and the Brunauer-Emmett-Teller equation (Table 2). The materials tested in the mesoporous category ranged from pore sizes of 2 nanometers to about 20 nanometers. The macropores were confirmed by methods such as scanning electron microscopy. While the mode of the pore width in Table 2 is less than 1 nm, the mesopores are clearly seen in the pore size distributions in FIGS. 1B and 1D for the carbide derived carbon materials (PDC-CDC materials). These graphs are created using the density functional theory described above.

As shown in FIG. 9A, when GNP was vacuum annealed (VA-GNP), there is a 2.7-fold decrease in specific surface area and pore volume. This is observed along with a 3-fold increase in VA-GNP particle size determined by dynamic light scatter compared to the GNP. The increase in particle size and decrease in surface area is from the restacking of graphene planes during graphitization. SEM and TEM images which revealed a small particle size and tightly stacked graphene structure of the GNP, between graphene layers to prevent access of nitrogen molecules. The large specific surface of the GNP is attributed predominantly to its outer surface area. When VA-GNP was incorporated into the PTFE (GNP-PTFE) composite film, the composite film showed a slight reduction in adsorbed nitrogen volume and micropore volume (FIG. 9B), while the shape of isotherm and pore size distribution curve remained similar to the VA-GNP. The specific surface and micropore volume of the GNP-PTFE film remained as high as 210.4 $m^2/g$, and 0.30 $cm^3/g$ respectively and only slightly lower than the VA-GNP alone at 293.7 $m^2/g$ and 0.39 $cm^3/g$ (Table 2). This reduction in the specific surface area and micropore volume detected by the nitrogen adsorption analysis could be due to the addition of PTFE film, which is non-porous binder accounting for 5% of the total sample weight. The results indicated that the GNP surface area remained largely accessible by the nitrogen molecules after incorporation into the PTFE film.

Figure 10:
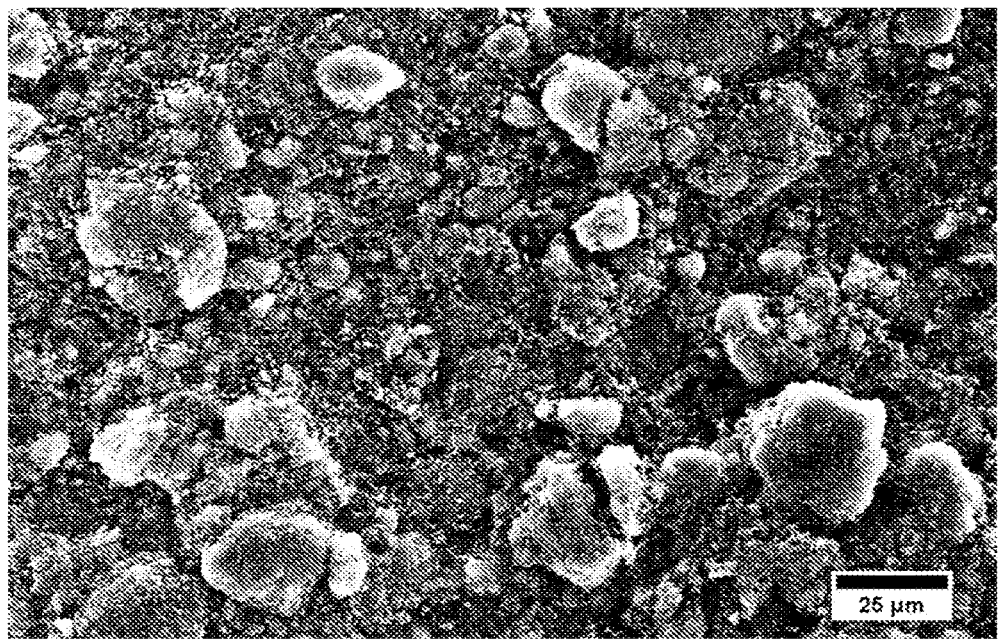
FIG. 10 shows an SEM image of GNP.

An SEM images of the GNP nanoplatelets are seen in FIG. 10.

Figure 11A:
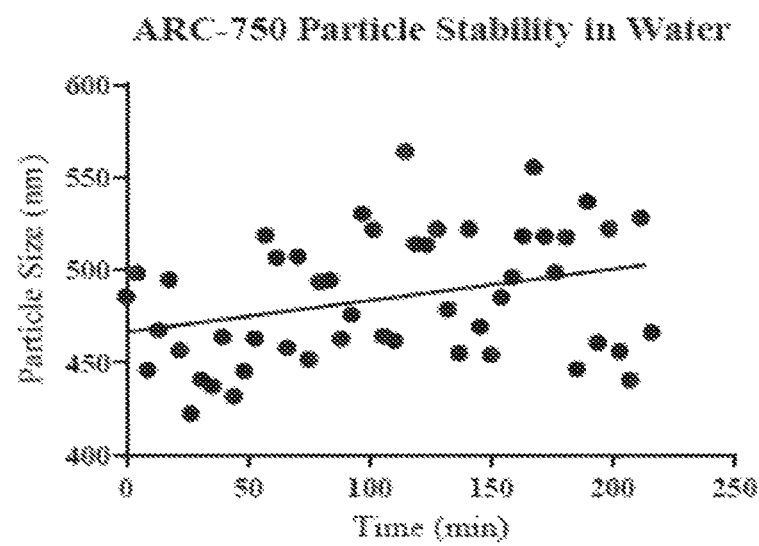
FIGS. 11A-11C show particle size stability for ARC-750 (FIG. 11A), ARC-500 (FIG. 11B), and ARC-300 (FIG. 11C).
Figure 11B:
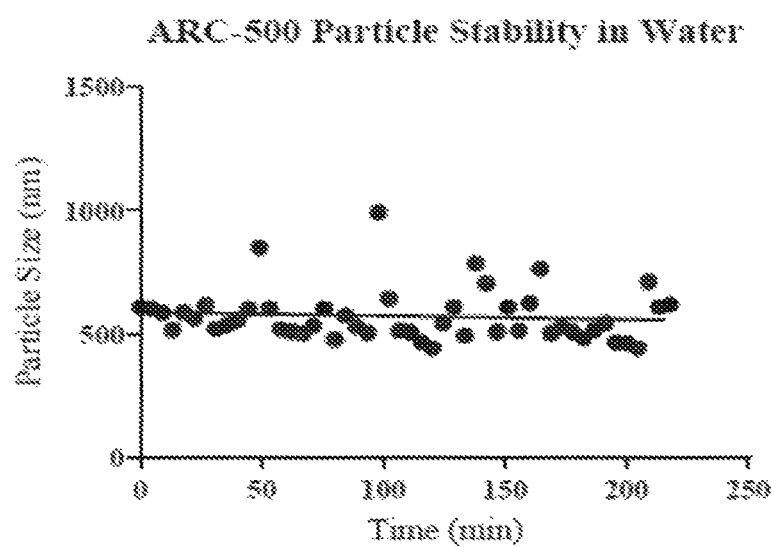
Figure 11C:
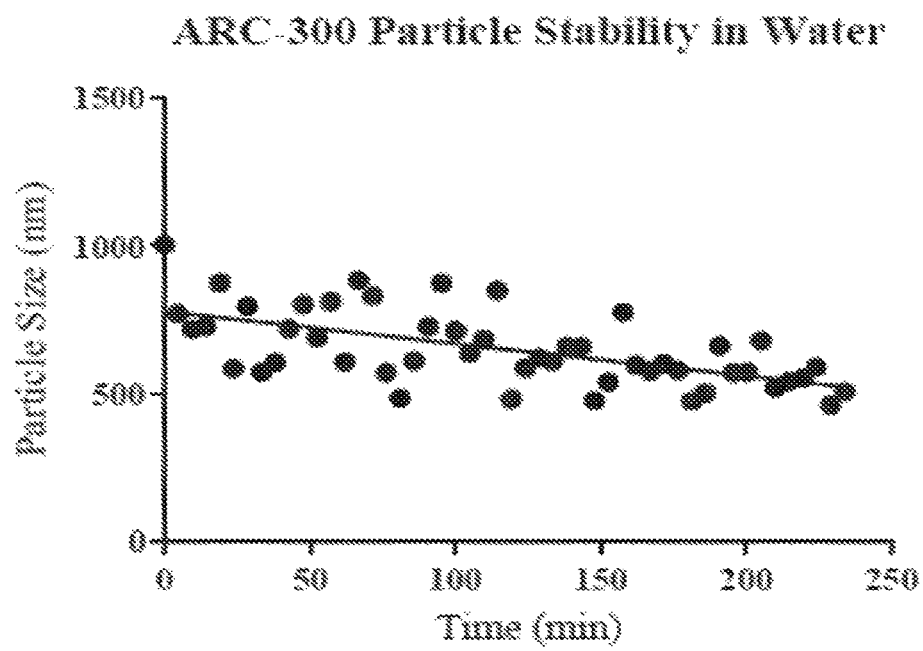
Figure 12A:
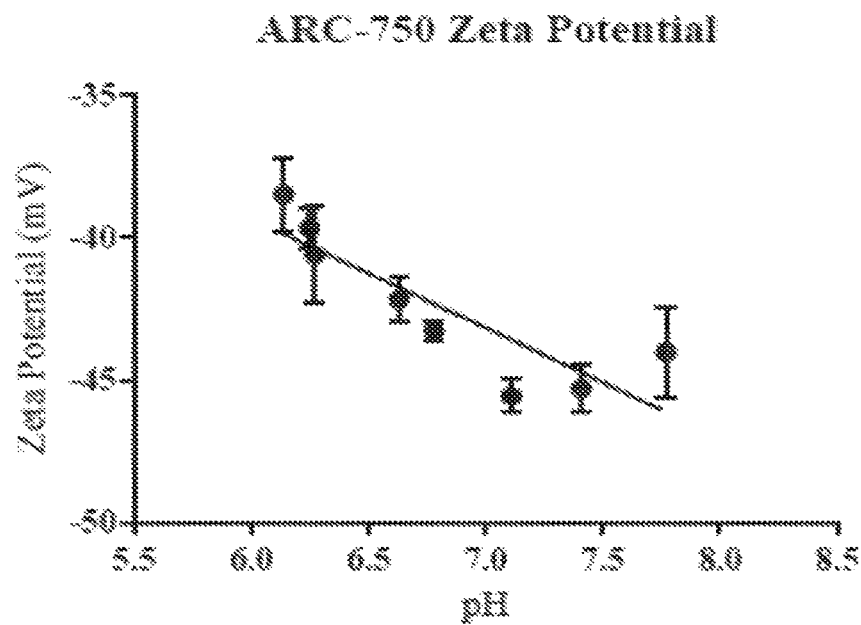
FIGS. 12A-12F show Zeta potential as a function of pH for ARC-500 vacuum annealed (FIG. 12D); ARC-500 vacuum annealed, acid oxidized (FIG. 12E); ARC-500 vacuum annealed, air oxidized, aminated (FIG. 12F); ARC-750 (FIG. 12A); ARC-500 (FIG. 12B); ARC-300 (FIG. 12C).
Figure 12B:
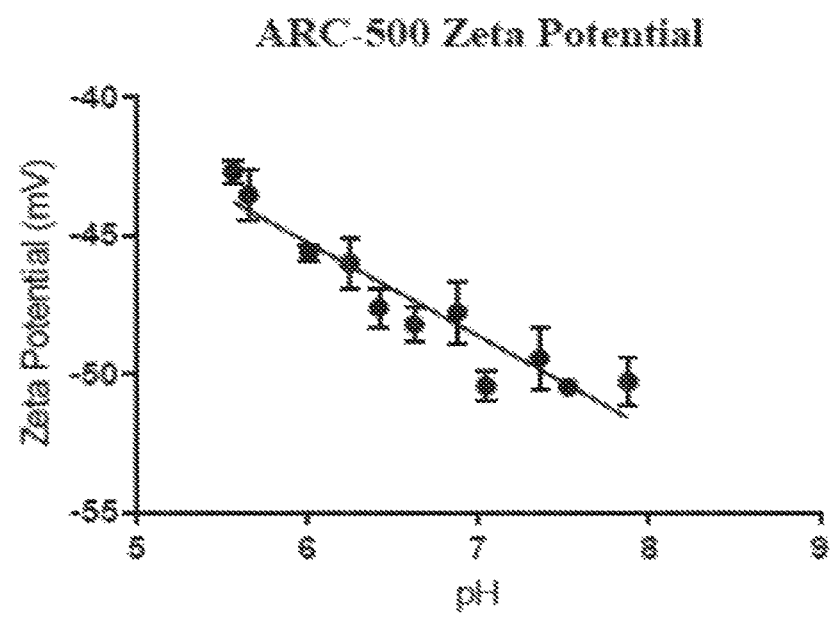
Figure 12C:
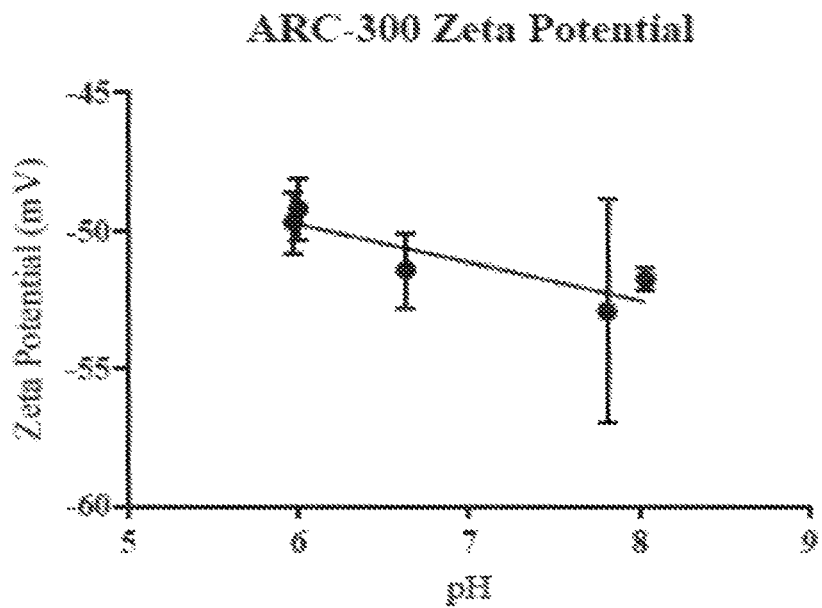
Figure 12D:
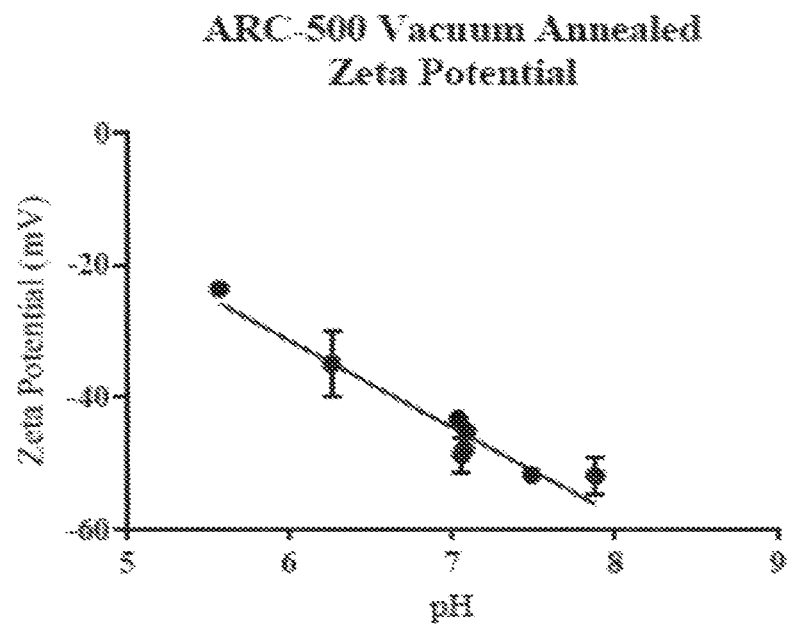
Figure 12E:
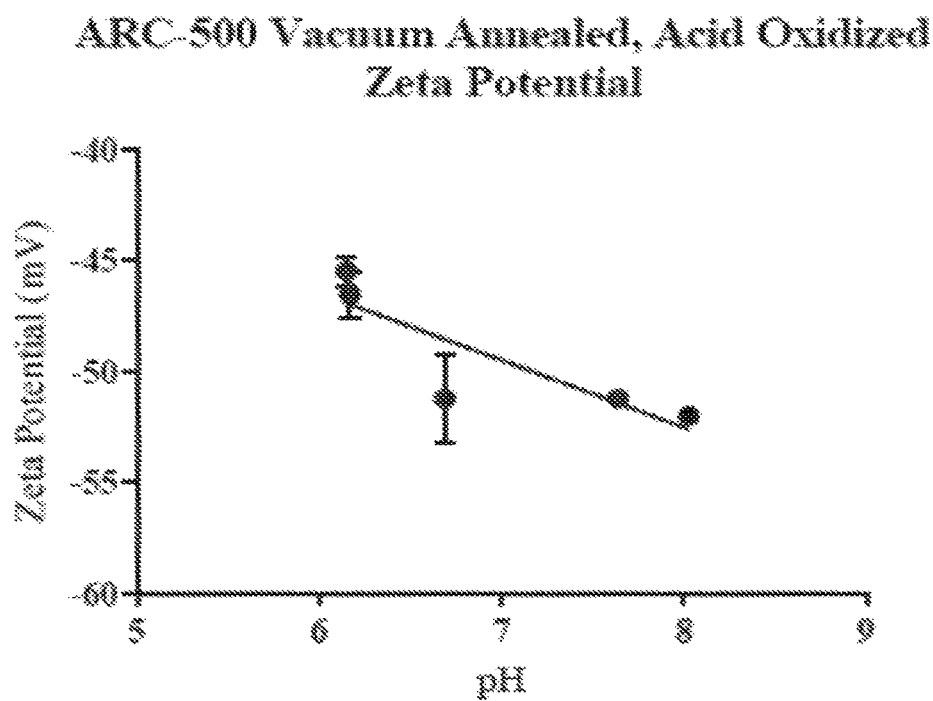
Figure 12F:
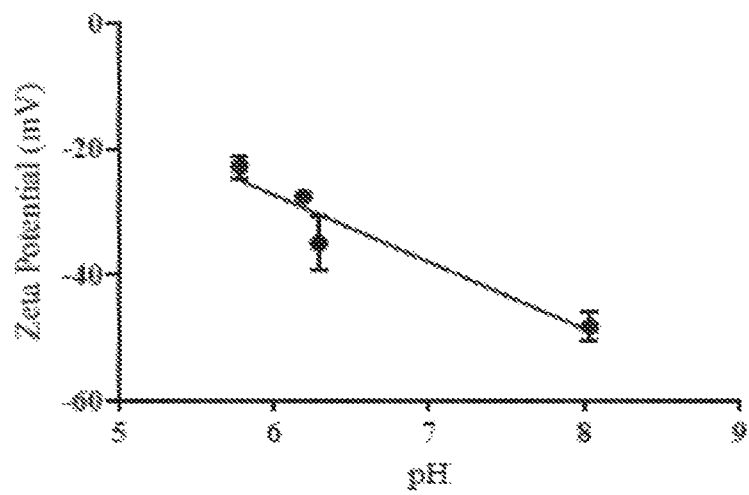

Particle size was measured as a function of time in FIGS. 11A-11C for the three different particle size GNP materials used. All materials relatively maintained their average particle size, but the most stable was the GNP with the smallest starting particle size, ARC-750. These particles agglomerated slightly over time and, after a critical agglomeration point, fell out of solution by gravitational force.

Zeta potential was measured with respect to pH for all variations of GNP and is displayed in FIGS. 12A-12F. The acid treated and ARC-500 samples appear to have the overall best colloidal stability. This is counterintuitive, as the hydrophobic nature of the vacuum annealed GNP should cause it immediately fall out of solution, while the acid oxidized and aminated samples should interact the most with water molecules and have the highest surface charge. It is worth noting that all of these samples have a very large zeta potential value at 7.4, the pH of blood. Therefore, they are expected to have a high colloidal stability in an aqueous environment, and maximal contact with proteins in solution.

Figure 13:
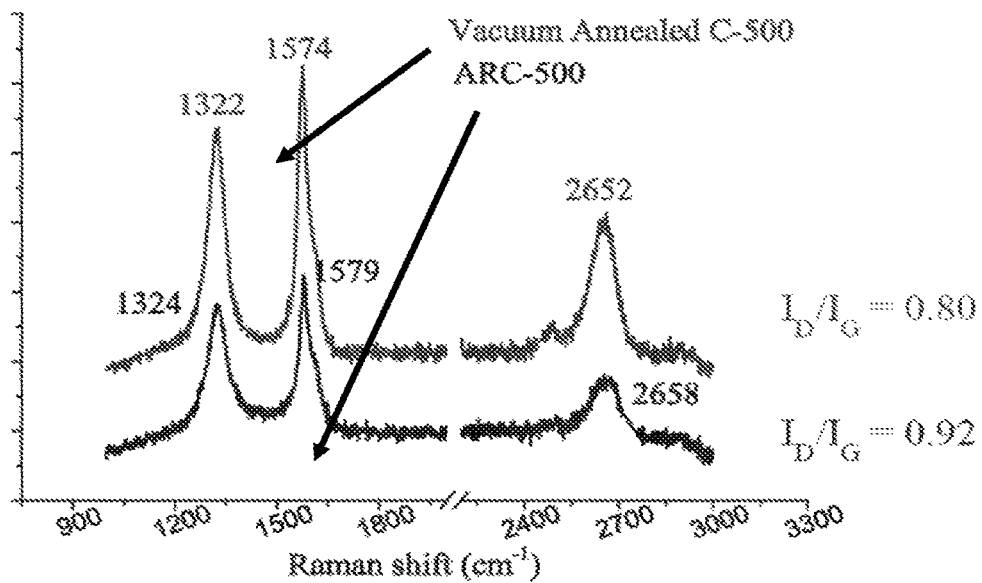
FIG. 13 shows Raman spectra and ID/IG ratios, or ratio of D and G band intensities for vacuum annealed C-500 and ARC-500.

FIG. 13 shows the Raman spectra for vacuum annealed and as-received C-500 GNP materials. The ratio of intensities between the D and G bands is indicative of the overall order in the material and, after vacuum annealing, this ratio decreases. The fitted positions of the G band indicate that they are close to the G2 peak, suggestive of ordered sp2 carbon. After annealing, this peak significantly increases in intensity and narrows in width. There is also an increase in intensity of the D band at 1322 cm-1, but this could be due to increasing particle size and the large amount of particle edges that are disordered.

Figures 14, 15A:
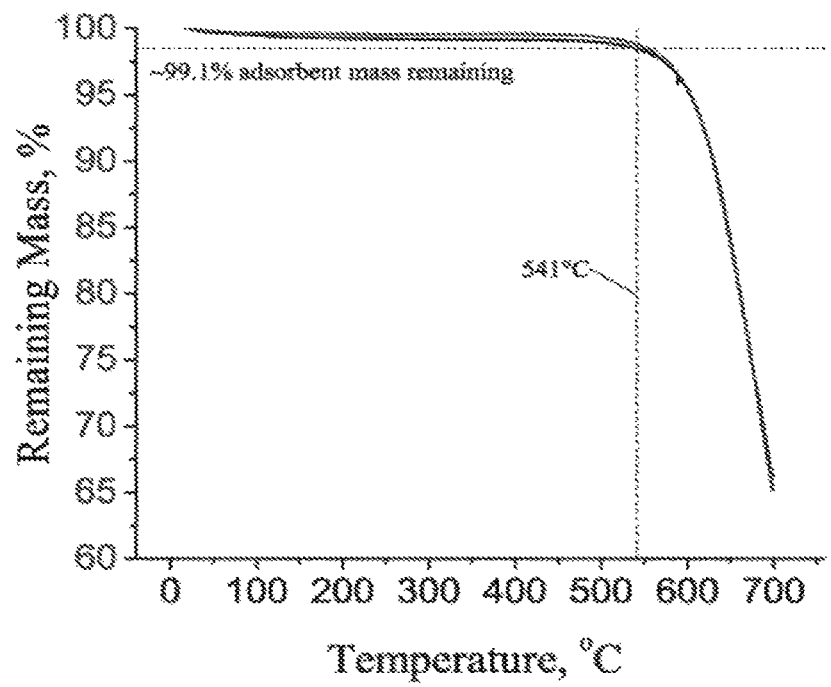
FIG. 14 shows TGA analysis of vacuum annealed C-500 GNP.
FIG. 15A shows the weight % composition of GNPs from EDS.

TGA data is displayed in FIG. 14, with both iterations of TGA on the graph. Under the flowing air environment, at 541° C. the vacuum annealed material had 99.1% of its mass left. This is an ideal oxidation temperature, as in this environment the surface will be activated, but will not burn up too quickly as evidenced by the large drop off in mass after about 600° C.

Figures 15B, 16:
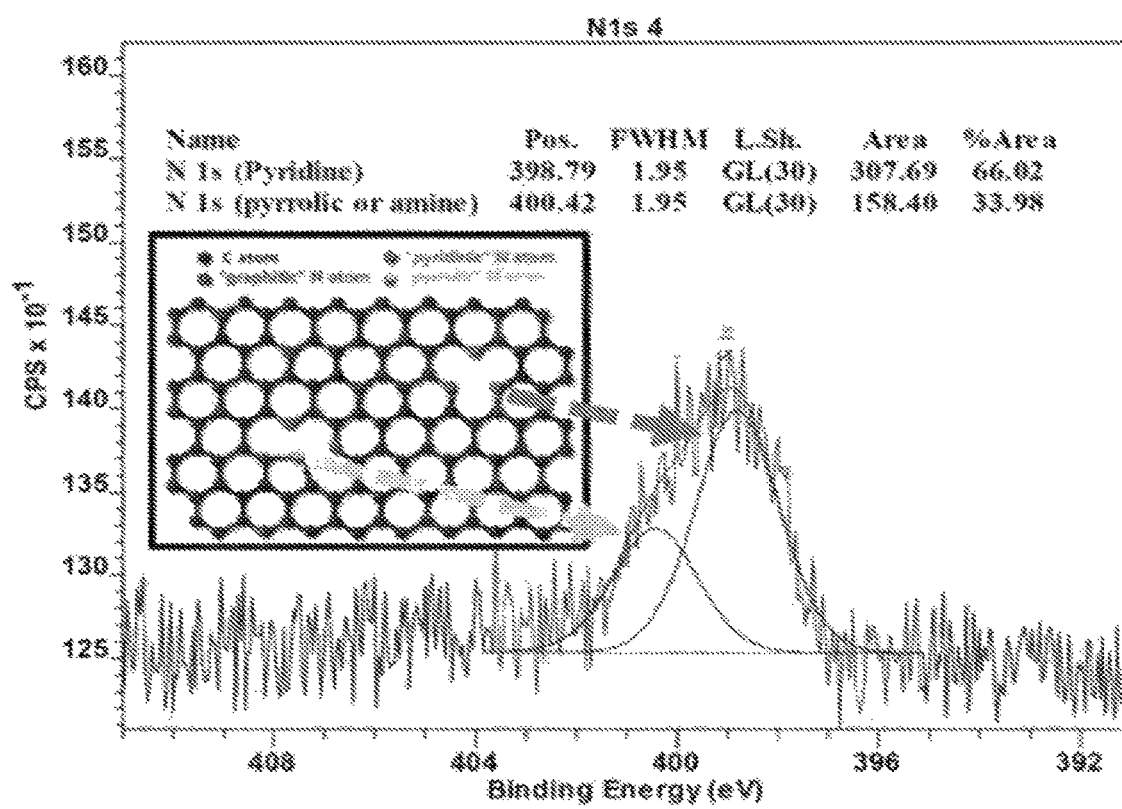
FIG. 15B shows the atomic % composition of GNPs from XPS.
FIG. 16 shows peak fitting for the nitrogen binding energies for the vacuum aminated GNP sample.

FIG. 15A shows the weight percentages of carbon, oxygen, and nitrogen for all of the surface-modified materials. A large decrease in oxygen is observed after vacuum annealing, acid oxidation introduces a large amount of oxygen to the surface, and 2% nitrogen is incorporated to the surface after amination. Despite exposure to ambient conditions for 10 days, vacuum annealed GNP still maintains a low oxygen content. FIG. 15B shows the survey scan composition results from XPS, and show a similar trend.

Peak fitting for the nitrogen binding energies is observed in FIG. 16 for the vacuum aminated sample. After performing peak fitting, it can be seen that nitrogen bonds were formed to replace carbon atoms and bind to dangling bonds as pyridine N atoms or form pentagons in the graphene structure with pyrrolic N atoms. The survey scans, EDS scans, and peak fitting confirm that defunctionalization and functionalization successfully occurred in all three materials.

Figure 17A:
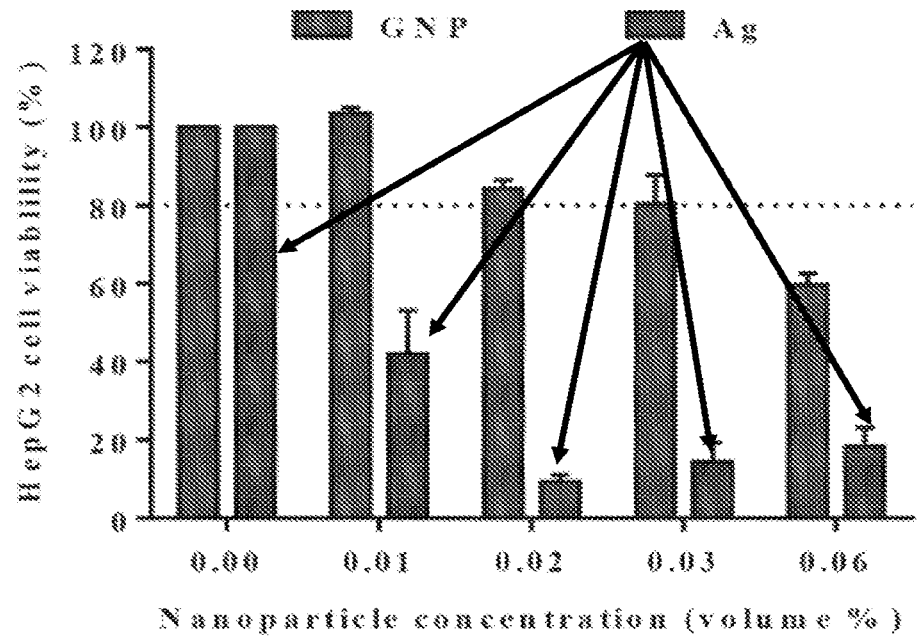
FIG. 17A shows cell viability for ARC-500, compared to silver nanoparticles (±standard error of mean, n=3).
Figure 17B:
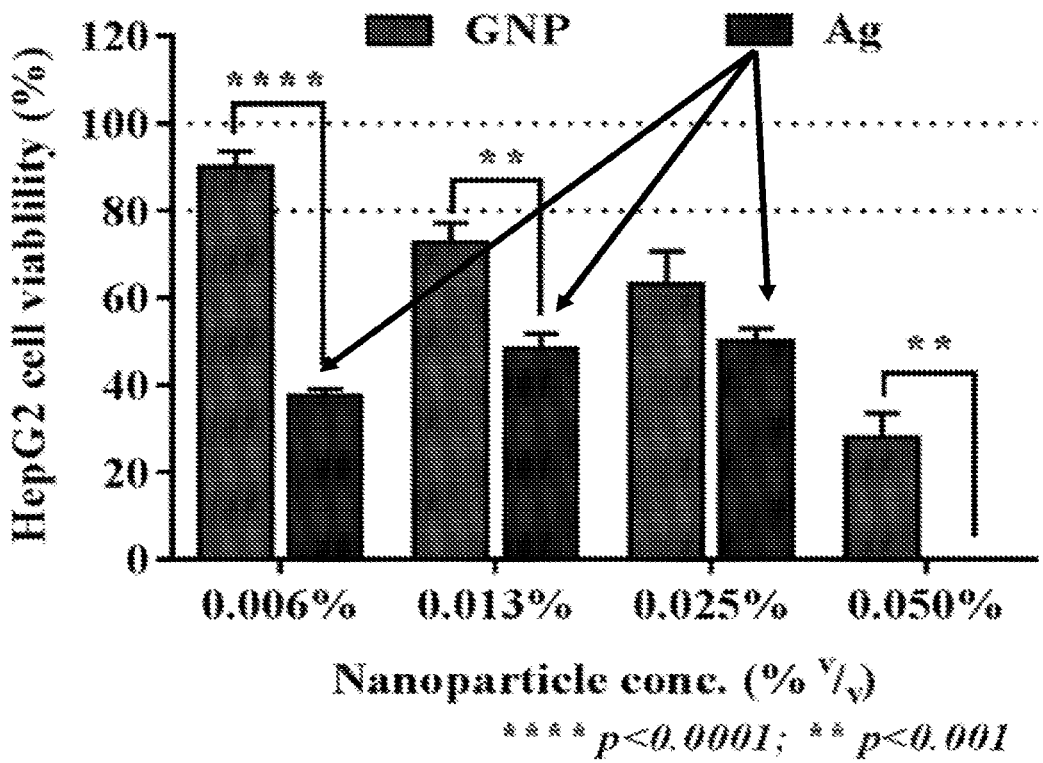
FIG. 17B shows the effect on HepG2 MTS cell viability after direct contact with graphene nanoplatelet (GNP) and silver nanoparticle (Ag) for 24 hours (±SEM, n=3).

MTS cell cytotoxicity data is seen in FIGS. 17A and 17B. ARC-500 maintains safe cell viability compared to silver nanoparticles at a concentration of 0.03% volume of ARC-500. At 0.06%, it falls to ~60% cell viability, below the 80% threshold defined here as cytotoxic. This decrease in cell viability is possibly due to the blocking of nutrients to the cells by the GNP, and inhibiting cell metabolism of nutrients.

Figure 18:
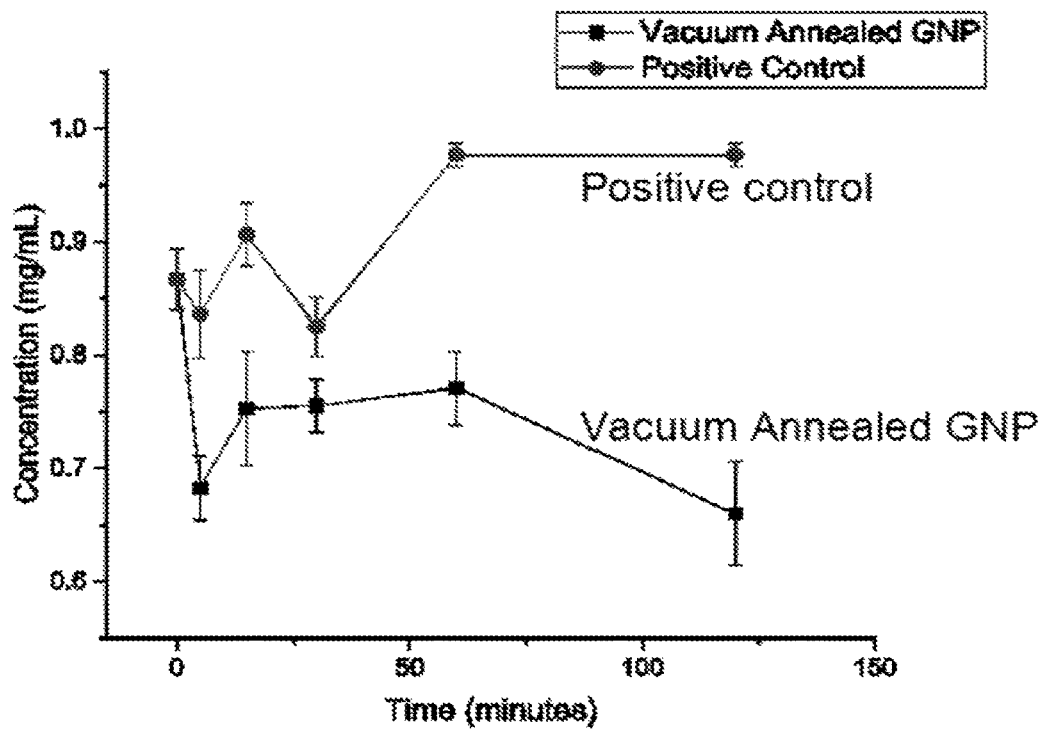
FIG. 18 illustrates BSA adsorption on vacuum annealed GNP. "Positive Control" is a solution of the protein in water, but without the carbonaceous material. This is used to monitor if any external effects are affecting adsorption (e.g. proteins sticking the walls of the tube, etc.)

FIG. 18 shows the adsorption performance of a model protein, BSA, onto a GNP.

Figure 19:
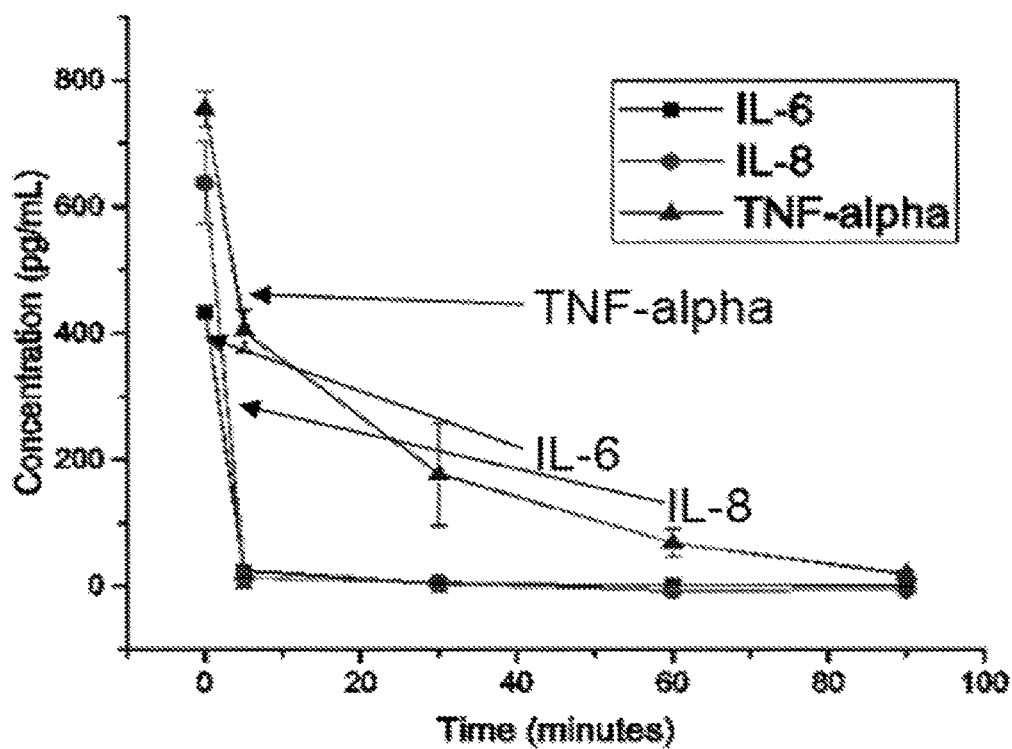
FIG. 19 shows cytokine adsorption on baked GNP.
Figure 20A:
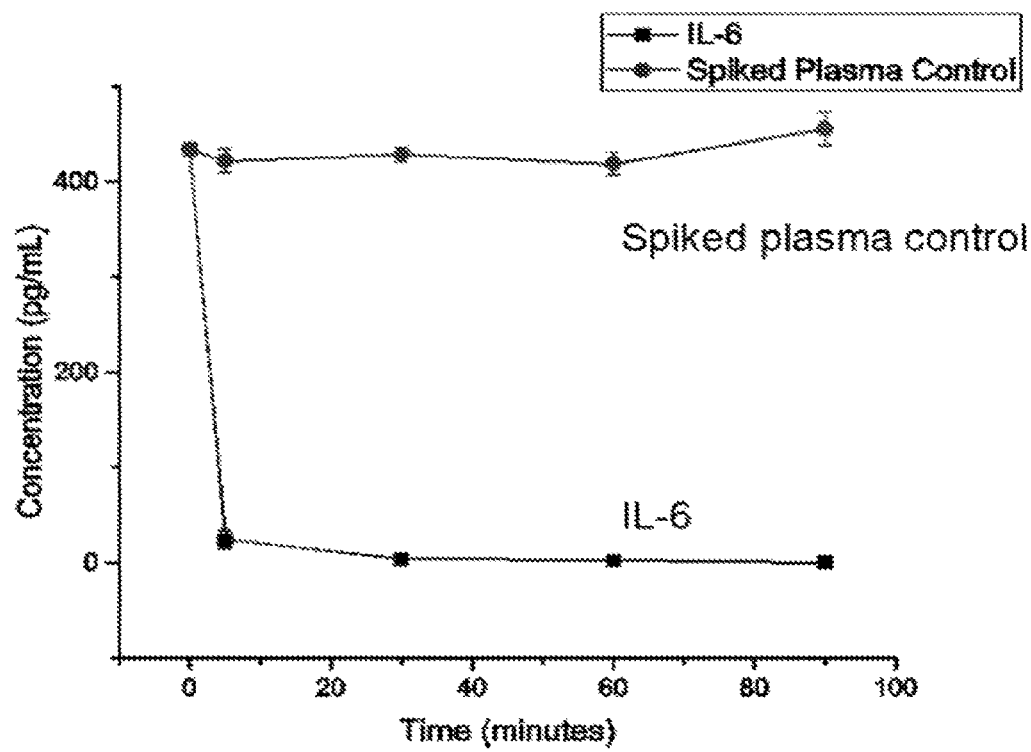
FIGS. 20A-20C illustrates cytokine adsorption on nitrogen baked GNP.
Figure 20B:
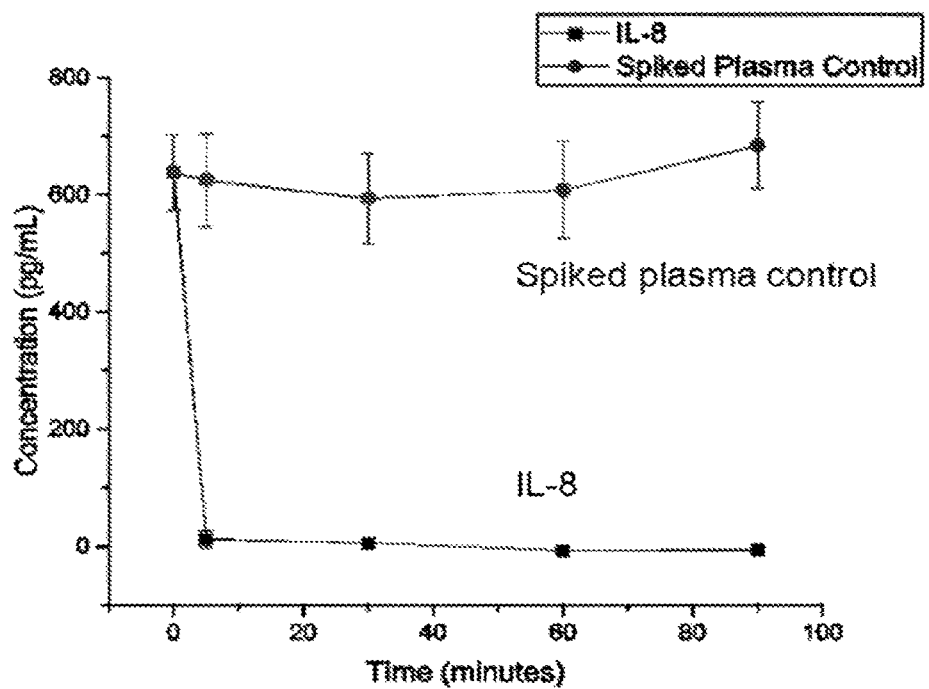
Figure 20C:
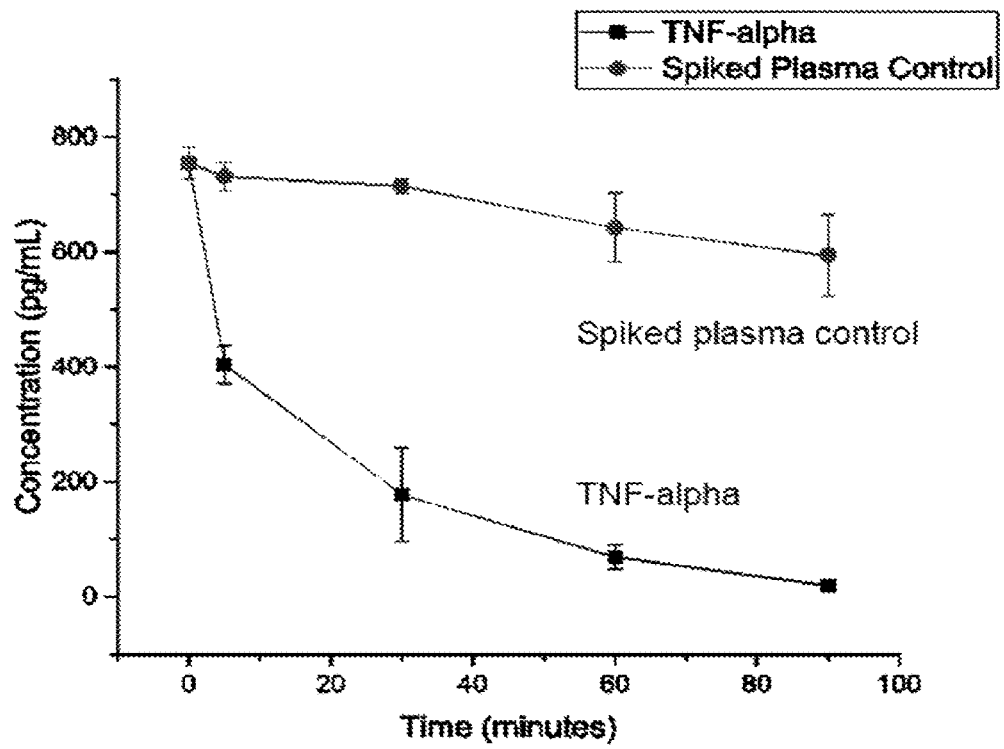
Figure 21A:
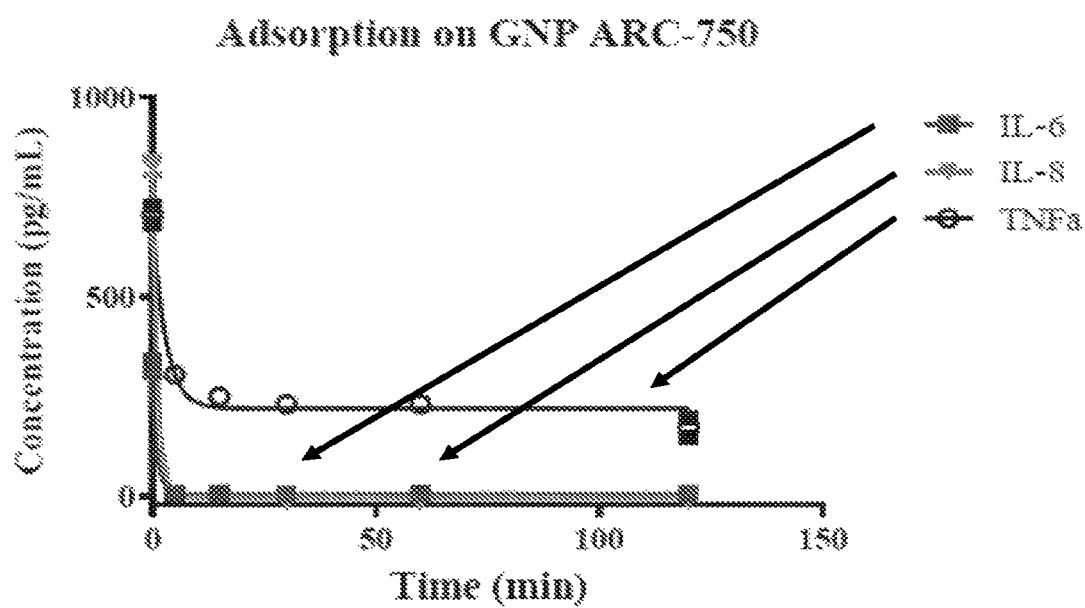
FIGS. 21A-21F show cytokine concentration and normalized adsorption on GNPs of different surface area.
Figure 21B:
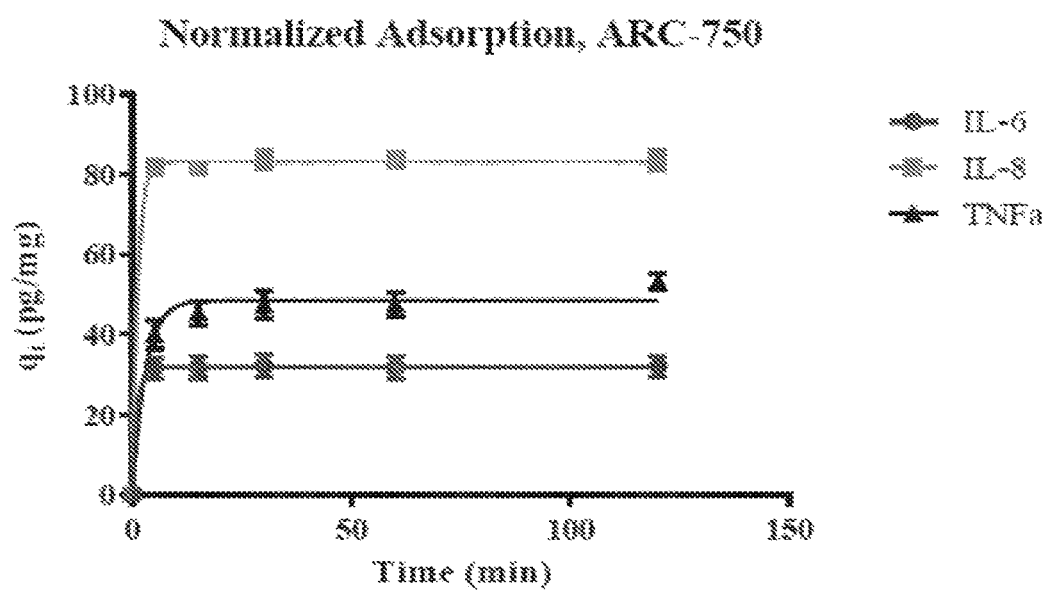
Figure 21C:
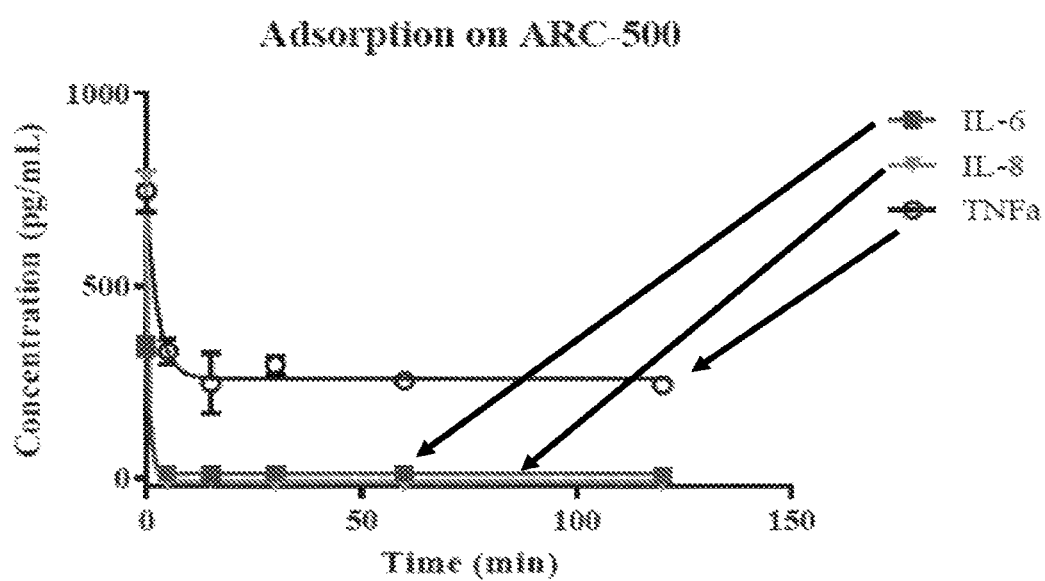
Figure 21D:
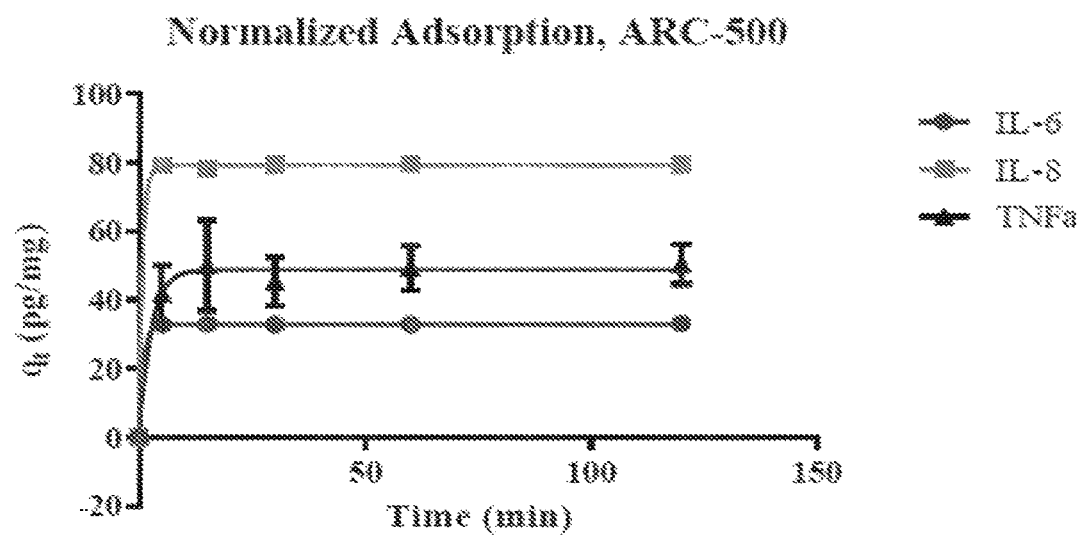
Figure 21E:
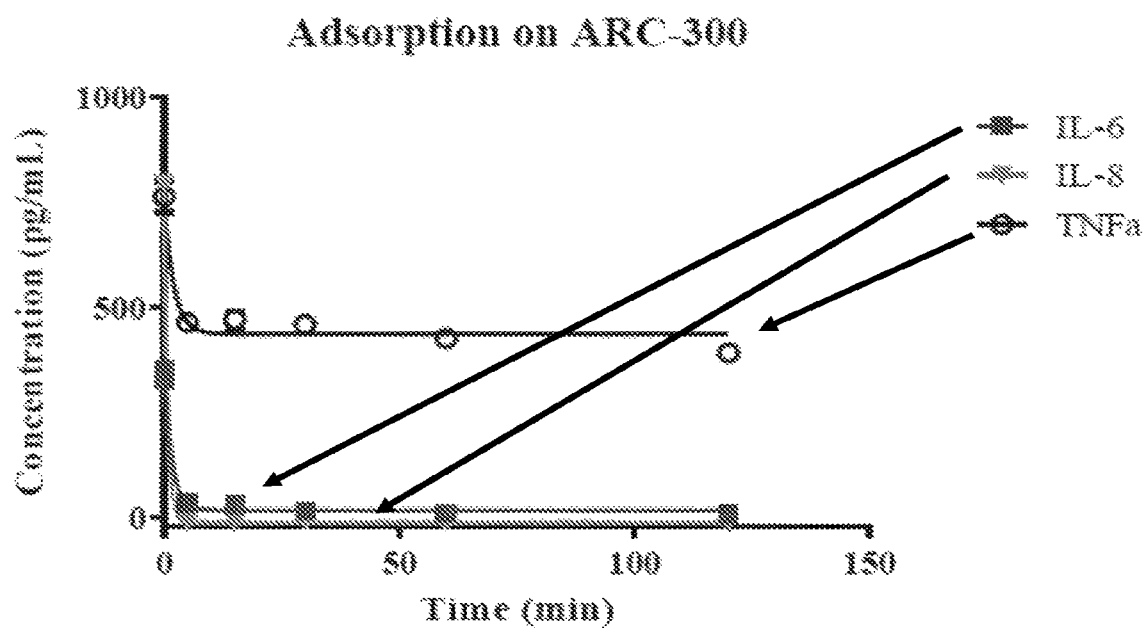
Figure 21F:
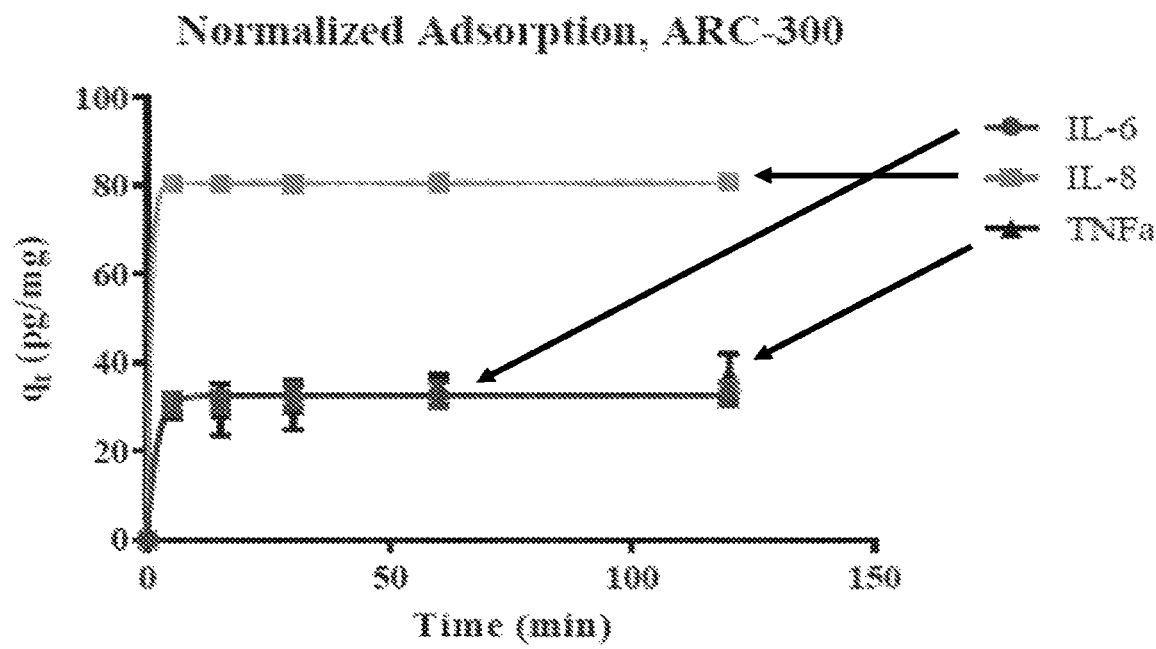
Figure 22A:
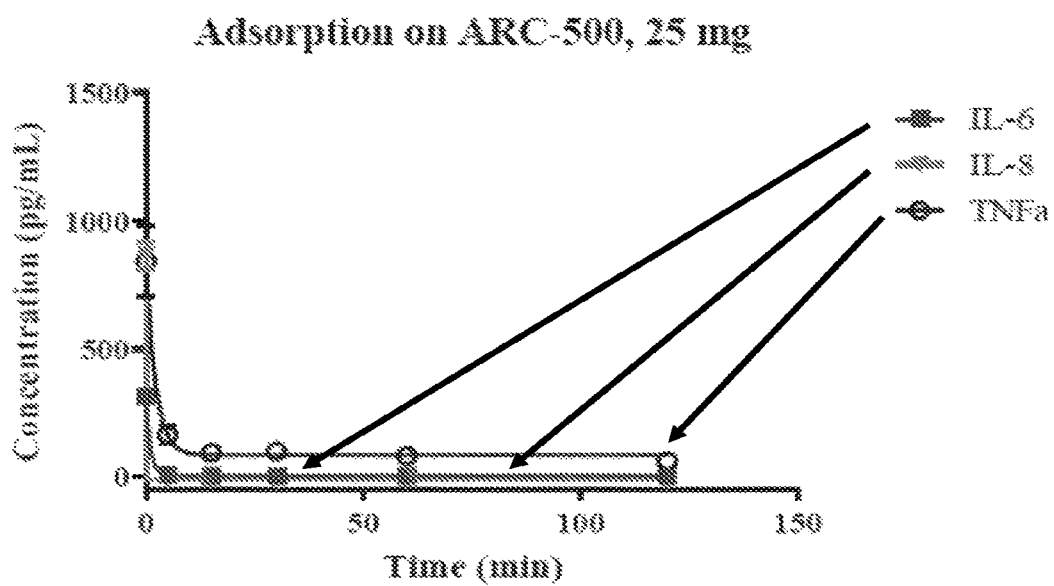
FIGS. 22A-22F show cytokine concentration and normalized adsorption on ARC-500 with different masses of adsorbent.
Figure 22B:
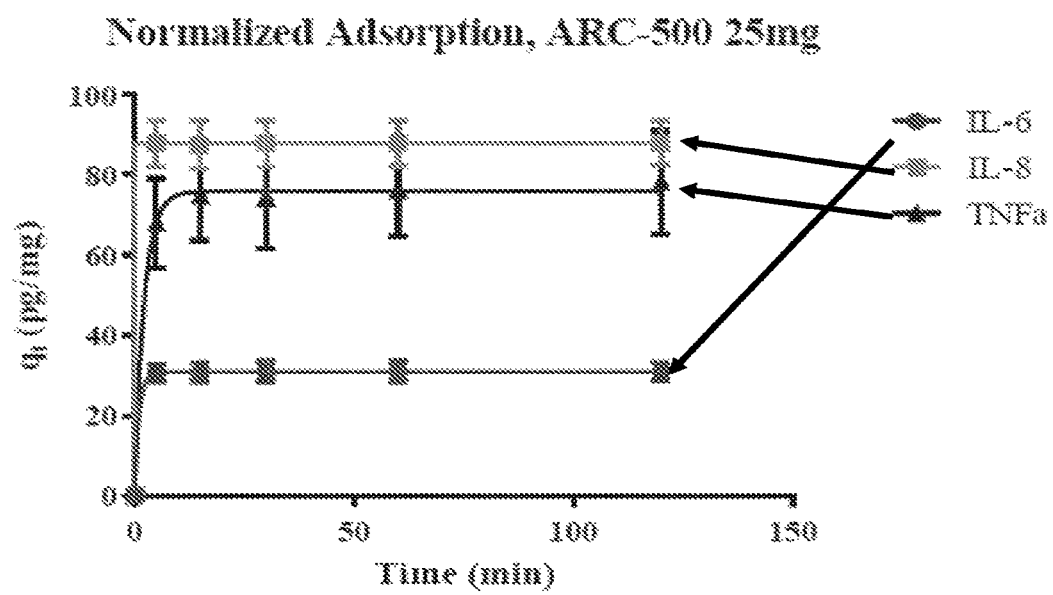
Figure 22C:
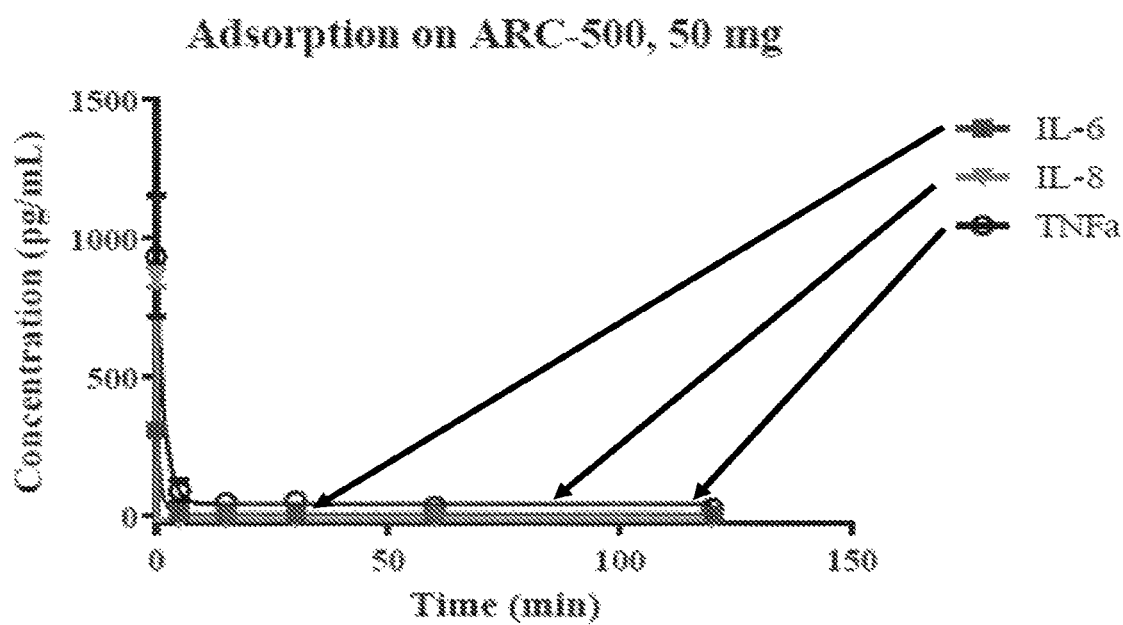
Figure 22D:
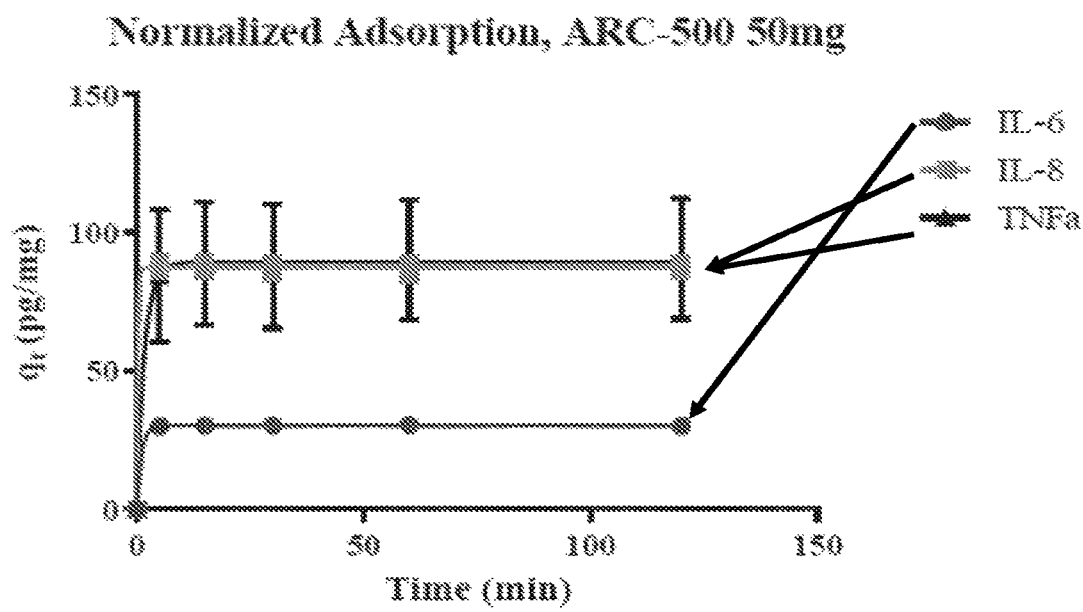
Figure 22E:
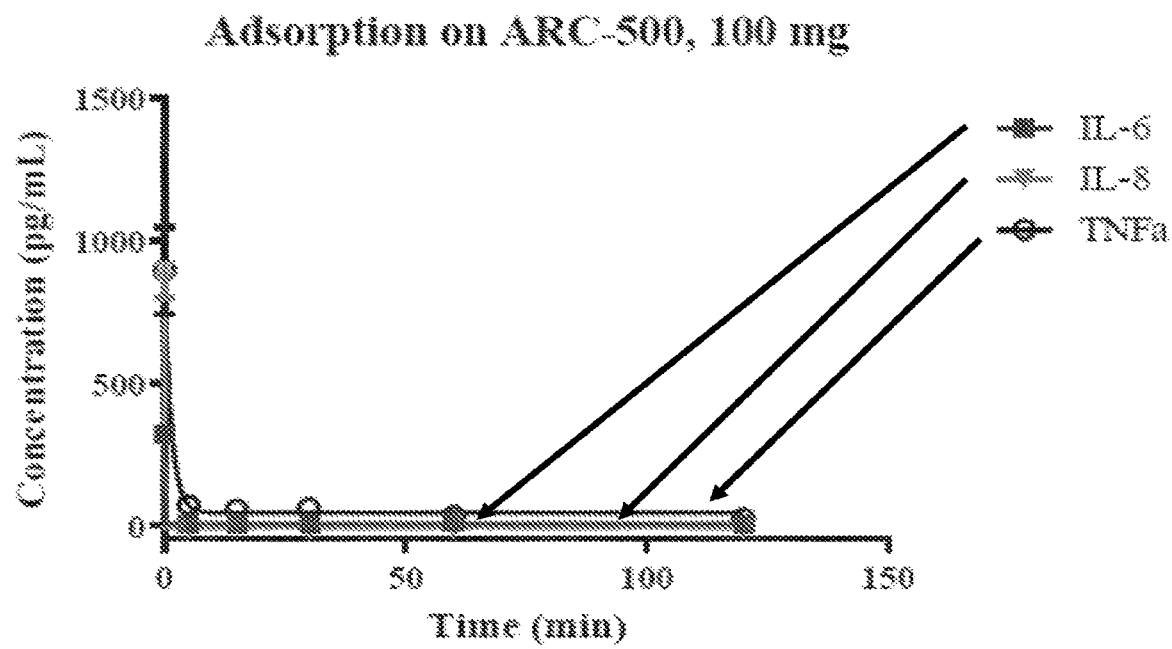
Figure 22F:
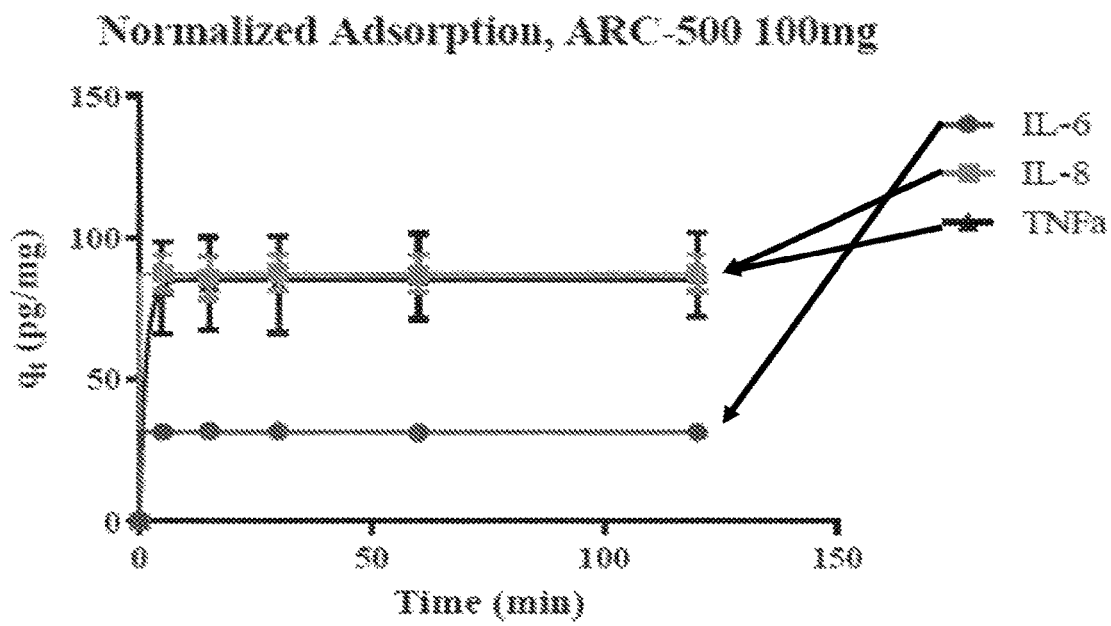
Figure 23A:
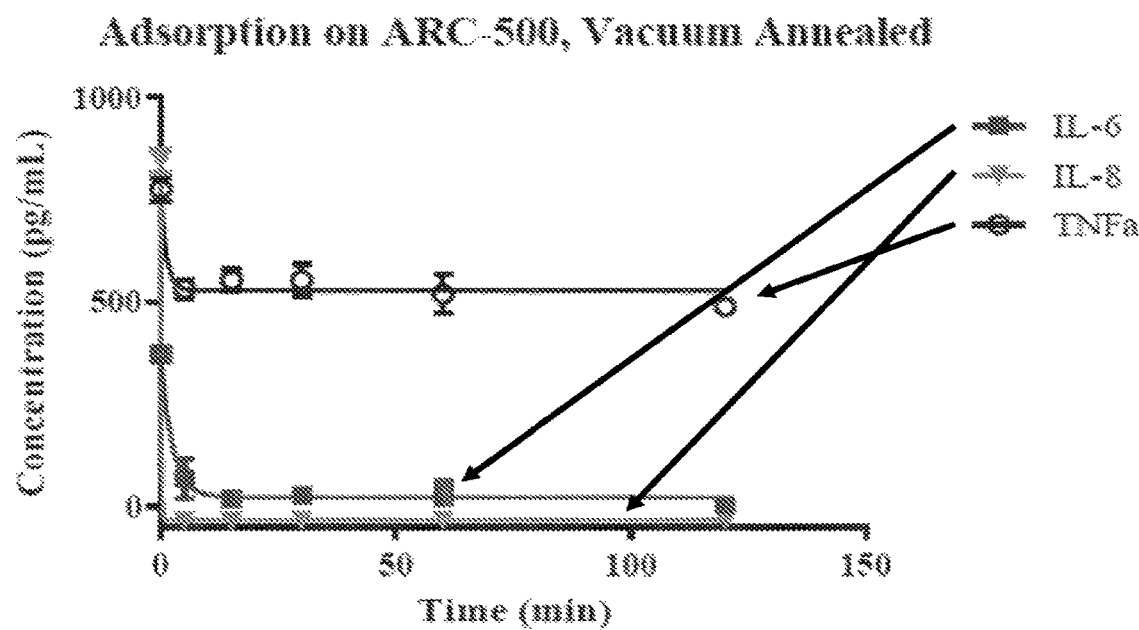
FIGS. 23A-23F show cytokine concentration and normalized adsorption on C-500 with various surface chemistry.
Figure 23B:
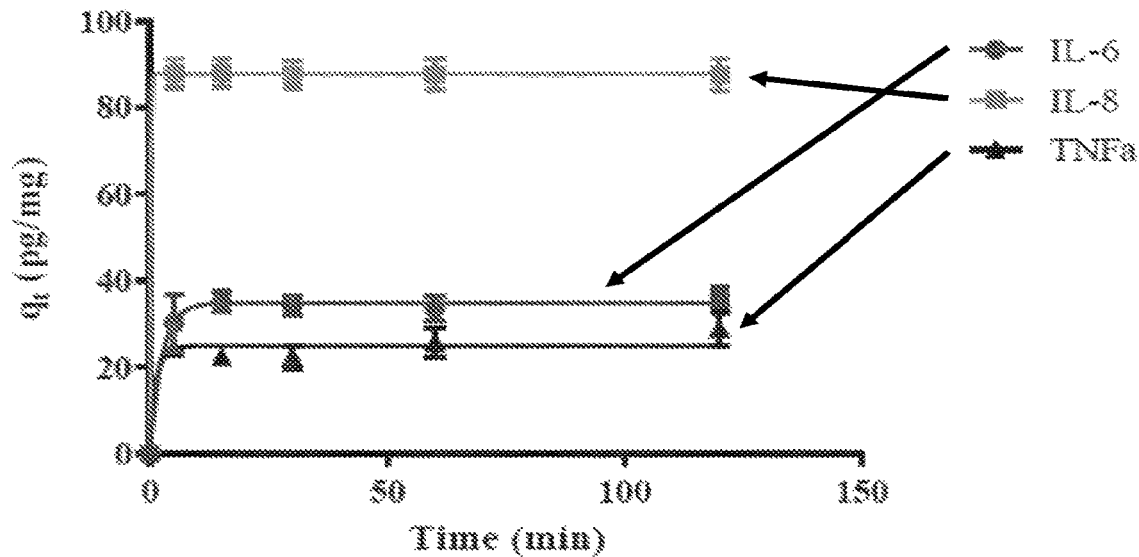
Figure 23C:
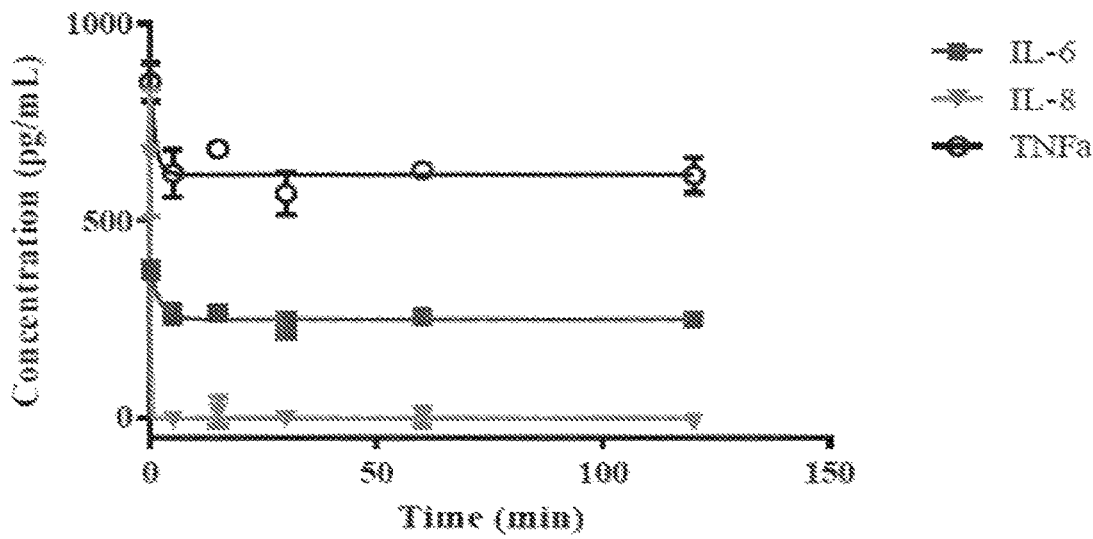
Figure 23D:
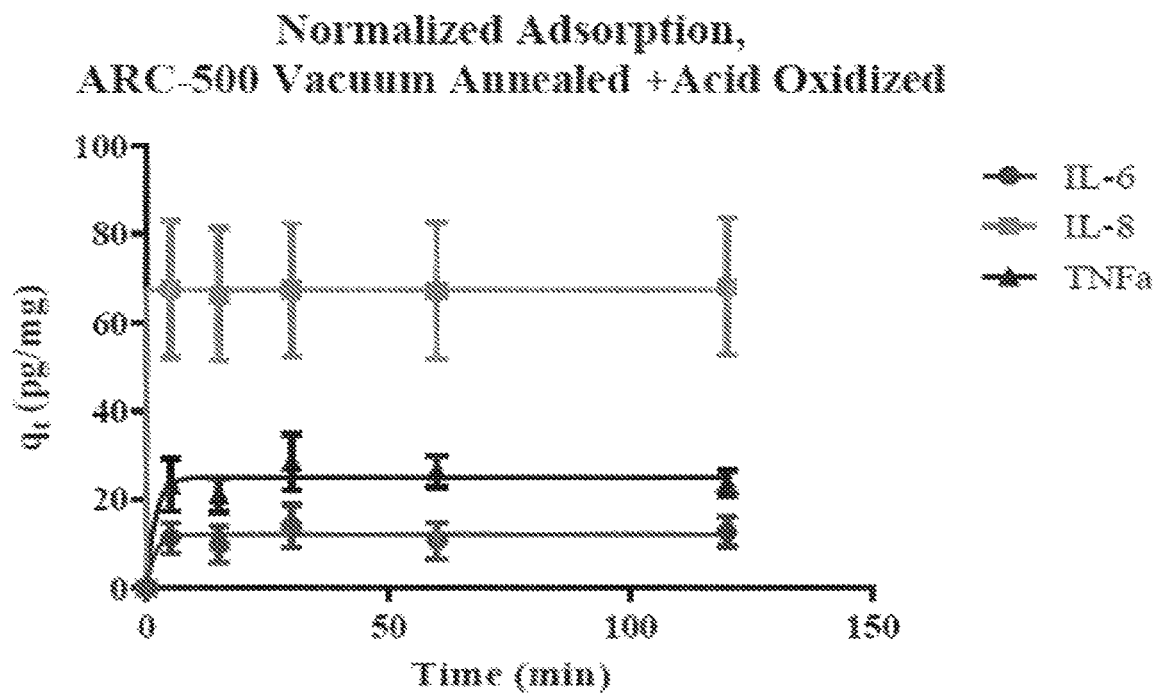
Figure 23E:
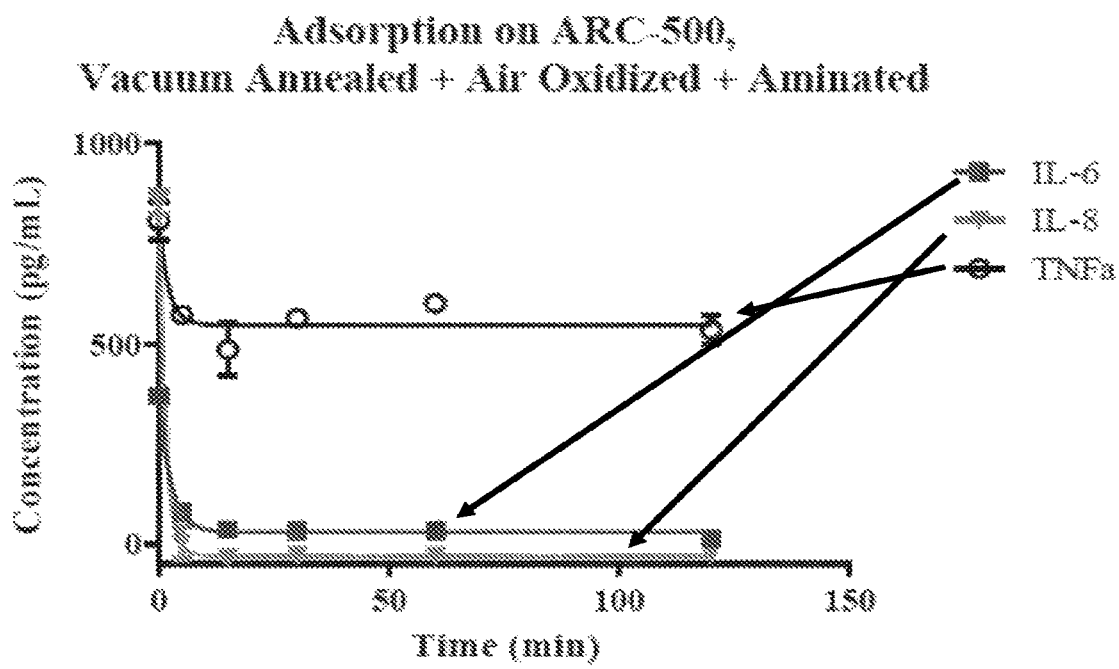
Figure 23F:
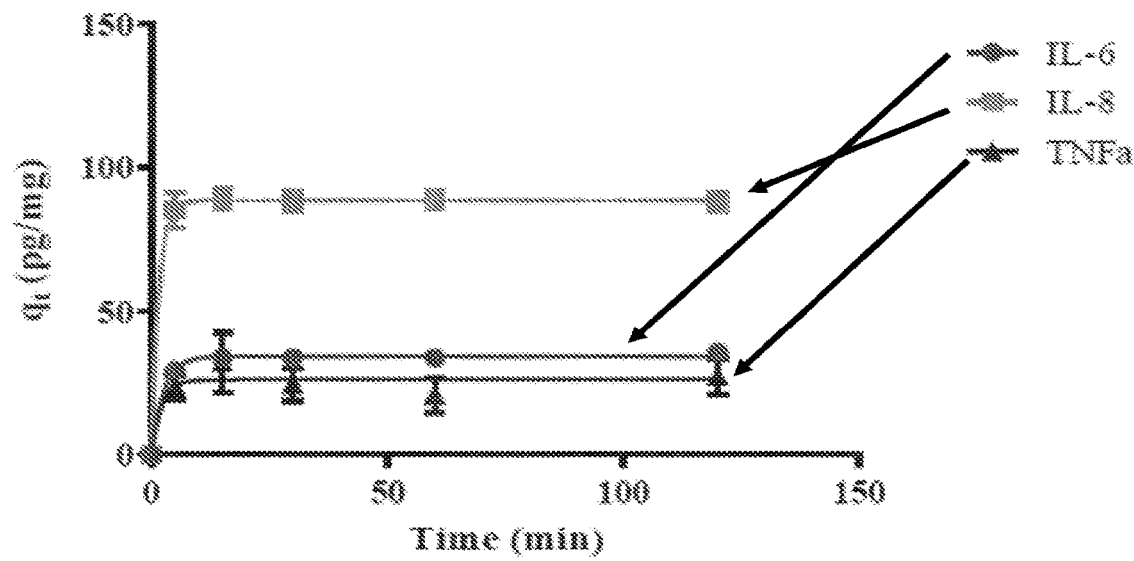

FIG. 19 shows the adsorption of cytokines onto GNP. These are further itemized by individual cytokine adsorbed in FIGS. 20A-20C, including their respective positive controls.

The nanoplatelets show an ability to rapidly remove cytokines from plasma, as all proteins are adsorbed to negligible levels within under 90 minutes. PDC-CDC samples did not show as fast kinetics, but still demonstrated the ability to adsorb cytokines.

FIGS. 21A-F, FIGS. 22A-F, and FIGS. 23A-F display the cytokine (IL-6, IL-8 and TNF-α) concentration as a function of time and normalized adsorption for all of the variations of GNP, tested in triplicate. Tables 3 through 8 show pertinent values obtained from fitting the normalized adsorption data to both an exponential decay function and Ho and McKay's pseudo second-order function. See Y. S. Ho and G. McKay, "Pseudo-second order model for sorption processes," *PROCESS BIOCHEMISTRY*, vol. 34, pp. 451-465, 1999. McKay's function has overall excellent $R^2$ values relative to the exponential decay function, and, for further analysis, the equilibrium adsorption q will be used instead of $q_W$, although their values are similar for most data sets. qc is the normalized adsorption capacity at equilibrium, or when the adsorbent is fully saturated with adsorbate on the surface. Its units are mass of cytokine adsorbed per unit mass of adsorbent.

All GNP samples quickly adsorb to capacity, as evidenced by the lack of marginal increase in normalized adsorption after 5 minutes for any sample. With the exception of the acid oxidized C-500 material, all variations of GNP saw rapid adsorption of IL-6 and IL-8 after 5 to 15 minutes to negligible concentrations. Using a two-way ANOVA multiple comparisons test, it was observed that all of the positive controls (e.g. plasma with excess cytokines but no adsorbent) did not see statistically significant differences between time points, except in the controls for studies on TNF-α of the ARC-300 material. Between the beginning of the study and 120 minutes, the difference was statistically significant with a p value 5 0.05.

The adsorption capacity for ARC-750, ARC-500, and ARC-300 is similar for all three cytokines at ~33 μg/mg. Increasing the mass of adsorbent resulted in a faster decrease in the protein concentration. This was especially significant in TNF-α removal, where increasing the mass decreased the concentration an additional 400 μg/mL after 5 minutes, when comparing 10 mg to 25 mg of adsorbent.

Surface functionalities did not appear to improve cytokine adsorption, as q. values for TNF-α decreased when compared to different surface area materials, while other q, values remained in a similar range. The kinetics of adsorption remained the same; adsorption was fast and equilibrium was reached after about 5 minutes.

Figure 24:
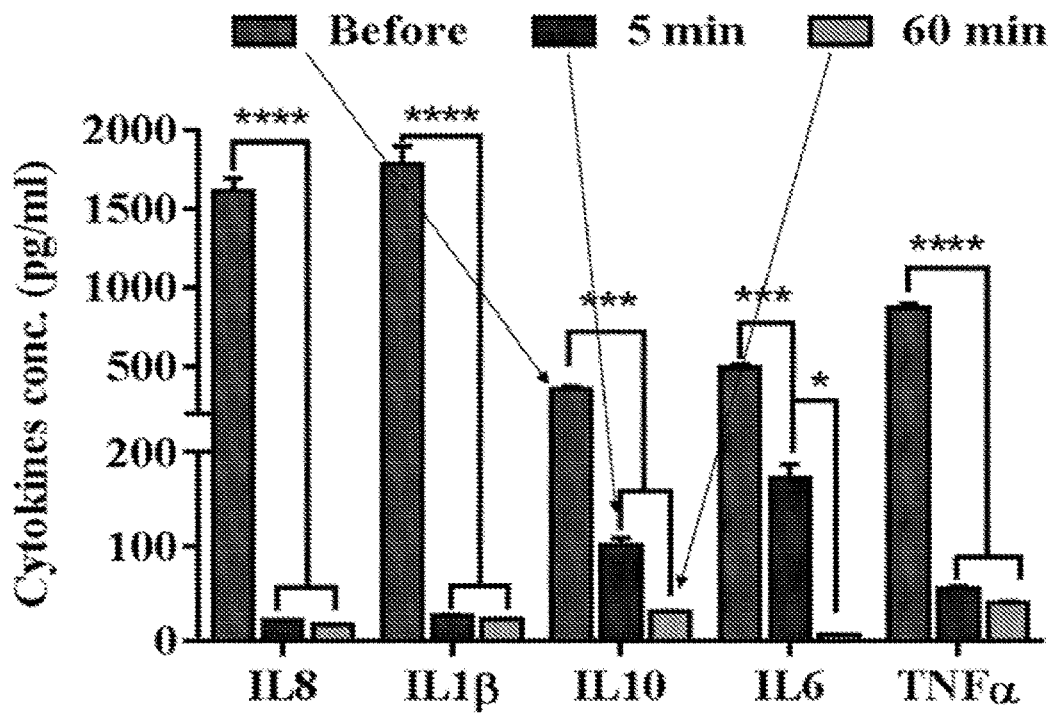
FIG. 24 shows the removal of inflammatory cytokines IL8, IL1β, IL10, IL6 and TNF-α in spiked human plasma samples after 5 and 60 minutes of direct contact with graphene nanoplatelet (±SEM, n=3).
Figure 25A:
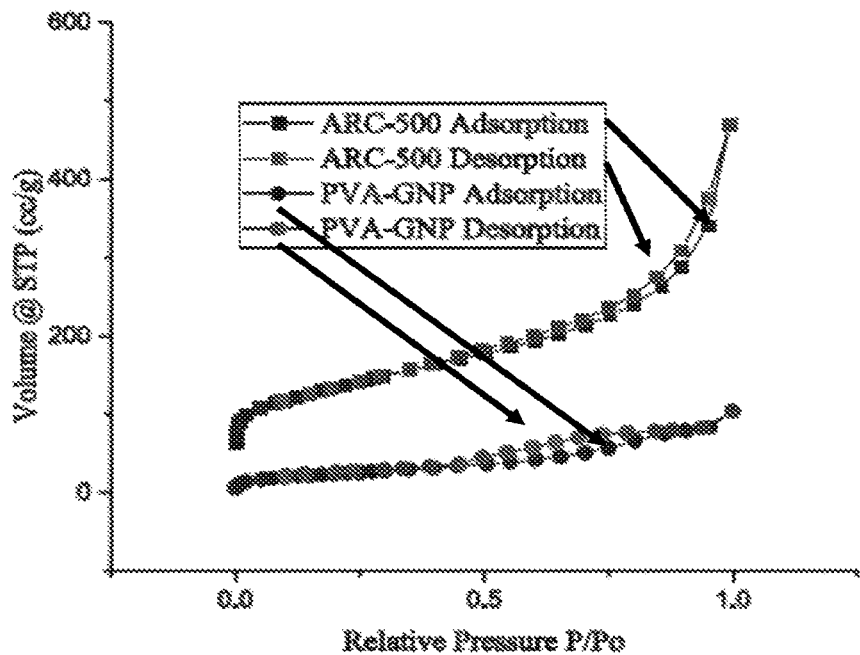
FIGS. 25A-25D show nitrogen adsorption and pore size distributions of GNP composites.
Figure 25B:
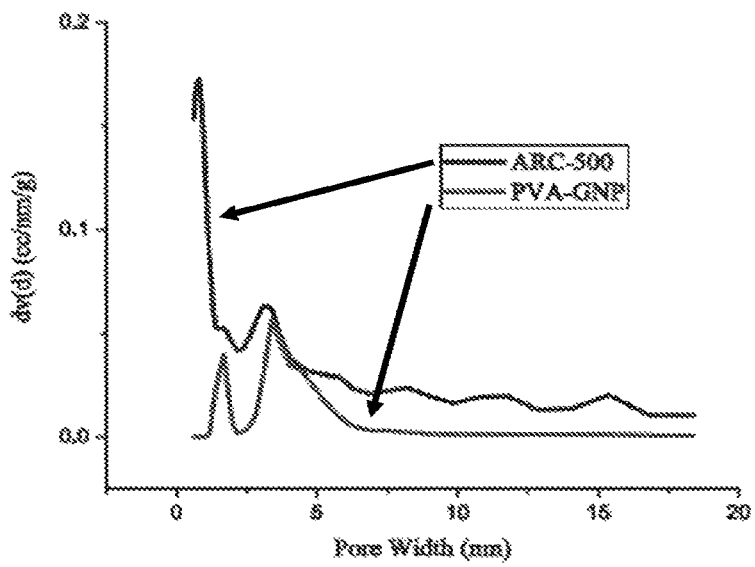
Figure 25C:
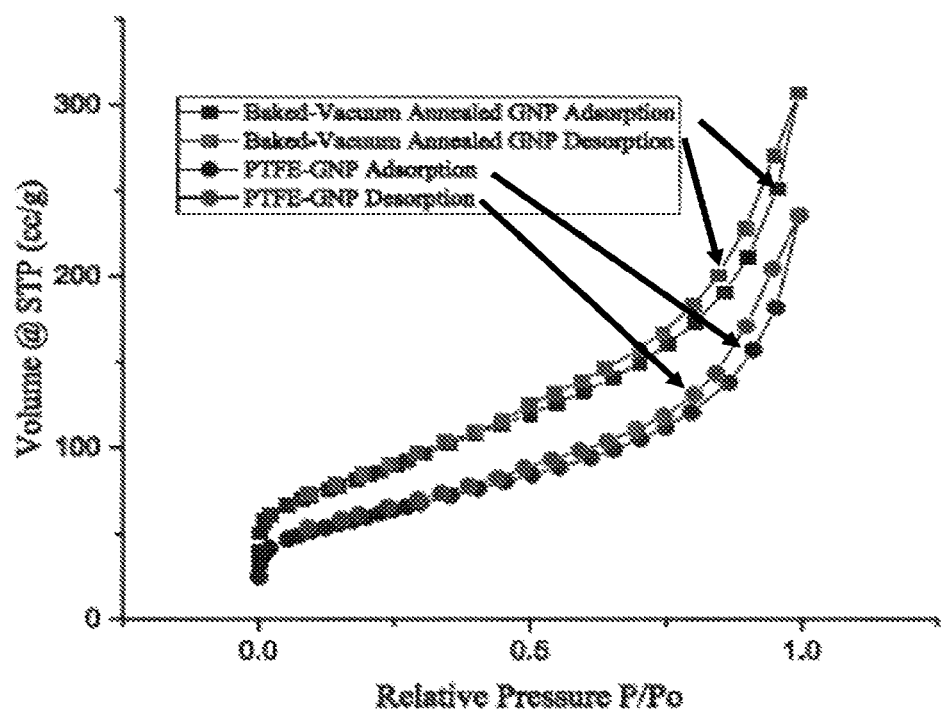
Figure 25D:
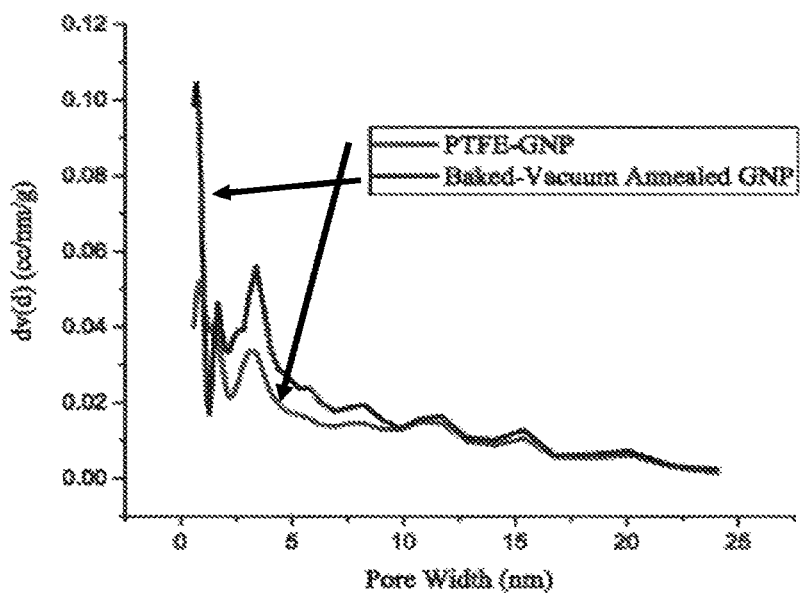
Figure 27B:
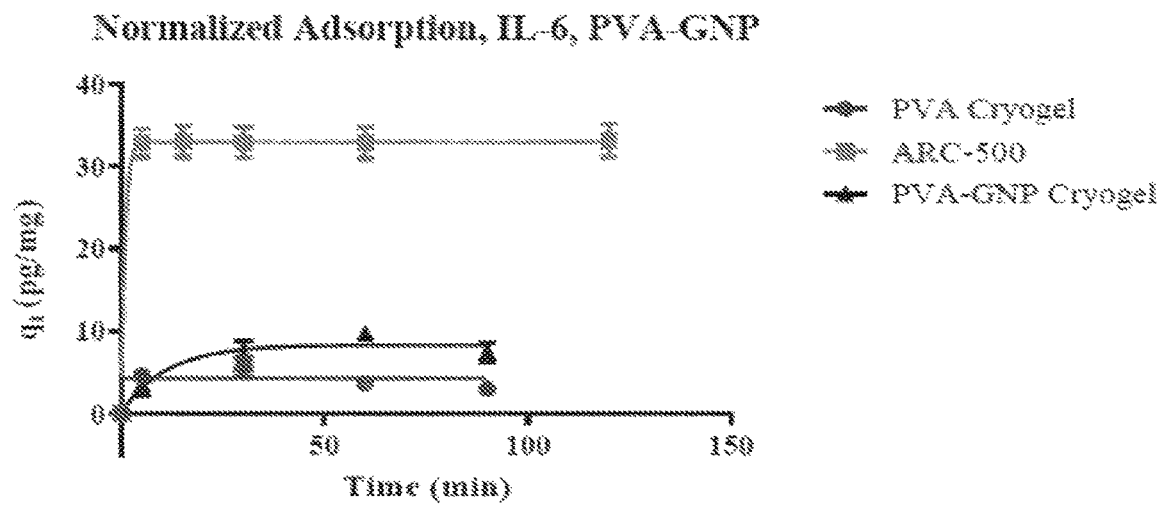
Figure 27C:
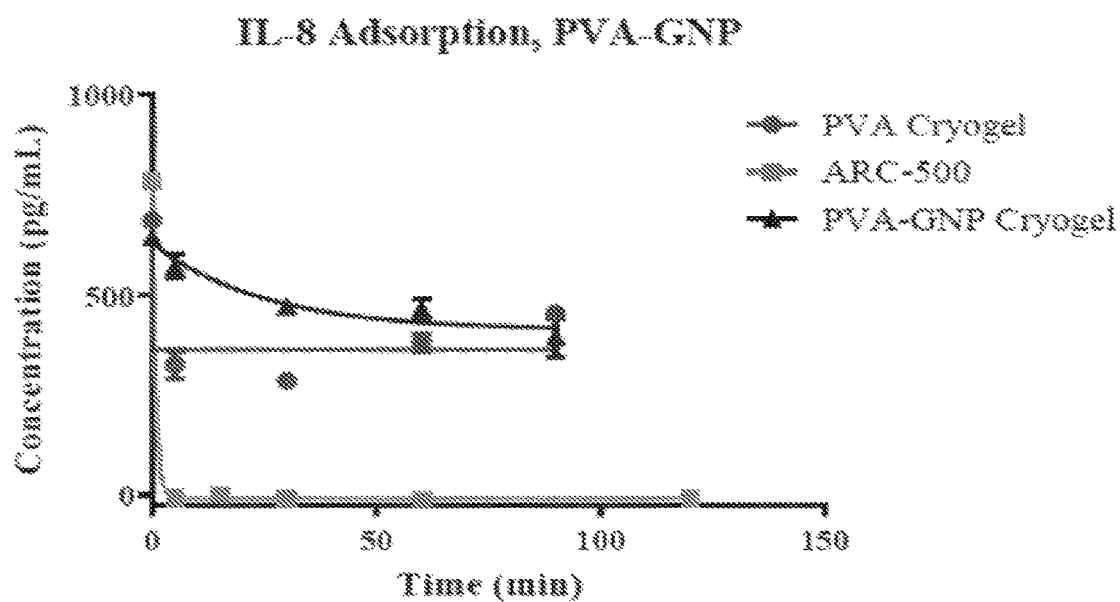
Figure 27D:
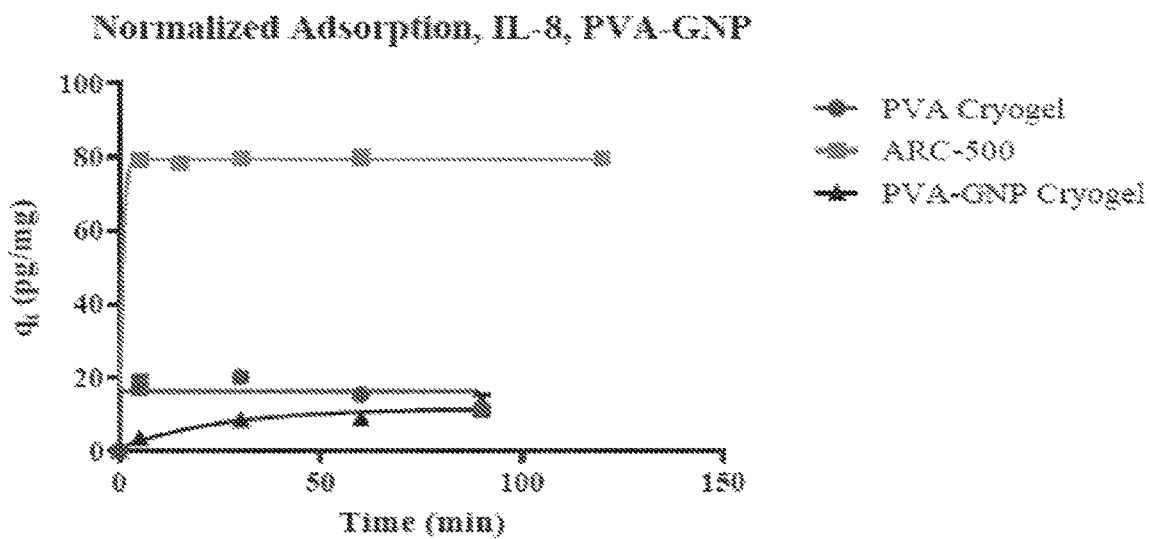
Figure 27E:
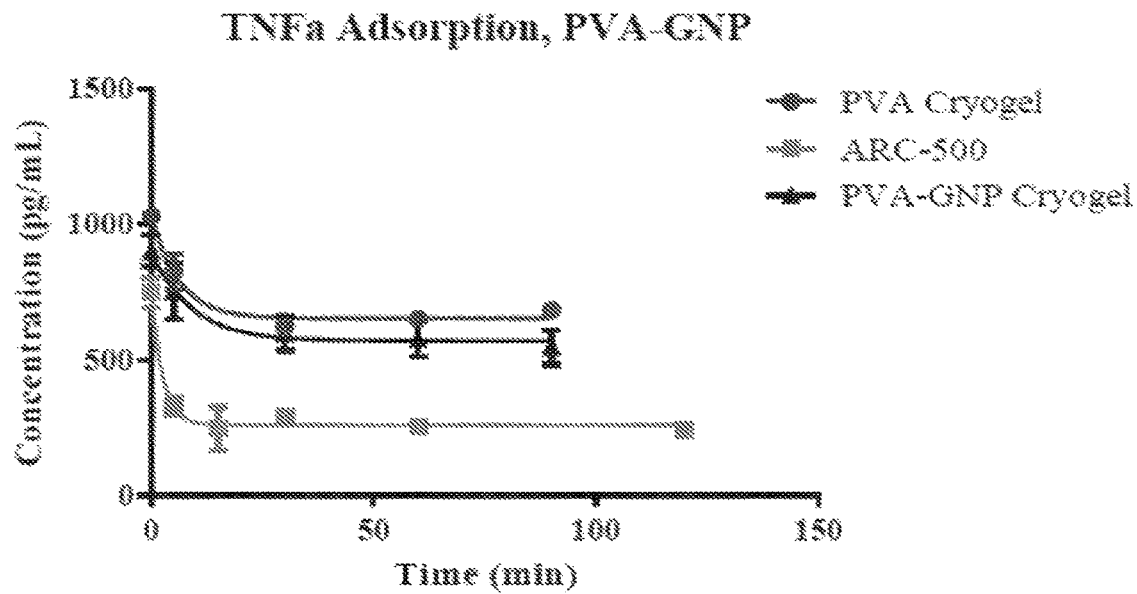
Figure 27F:
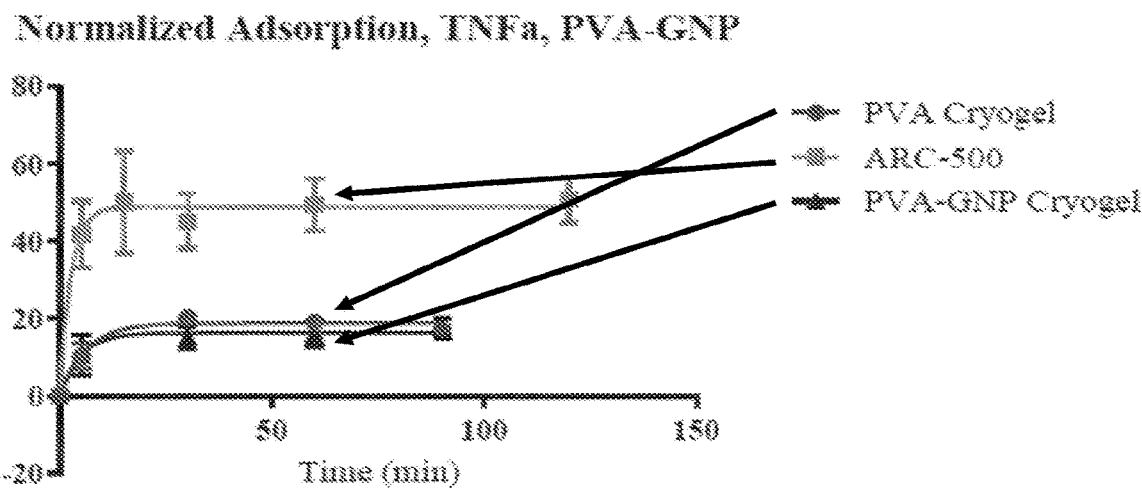

GNP particles showed rapid and efficient removal of cytokines from human plasma spiked with a cytokine cocktail. The concentration of smaller cytokines IL-8 (8 kDa) and IL-10 (17 kDa) in the spiked plasma was reduced from over 1500 μg/ml to 20 μg/ml within 5 minutes of direct contact (FIG. 24). In comparison, the GNP removal of larger cytokine markers IL-10 (18.5 kDa) and IL-6 (20.5 kDa) appeared to be slightly slower; however, a 60% and 50%1 removal was achieved within the first 5 min of contact. Although TNF-αz has a molecular weight of 17.5 kDa, it is reported to exist in the trimer form making it one of the most challenging molecules to remove in conventional blood purification techniques. A reduction in the plasma TNF-α concentration from 868 μg/mi to 55 μg/ml after 5 min contact with GNP indicated a rapid and efficient TNF-α removal by GNP. The cytokine marker removal profile indicated that GNP could be used to remove different molecular weight cytokines from spiked plasma, demonstrating potential for broad spectrum cytokine removal for applications such as sepsis. The fast adsorption kinetics can be attributed to direct contact with a completely accessible surface area, and minimal diffusion barriers to the surface, in contrast with adsorbing into a pore. Low flow rates typical with powder adsorbents in blood purification applications can lead to issues such as high pressure in the system and small particle release causing a micro embolism. To overcome these issues, GNP-PTFE composite film was developed in this study.

Materials characterization was primarily completed on nanoplatelets, due to their excellent adsorption efficiency. Particle size distribution data for GNP is shown in FIG. 7.

TABLE 1

Surface area and Pore data for materials described herein

| | Average Particle Size (nm) | BET SSA ($m^2/g$) | QSDFT SSA ($m^2/g$) | $V_{QSDFT}$ ($cm^3/g$) | $D_{mode}$ (nm) | PDI |
|---|---|---|---|---|---|---|
| ARC-750 | 332.0 | 650.7 | 630.9 | | | 0.37 |
| ARC-500 | 627.6 | 465.6 | 454.5 | 0.547 | 0.785 | 0.53 |
| ARC-300 | 1338.0 | 288.73 | 284.44 | | | 0.81 |
| C-500 Vacuum Annealed | 1670.0 | 392.5 | 383.3 | | | 0.54 |
| C-500 Vacuum Annealed, Acid Oxidized | 806.6 | | 63.0 | | | 0.60 |
| C-500 Vacuum Annealed, Air Oxidized, Ammonia Aminated | 1756.0 | 158.1 | 155.9 | | | 0.57 |
| Baked-Vacuum Annealed GNP | | 293.66 | 292.26 | 0.397 | 0.723 | |

TABLE 1-continued

Surface area and Pore data for materials described herein

| | Average Particle Size (nm) | BET SSA (m²/g) | QSDFT SSA (m²/g) | $V_{QSDFT}$ (cm³/g) | $D_{mode}$ (nm) | PDI |
|---|---|---|---|---|---|---|
| PVA Cryogel - GNP | | 87.64 | 72.37 | 0.123 | 3.395 | |
| PTFE-GNP | | 210.38 | 193.69 | 0.301 | 0.852 | |
| GNP C500 Baked | 547 | 818 | 775 | | | |
| PDC-CDC A Low MW | 499 | 54 | 51 | 0.122 | 1.543 | 0.55 |
| PDC-CDC B High MW | 685 | 125 | 114 | 0.249 | 8.23 | 0.67 |

TABLE 2

Graphene nanoplatelet samples specific surface area, pore volume was determined using nitrogen adsorption analysis. Sample specific surface area ($S_{BET}$), was calculated based on Brunauer-Emmett-Teller ($S_{BET}$) and Quenched Solid State Functional Theory ($S_{QSDFT}$), QSDFT were also applied to estimate the pore size ($D_{mode}$) and particle size were determined using dynamic light scatter.

| Sample | $S_{BET}$ (m²/g) | $S_{QSDFT}$ (m²/g) | $V_{QSDFT}$ (CM³/g) | $D_{Mode}$ (nm) | Particle size (nm) |
|---|---|---|---|---|---|
| Initial GNP | 797.4 | 776.1 | 0.807 | 0.785 | 547.2 |
| VA-GNP | 293.7 | 292.3 | 0.397 | 0.723 | 1670.0 |
| VA-GNP-PTFE | 210.4 | 193.7 | 0.301 | 0.852 | — |

GNP Composites:

As discussed above, a flexible and free-standing film was prepared from rolling out the GNP-PTFE mixture with ethanol; when ethanol was removed, the PTFE bound GNP particles together into a matrix.

FIGS. 25A-25D illustrate the nitrogen adsorption isotherms and pore size distributions for the PVA-GNP cryogel and PTFE-GNP film composites, respectively. Table 1 displays the surface area, pore volume, and mode of the pore width information for the composites and the nanoplatelets imbedded in them. A non-porous composite is observed for PTFE-GNP, with a reduction in SSA of about ~80 m²/g after incorporation into the film. Adsorption isotherms for both baked-vacuum annealed GNP and PTFE-GNP film showcase a Type II isotherm, indicative of a non-porous material. S. Lowell and J. E. Shields, "Adsorption isotherms," in *Powder Surface Area and Porosity*, ed Dordrecht: Springer Netherlands, 1991, pp. 11-13. The lack of porosity in the film should not inhibit protein adsorption, as long as the nanoplatelets' surfaces are accessible. The nitrogen adsorption analysis revealed that the use of PTFE binder was able to preserve the large surface areas of the vacuum annealed GNP (Table 2).

For the PVA-GNP, there was a small amount of nitrogen adsorbed and a hysteresis was observed, which is indicative of mesopores. However, micropores and mesopores were also seen in GNP, and at higher pore volume contributions dV(d). This leads to the conclusion that there was little permeability of nitrogen into the cryogel during the adsorption experiment, contributing to the large drop in SSA. One can attribute these property changes to nitrogen gas not diffusing to the nanoplatelets by saturating large macropores with gas. This prevents gas from accessing and adsorbing to high surface area GNPs imbedded within the polymer network. The macropores will have a much smaller SSA than the GNP, leading to the decrease in this value. Pores are observed in the GNPs in both pore size distributions; these pores have likely arisen due to gentle crumbling at the graphene surface. See J. Y. Lee, K.-H. Lee, Y. J. Kim, J. S. Ha, S.-S. Lee, and J. G. Son, "Sea-Urchin-Inspired 3D Crumpled Graphene Balls Using Simultaneous Etching and Reduction Process for High-Density Capacitive Energy Storage," *Advanced Functional Materials*, vol. 25, pp. 3606-3614, 2015.

Most of the isotherms are indicative Type II or nonporous isotherms. The vacuum annealed C-500, ARC-500, and ARC-750 have the highest adsorption of nitrogen.

FIGS. 26A and 26B display SEM images of the PVA-GNP composite and PTFE-GNP film, respectively. Using ImageJ software, the average cross-section of the pores in the cryogel was measured at 277 nm and the average particle diameter in the PTFE film was 211 nm. The pore size is large enough to allow transport of plasma, but blood cells will need a larger pore channel to travel through. While this cryogel is appropriate to test for cytokine adsorption in plasma studies, a larger porous network in the cryogel is needed for hemoperfusion application. The PTFE-GNP film shows GNP particles with an average diameter smaller than the vacuum annealed particles studied in GNP. Extra processing steps, such as grinding the PTFE+GNP slurry and rolling the film, can be attributed to breaking up agglomerates. The PTFE fibers, seen in FIG. 26B, are all holding onto the particles and preventing agglomeration, which could lead to a decrease in the SSA.

Particle size distribution data for several GNPs is shown in FIG. 7. An effect on particle size and surface area is observed between the as received GNP and nitrogen baked GNP. This decrease in average particle size has increased the specific surface area (SSA), allowing for larger number of sites for adsorption. Table 1 displays surface area data of all materials from nitrogen adsorption experiments, based on BET and QSDFT calculations.

FIGS. 27A-F and FIGS. 28A-F display the cytokine (IL-6, IL-8, and TNF-α) concentration as a function of time and normalized adsorption (mass of cytokine adsorbed per unit mass of adsorbent) for PVA-GNP and PTFE-GNP composites, respectively. Tables 3 through 8 show values obtained from fitting the normalized adsorption data to both an exponential decay function and Ho and McKay's pseudo second-order function. Y. S. Ho and G. McKay, "Pseudo-second order model for sorption processes," PROCESS BIOCHEMISTRY, vol. 34, pp. 451-465, 1999.

The calculated $q_e$ and $q_\infty$ represent the normalized adsorption of cytokine per unit mass of adsorbent at equilibrium, where $q_e$ is calculated from the pseudo second-order model and $q_\infty$ is found from the exponential decay function. Due to the higher $R^2$ values, only $q_e$ values will be considered for analysis.

Overall, the kinetics of adsorption for the loose powder far outweighed the kinetics of the composites. Rapid adsorption was seen in both ARC-500 GNP and the C-500 GNP that was baked and vacuum annealed. Very low adsorption was observed for the PTFE film without GNP, and the cryogel without the GNP saw comparable adsorption capacity to the cryogel with GNP particles. GNP in the PTFE film saw a gradual decrease in all three cytokines.

Figure 28A:
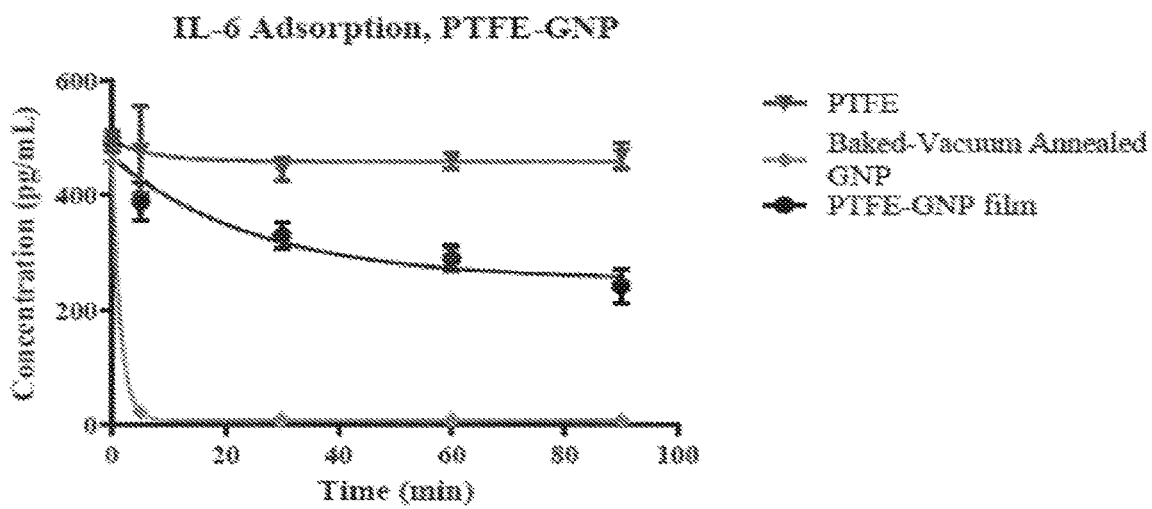
FIGS. 28A-28F show cytokine concentration and normalized adsorption on PTFE-GNP composite and its individual components.
Figure 28B:
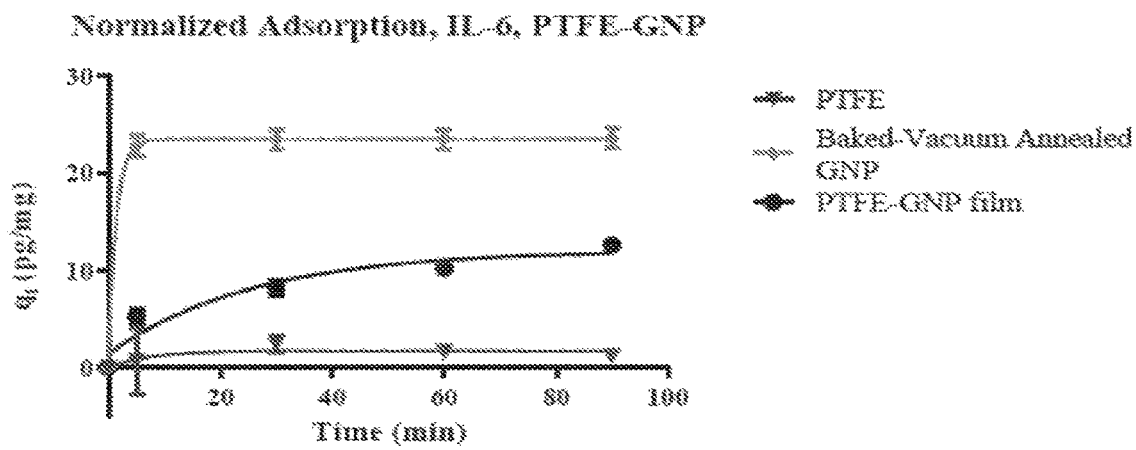
Figure 28C:
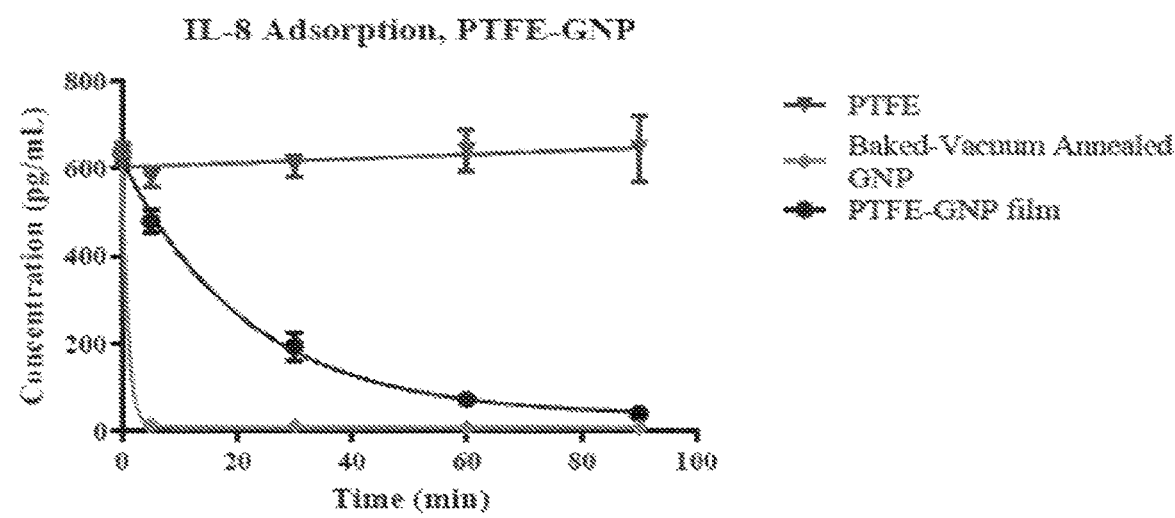
Figure 28D:
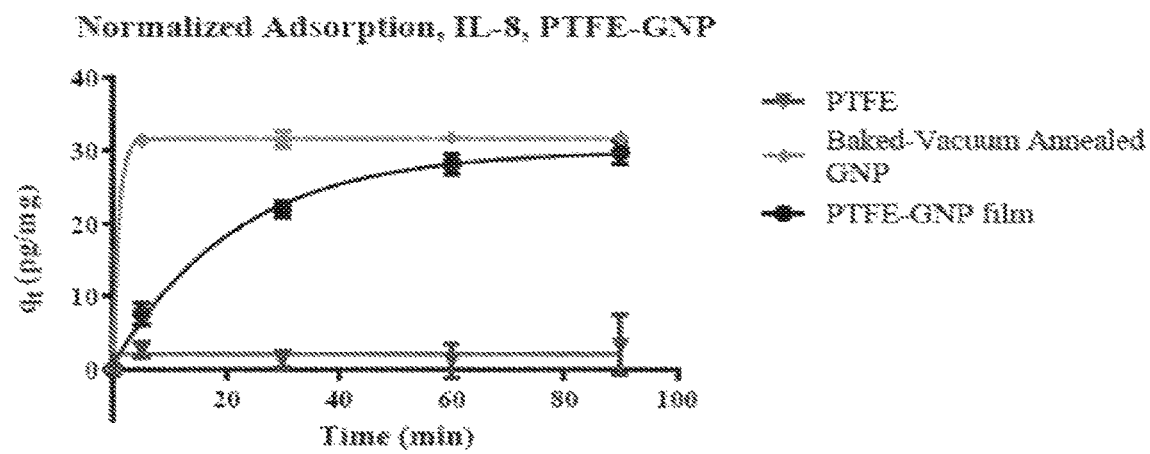
Figure 28E:
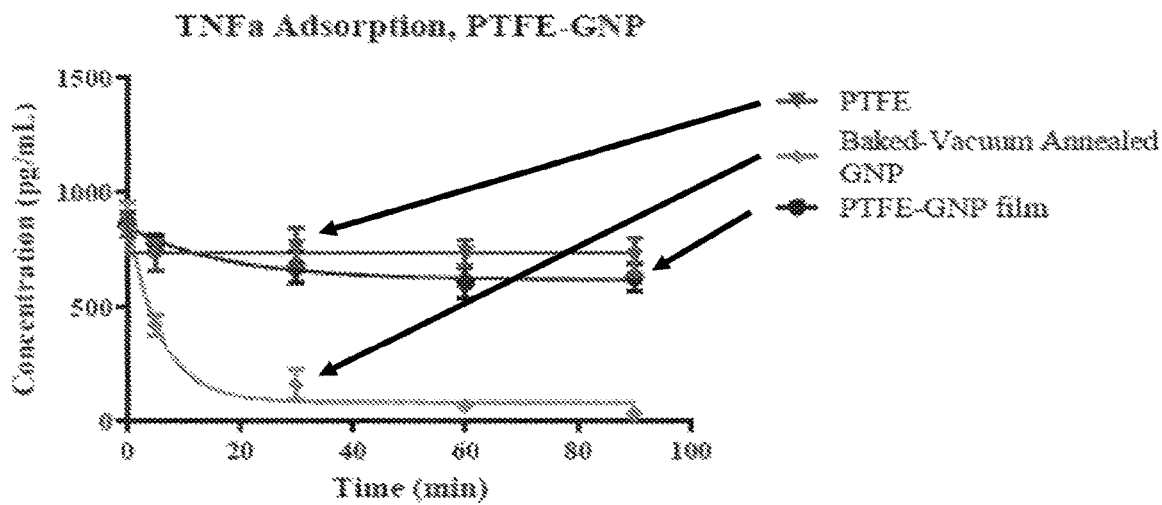
Figures 28F, 29:
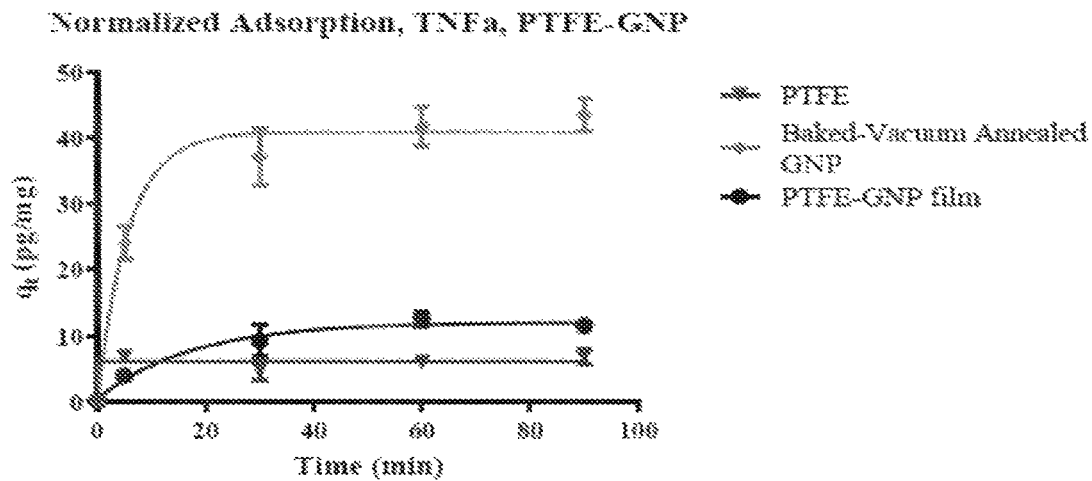
FIG. 29 shows statistical significance of concentration change, based on two-way ANOVA and Tukey multiple comparisons test.

By using a two-way ANOVA with a post-hoc Tukey's multiple comparison test using GraphPad Prism 6 (GraphPad Inc., CA, USA), it was revealed that the positive controls for IL-6, IL-8, and TNF-α (blood plasma with excess cytokines but no adsorbent) did not have statistically significant differences in concentration over the time scale of the experiment. This multiple comparisons test was completed for all of the materials, and its results are seen in FIG. 29. This analysis shows that the composites are reducing concentrations of these three cytokines, and that the particles were contributing to this adsorption.

For the PTFE film without GNP, there was no statistical significance for the interval $p<0.05$ for the adsorption of cytokines onto the PTFE film. After adding GNP and incubating with the material for 1 hour, the difference in concentrations was significant for a p-value ranging from $<0.05$ to $\leq 0.0001$. With 5 minutes of incubation with the PVA cryogel (without GNP), there was no statistical significance from the initial concentration for the interval $p<0.05$. The addition of GNP into the PVA cryogel allowed for a significant decrease in IL-6 concentration after 5 minutes, and even more so after 1 hour ($p\leq 0.01$ to $p\leq 0.0001$). The data indicates that the addition of GNP into the free standing, flexible PTFE film allowed for cytokine adsorption to occur. Other than with IL-6, this trend was not seen with the addition of GNP into the cryogel.

Figure 30A:
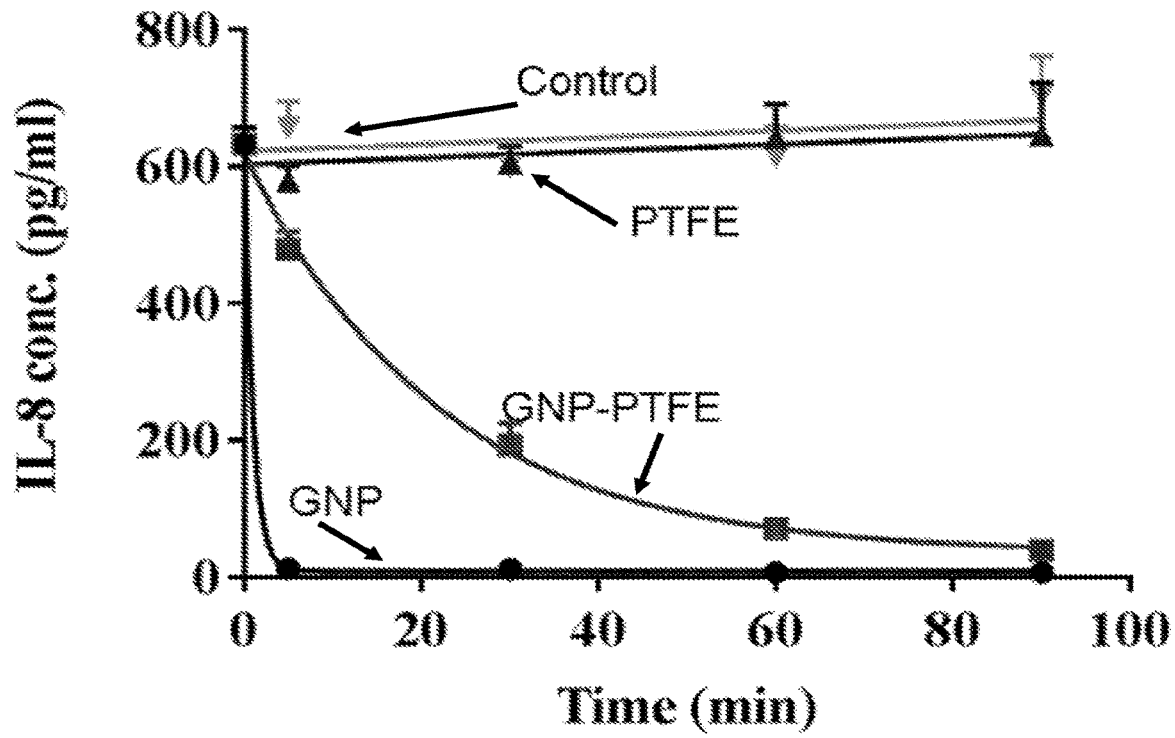
FIGS. 30A-30C shows removal of inflammatory cytokines IL-8 (FIG. 30A), IL-6 (FIG. 30B) and TNF-α (FIG. 30C) from spiked human plasma sample using graphene nanoplatelets (GNP), graphene nanoplatelets with polytetrafluoroethylene composite film (GNP-PTFE) and polytetrafluoroethylene film (PTFE) (±SEM, n=3).
Figure 30B:
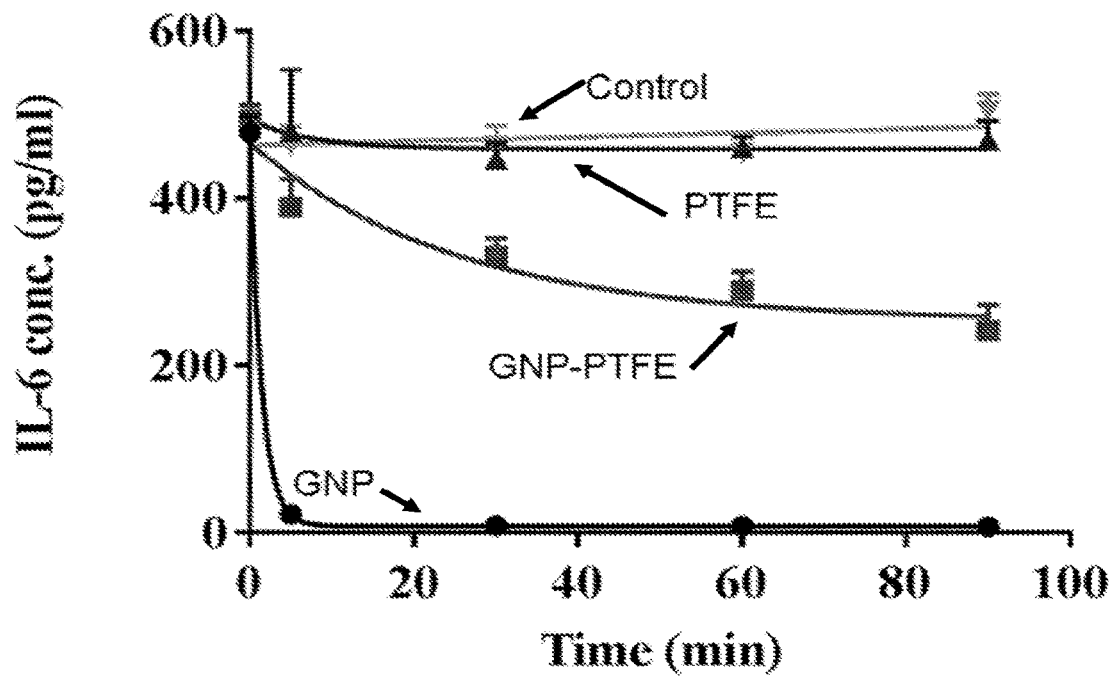
Figure 30C:
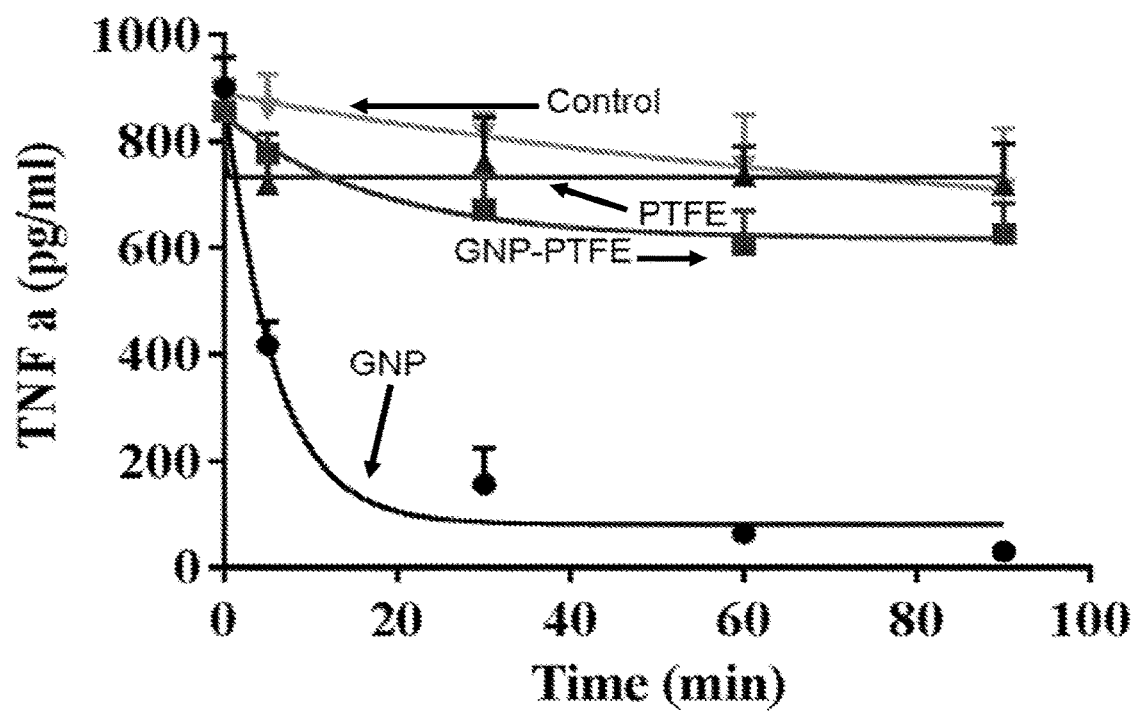
Figure 31A:
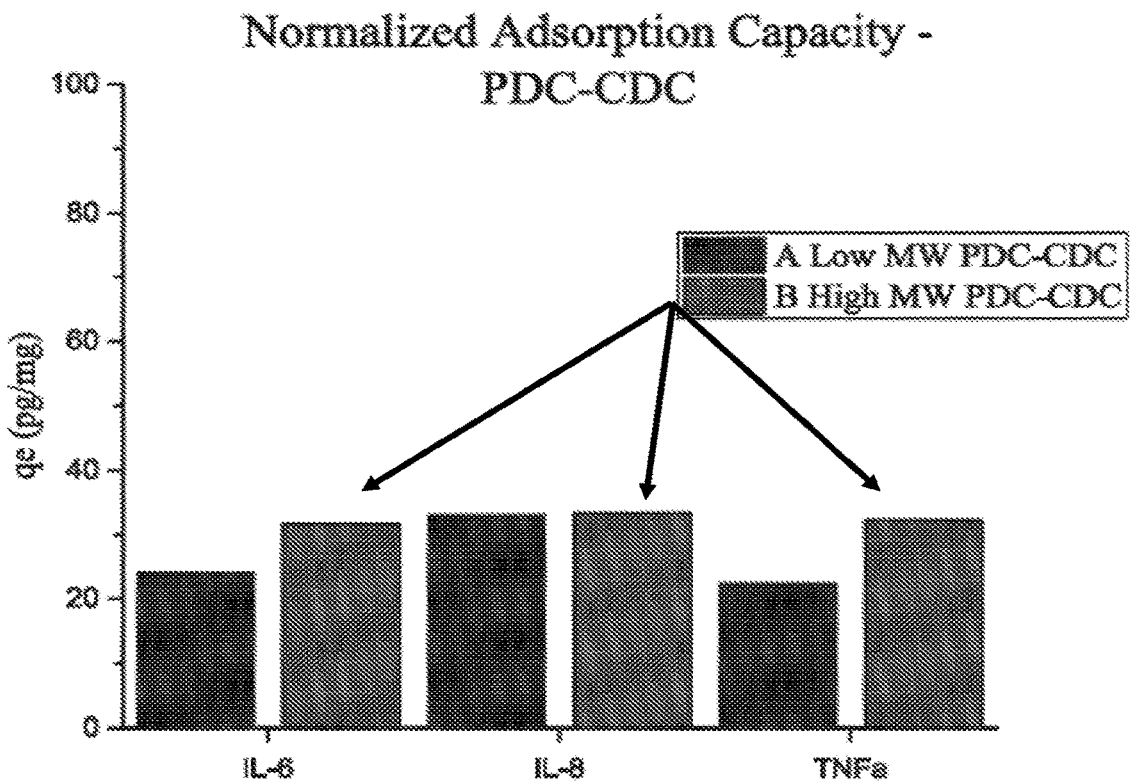
FIGS. 31A-31D show the normalized adsorption capacities for PDC-CDC (FIG. 31A), GNPs of different surface areas (FIG. 31B), surface functionalized GNPs (FIG. 31C), and GNP composites (FIG. 31D).
Figure 31B:
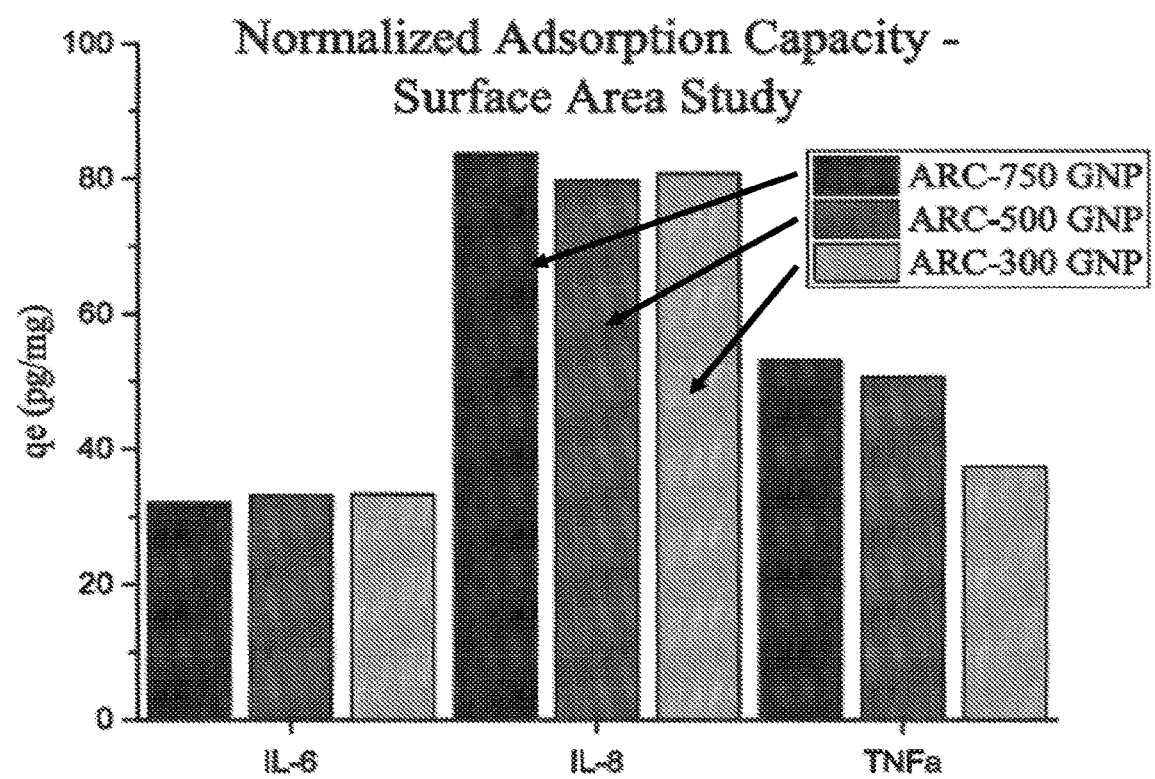
Figure 31C:
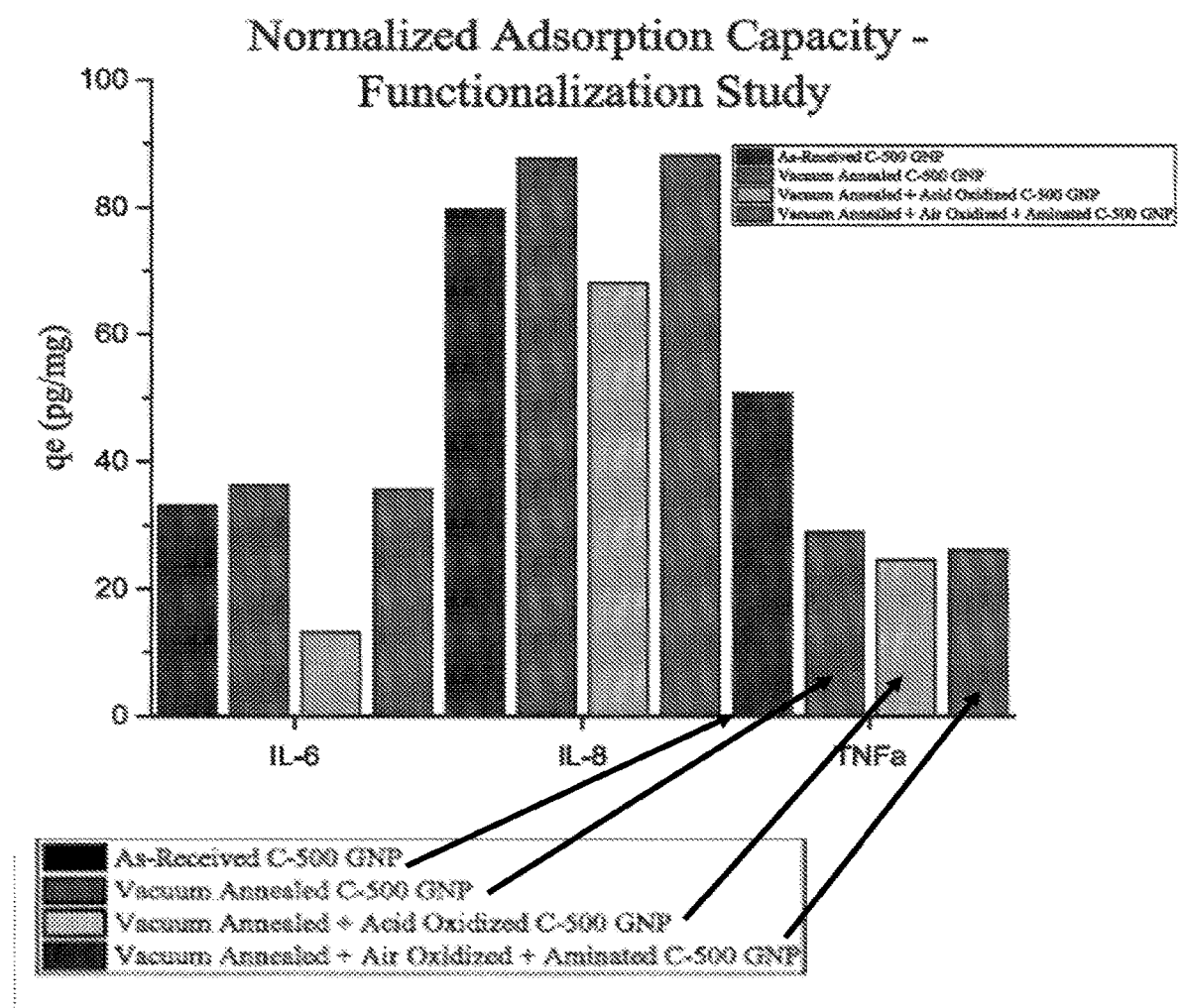
Figure 31D:
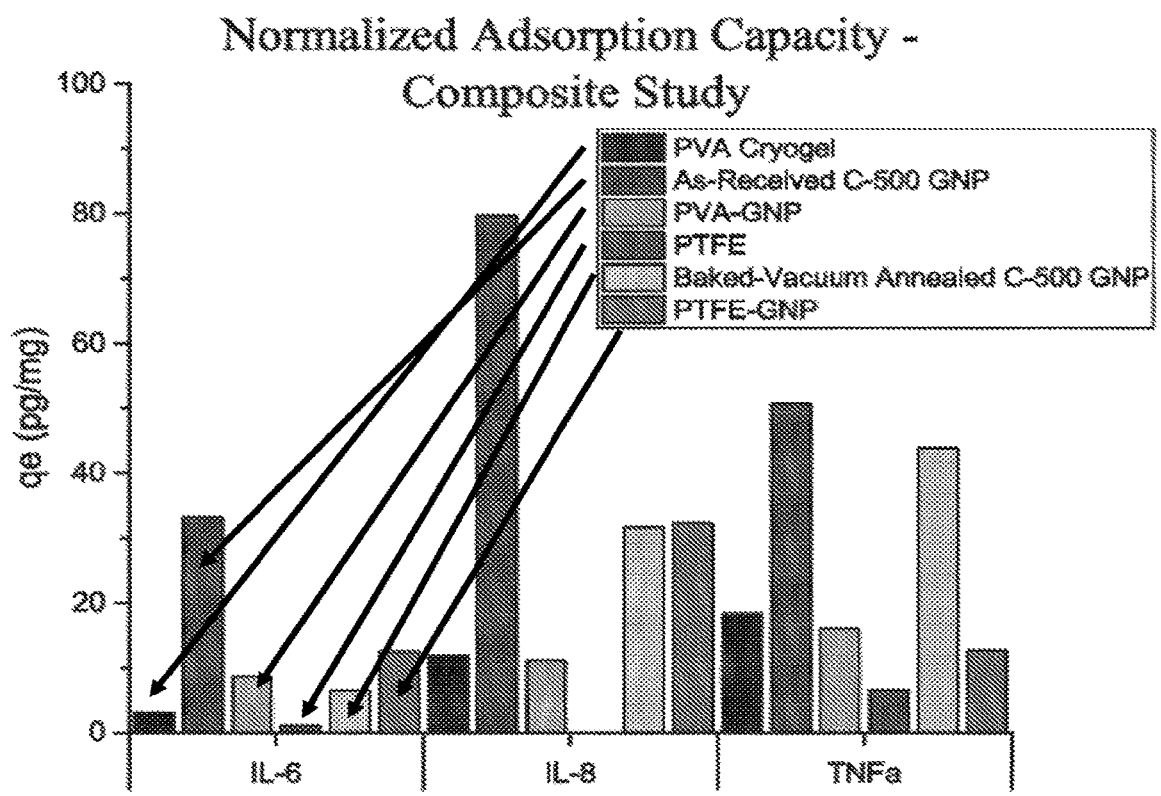
Figure 33A:
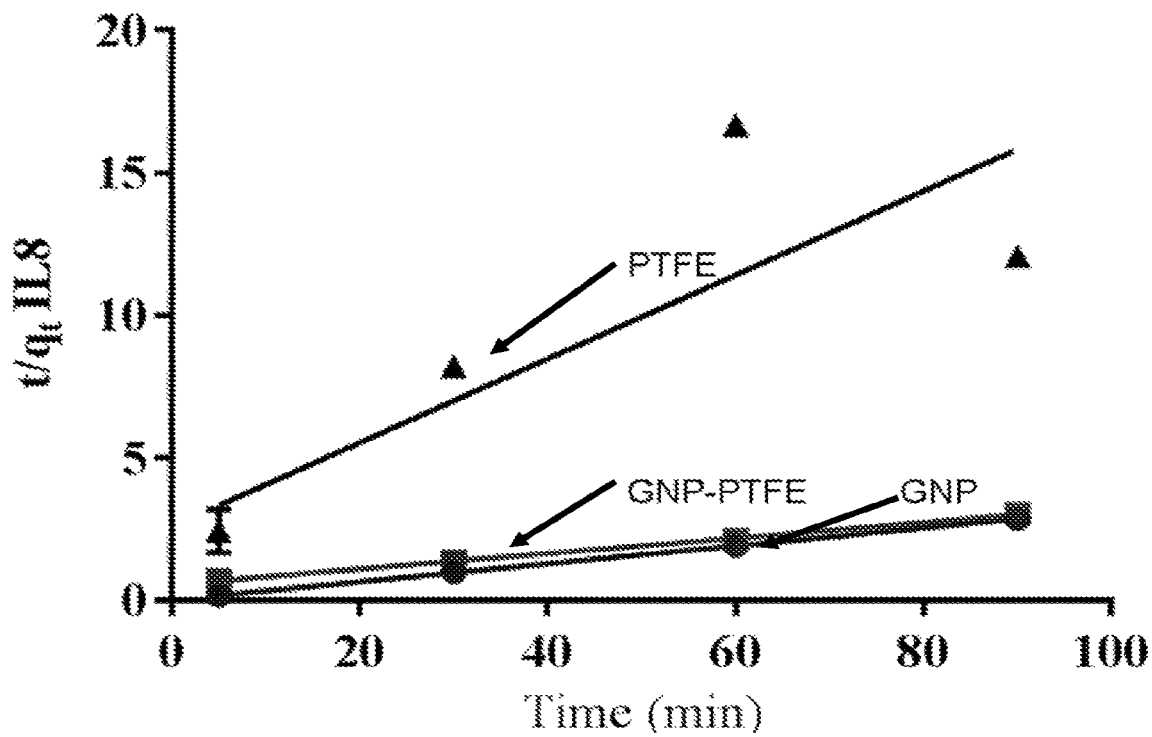
FIGS. 33A-33C show pseudo second order model of cytokines ILS (FIG. 33A), IL6 (FIG. 33B) and TNF-α (FIG. 33C) adsorption kinetic.
Figure 33B:
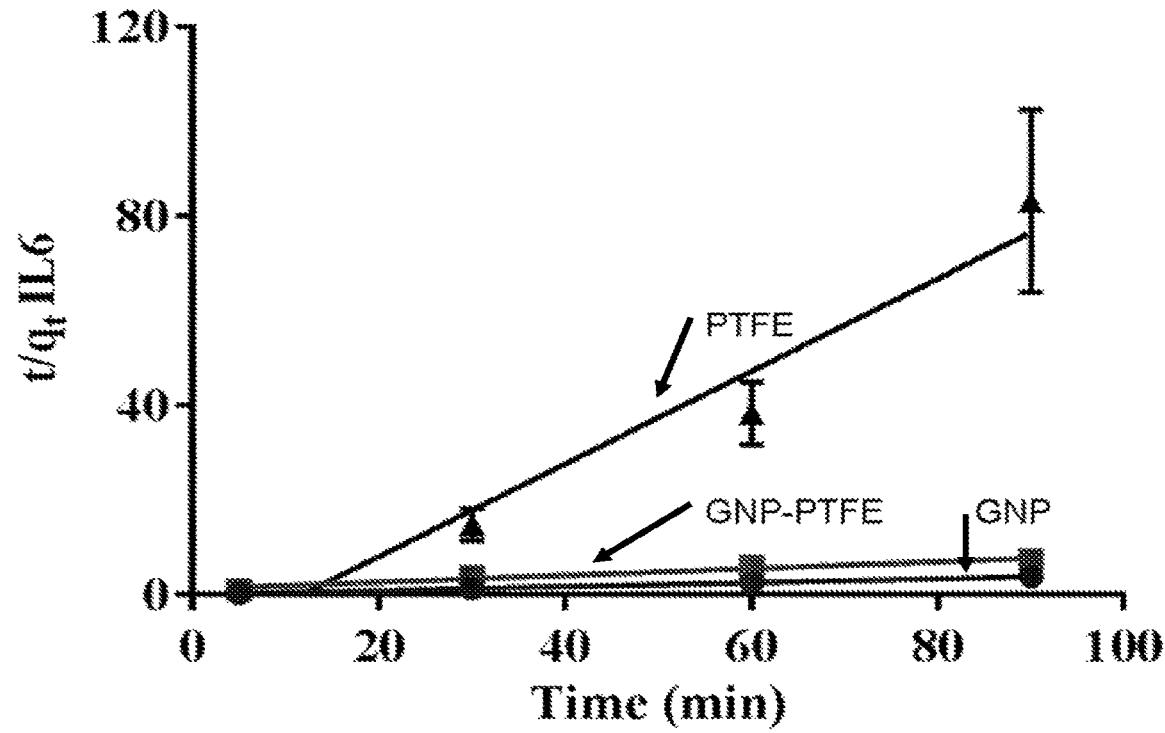
Figure 33C:
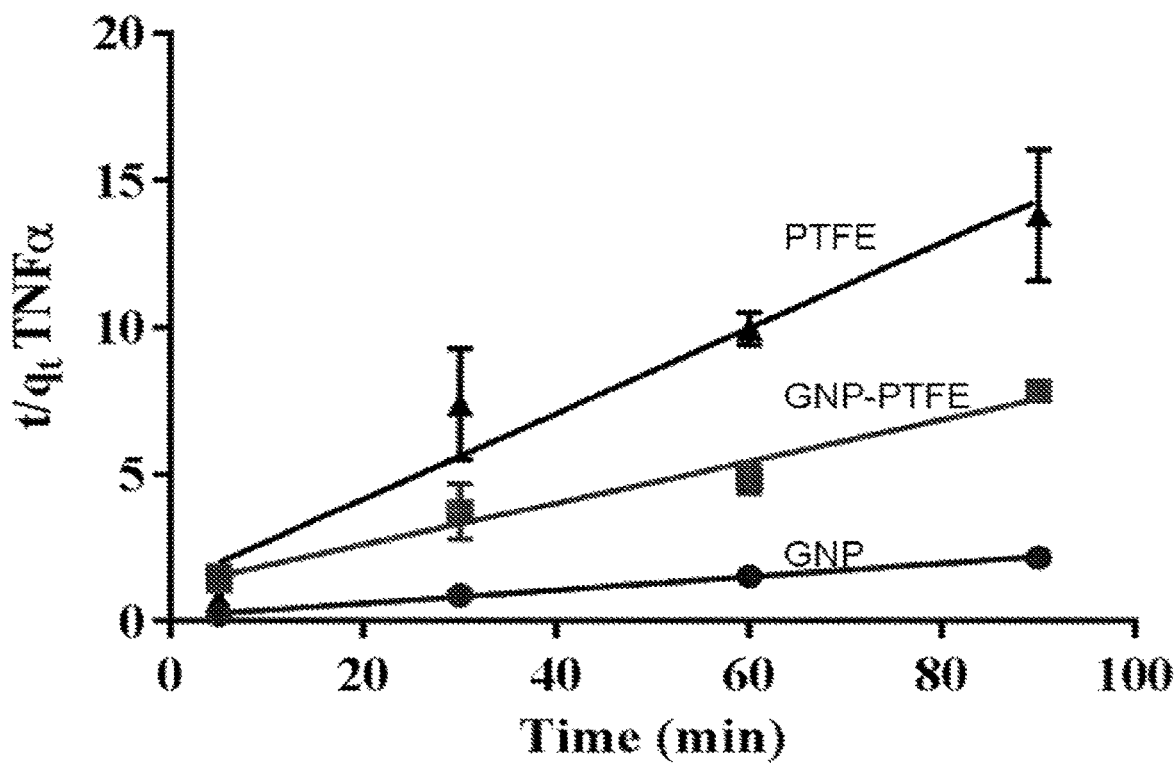
Figure 34A:
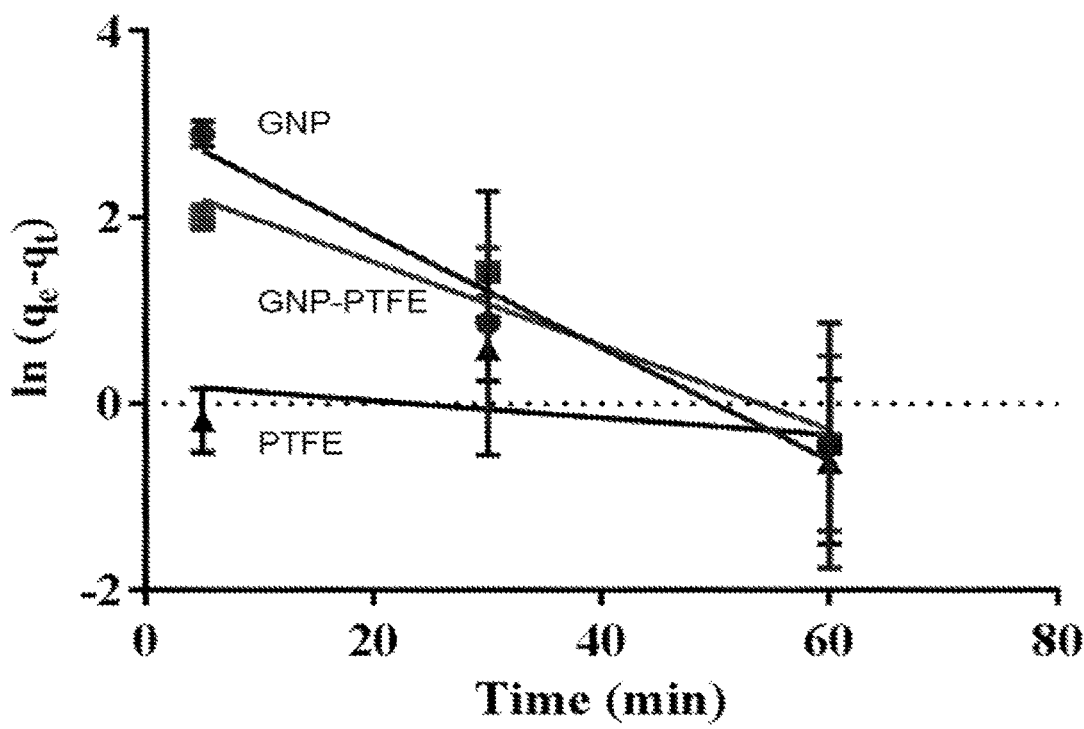
FIGS. 34A-34C show pseudo second order model of cytokines ILS (FIG. 34A), IL6 (FIG. 34B) and TNF-α (FIG. 34C) adsorption kinetic.
Figure 34B:
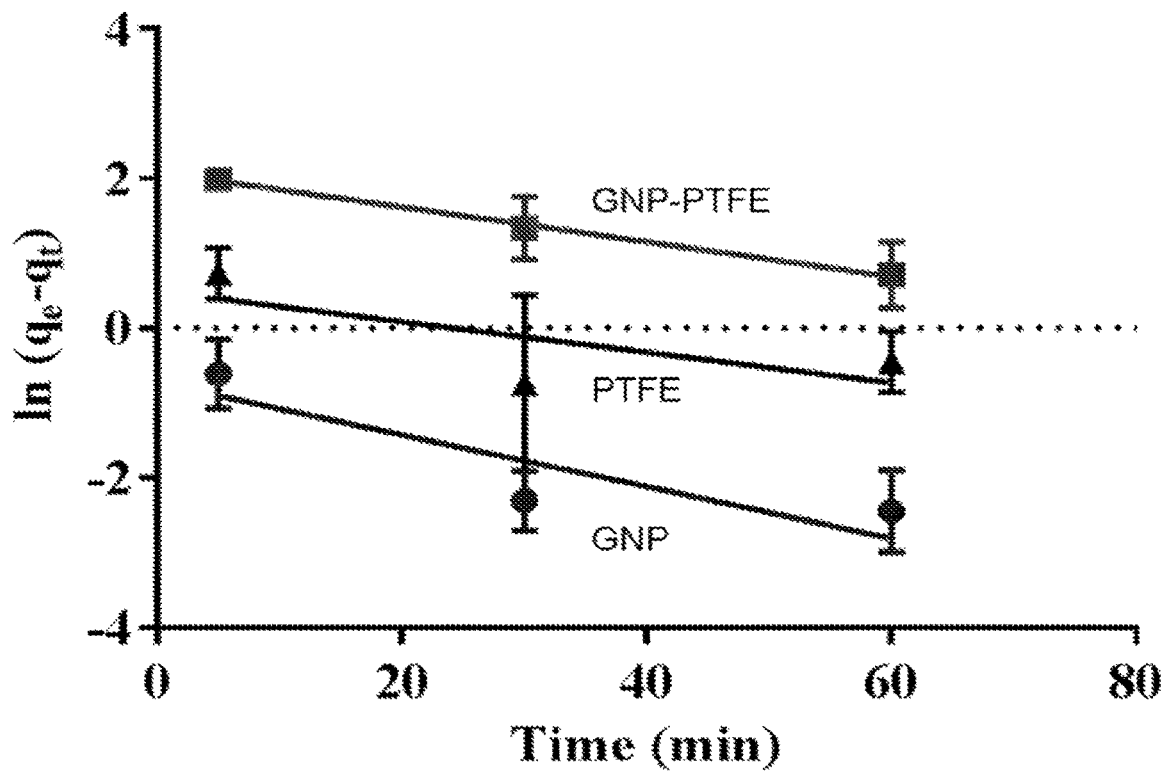
Figure 34C:
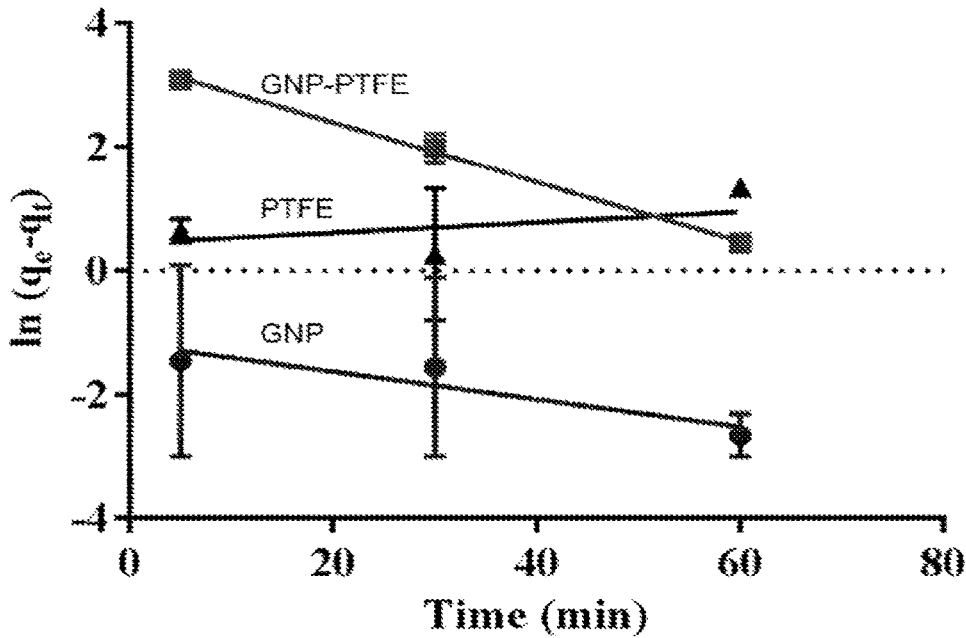

A flexible and free-standing film was prepared from rolling out the GNP-PTFE mixture with ethanol; when ethanol was removed, the PTFE bound GNP particles together into a matrix. The adsorption of cytokine markers IL-8, IL-6 and TNF-α revealed that the PTFE film alone did not reduce the cytokine concentration in the spiked plasma compared to the control within the 90 min of incubation. In contrast, when the spiked plasma was incubated with GNP particles, its IL-8 concentration reduced from 633 µg/ml to 7 µg/ml within 5 mins. IL-6 decreased from 477 µg/ml to 22 µg/ml after 5 mins and further dropped to 8 µg/ml after 30 mins (FIGS. 30A-B). The GNP-PTFE film shows a slower adsorption kinetics of IL-8 from the spiked plasma compared to the GNP, but with 95% removal of IL-8 over 90 min of incubation (FIG. 30A). A significantly lower adsorption efficiency of IL-6 was observed in GNP-PTFE film compared to the GNP particles, but GNP-PTFE film removed over 50% of IL6 from the spiked plasma over the 90 min of incubation period (FIG. 30B). Although incorporating the GNP in PTFE film reduced TNF-α removal compared to the GNP particles (FIG. 30C), the plasma TNF-α level was significantly reduced after 90 minutes of incubation with GNP-PTFE. This could be due to the packing of GNP particles, which reduced the exposed particle outer surface area, or reduced inter-particle accessibility caused by PTFE. Overall, the incorporation of GNP in PTFE film did not significantly reduce the GNP surface available for the adsorption of middle molecular weight cytokine markers IL-6 and IL-8, and demonstrated high adsorption of TNF-α.

TABLE 3

Normalized adsorption of IL-6, one phase exponential decay model

| IL-6 Adsorbent | $R^2$ | k | $q_0$ (pg/mL) | $q^\infty$ (pg/mL) |
|---|---|---|---|---|
| PDC-CDC A Low MW | 0.72 | 0.02 | 1.30 | 12.65 |
| PDC-CDC B High MW | 0.82 | 0.10 | 0.58 | 23.22 |
| ARC-750, 10 mg | 0.92 | 0.94 | 0.00 | 31.98 |
| ARC-500, 10 mg | 0.96 | 1.06 | 0.00 | 32.97 |
| ARC-300, 10 mg | 0.93 | 0.58 | 0.00 | 32.39 |
| ARC-500, 25 mg | 0.94 | 0.99 | 0.00 | 30.90 |
| ARC-500, 50 mg | 0.92 | 0.96 | 0.00 | 30.23 |
| ARC-500, 100 mg | 0.97 | 18.52 | 0.00 | 31.40 |
| ARC-500 Vacuum Annealed | 0.88 | 0.40 | 0.00 | 34.93 |
| ARC-500 Vacuum Annealed, Acid Oxidized | 0.48 | 0.54 | 0.00 | 12.14 |
| ARC-500 Vacuum Annealed, Air Oxidized, Aminated | 0.96 | 0.38 | 0.00 | 34.18 |
| PVA Cryogel | 0.62 | 969.70 | 0.00 | 4.23 |
| PVA-GNP | 0.70 | 0.09 | 0.17 | 8.31 |
| PTFE | 0.09 | 0.14 | −0.05 | 1.73 |
| Baked-Vacuum Annealed GNP | 0.97 | 0.70 | 0.00 | 23.49 |
| PTFE-GNP | 0.88 | 0.04 | 1.37 | 12.04 |

TABLE 4

Normalized adsorption of IL-8, one phase exponential decay model

| IL-8 Adsorbent | $R^2$ | k | $q_0$ (pg/mL) | $q^\infty$ (pg/mL) |
|---|---|---|---|---|
| PDC-CDC A Low MW | 0.90 | 0.07 | 2.51 | 30.37 |
| PDC-CDC B High MW | 0.92 | 0.88 | 0.00 | 33.17 |
| ARC-750, 10 mg | 0.99 | 0.81 | 0.00 | 83.19 |
| ARC-500, 10 mg | 1.00 | 1.31 | 0.00 | 79.29 |
| ARC-300, 10 mg | 1.00 | 1.32 | 0.00 | 80.50 |
| ARC-500, 25 mg | 0.95 | 54962.00 | 0.00 | 87.75 |
| ARC-500, 50 mg | 0.98 | 3.88 | 0.00 | 87.34 |
| ARC-500, 100 mg | 0.93 | 321.60 | 0.00 | 87.10 |
| ARC-500 Vacuum Annealed | 0.98 | 6.55 | 0.00 | 87.72 |
| ARC-500 Vacuum Annealed, Acid Oxidized | 0.62 | 2199.00 | 0.00 | 67.31 |
| ARC-500 Vacuum Annealed, Air Oxidized, Aminated | 0.97 | 0.65 | 0.00 | 88.48 |
| PVA Cryogel | 0.80 | 1195000 | 0.00 | 16.27 |
| PVA-GNP | 0.68 | 0.04 | 0.72 | 11.55 |
| PTFE | 0.14 | 1496000 | 0.00 | 2.14 |
| Baked-Vacuum Annealed GNP | 0.99 | 1.02 | 0.00 | 31.58 |
| PTFE-GNP | 0.98 | 0.05 | 0.65 | 29.94 |

TABLE 5

Normalized adsorption of TNF-α, one phase exponential decay model

| TNF-a Adsorbent | $R^2$ | k | $q_0$ (pg/mL) | $q^\infty$ (pg/mL) |
|---|---|---|---|---|
| PDC-CDC A Low MW |  | 0.00 | 1.68 | 78650 |
| PDC-CDC B High MW | 0.40 | 0.16 | −0.01 | 5.41 |
| ARC-750, 10 mg | 0.94 | 0.34 | 0.03 | 48.54 |
| ARC-500, 10 mg | 0.71 | 0.39 | −0.01 | 48.81 |
| ARC-300, 10 mg | 0.77 | 0.49 | 0.00 | 32.66 |
| ARC-500, 25 mg | 0.77 | 0.45 | 0.00 | 75.79 |
| ARC-500, 50 mg | 0.57 | 0.58 | 0.00 | 89.37 |
| ARC-500, 100 mg | 0.70 | 0.69 | 0.00 | 85.04 |
| ARC-500 Vacuum Annealed | 0.84 | 0.84 | 0.00 | 24.77 |
| ARC-500 Vacuum Annealed, Acid Oxidized | 0.70 | 0.51 | 0.00 | 25.08 |
| ARC-500 Vacuum Annealed, Air Oxidized, Aminated | 0.50 | 0.47 | −0.01 | 26.01 |
| PVA Cryogel | 0.90 | 0.16 | −0.06 | 18.93 |
| PVA-GNP | 0.63 | 0.21 | 0.01 | 16.35 |
| PTFE | 0.73 | 14.37 | 0.00 | 6.16 |
| Baked-Vacuum Annealed GNP | 0.90 | 0.17 | 0.10 | 40.97 |
| PTFE-GNP | 0.86 | 0.06 | 0.39 | 12.06 |

TABLE 6

Normalized adsorption of IL-6, Ho and McKay's pseudo second-order model

| IL-6 Adsorbent | k | $R^2$ | $q_e$ (pg/mg) |
|---|---|---|---|
| PDC-CDC A Low MW | 0.0004 | 0.99 | 24.06 |
| PDC-CDC B High MW | 0.0018 | 1.00 | 31.68 |
| ARC-750, 10 mg | 0.47 | 1.00 | 32.05 |
| ARC-500, 10 mg | 0.24 | 1.00 | 33.13 |
| ARC-300, 10 mg | 0.05 | 1.00 | 33.29 |
| ARC-500, 25 mg | −1.27 | 1.00 | 30.87 |
| ARC-500, 50 mg | −0.51 | 1.00 | 30.15 |
| ARC-500, 100 mg | −0.44 | 1.00 | 31.22 |
| ARC-500 Vacuum Annealed | 0.02 | 1.00 | 36.33 |
| ARC-500 Vacuum Annealed, Acid Oxidized | −0.02 | 0.96 | 13.19 |
| ARC-500 Vacuum Annealed, Air Oxidized, Aminated | 0.02 | 1.00 | 35.64 |
| PVA Cryogel | −0.09 | 0.98 | 3.00 |
| PVA-GNP | 0.01 | 0.86 | 8.70 |
| PTFE | −0.14 | 0.95 | 1.12 |
| Baked-Vacuum Annealed GNP | 0.00 | 0.32 | 6.46 |
| PTFE-GNP | 0.01 | 0.96 | 12.58 |

TABLE 7

Normalized adsorption of IL-8, Ho and McKay's pseudo second-order model

| IL-8 Adsorbent | k | $R^2$ | $q_e$ (pg/mg) |
|---|---|---|---|
| PDC-CDC A Low MW | 0.00451 | 1.00 | 32.97 |
| PDC-CDC B High MW | 0.24 | 1.00 | 33.32 |
| ARC-750, 10 mg | 0.12 | 1.00 | 83.71 |
| ARC-500, 10 mg | 0.22 | 1.00 | 79.64 |
| ARC-300, 10 mg | 0.17 | 1.00 | 80.77 |
| ARC-500, 25 mg | 0.34 | 1.00 | 87.90 |
| ARC-500, 50 mg | 1.17 | 1.00 | 87.32 |
| ARC-500, 100 mg | 0.18 | 1.00 | 87.42 |
| ARC-500 Vacuum Annealed | −0.78 | 1.00 | 87.62 |
| ARC-500 Vacuum Annealed, Acid Oxidized | 0.06 | 1.00 | 68.11 |
| ARC-500 Vacuum Annealed, Air Oxidized, Aminated | −0.35 | 1.00 | 88.15 |
| PVA Cryogel | −0.02 | 0.96 | 11.95 |
| PVA-GNP | 0.01 | 0.96 | 11.14 |
| PTFE | 0.03 | 0.64 |  |
| Baked-Vacuum Annealed GNP | 0.38 | 1.00 | 31.60 |
| PTFE-GNP | 0.00 | 0.97 | 32.32 |

TABLE 8

Normalized adsorption of TNF-α, Ho and McKay's pseudo second-order model

| TNF-α Adsorbent | k | $R^2$ | $q_e$ (pg/mg) |
|---|---|---|---|
| PDC-CDC A Low MW | 0.00033 | 0.97 | 22.27 |
| PDC-CDC B High MW | 0.00015 | 0.90 | 32.31 |
| ARC-750, 10 mg | 0.01 | 1.00 | 53.17 |
| ARC-500, 10 mg | 0.02 | 1.00 | 50.70 |
| ARC-300, 10 mg | 0.01 | 1.00 | 37.36 |
| ARC-500, 25 mg | 0.02 | 1.00 | 78.19 |
| ARC-500, 50 mg | 0.03 | 1.00 | 90.75 |
| ARC-500, 100 mg | 0.02 | 1.00 | 87.16 |
| ARC-500 Vacuum Annealed | 0.01 | 0.99 | 28.93 |
| ARC-500 Vacuum Annealed, Acid Oxidized | −0.01 | 0.95 | 24.59 |
| ARC-500 Vacuum Annealed, Air Oxidized, Aminated | 0.02 | 0.97 | 26.13 |
| PVA Cryogel | 0.03 | 0.99 | 18.39 |
| PVA-GNP | 0.02 | 0.98 | 16.07 |
| PTFE | 0.03 | 0.96 | 6.52 |
| Baked-Vacuum Annealed GNP | 0.01 | 1.00 | 43.92 |
| PTFE-GNP | 0.01 | 0.96 | 12.73 |

Table 9 Lagergren first order kinetic for adsorption of cytokine markers by GNP and GNP-PTFE composite. By plotting the natural log of the difference between equilibrium cytokine adsorption and adsorption at each time point ($\ln(q_e-q_t)$) against the incubation time, the pseudo-first-order model yields a linear regression equation with the slope equal to the pseudo-first-order adsorption kinetic constant ($K_{p1}$) and the intercept representing the natural log of equilibrium adsorption capacity ($q_{e1}$).

TABLE 9

| | IL8 | | | IL6 | | | TNFα | | |
|---|---|---|---|---|---|---|---|---|---|
| | $R^2$ | $K_1$ | $q_{e1}$ | $R^2$ | $K_1$ | $q_{e1}$ | $R^2$ | $K_1$ | $q_{e1}$ |
| GNP | 0.1374 | 0.0223 | 0.31 | 0.5111 | 0.0348 | 0.48 | 0.4190 | 0.0604 | 20.51 |
| GNP-PTFE | 0.9609 | 0.0481 | 28.93 | 0.5208 | 0.0232 | 8.00 | 0.5915 | 0.0448 | 11.23 |
| PTFE | 0.0530 | −0.0084 | 1.56 | 0.1385 | 0.0204 | 1.64 | 0.0456 | 0.0091 | 1.24 |

Table 10 Pseudo second order kinetic for adsorption of cytokine markers by GNP and GNP-PTFE composite by plotting the time divided by the cytokine adsorption at each time point ($t/q_t$) against the incubation time (t), the pseudo-second-order model yields a linear regression equation. The equilibrium adsorption capacity ($q_e$) can be calculated by $$\frac{1}{\text{slope}},$$

and the pseudo-second-order adsorption kinetic constant ($K_{p2}$) can be calculated by $$\frac{1}{\text{intercept} \times q_{e2}}.$$

TABLE 10

| | IL8 | | | IL6 | | | TNFα | | |
|---|---|---|---|---|---|---|---|---|---|
| | $R^2$ | $K_2$ | $q_{e2}$ | $R^2$ | $K_2$ | $q_{e2}$ | $R^2$ | $K_2$ | $q_{e2}$ |
| GNP | 0.9895 | 0.1663 | 31.37 | 0.9913 | 0.2594 | 24.32 | 0.9445 | 0.0033 | 44.3 |
| GNP-PTFE | 0.9626 | 0.0014 | 36.45 | 0.9300 | 0.0047 | 13.83 | 0.8527 | 0.0042 | 14.1 |
| PTFE | 0.7362 | 0.0083 | 6.804 | 0.7621 | −0.0827 | 1.022 | 0.7904 | 0.0168 | 6.9 |

Ho and McKay's pseudo second order model defines the variable $q_e$, which is the normalized adsorption capacity for an adsorbent, in units of mass of cytokine per unit mass of adsorbent. This variable was compared across all materials to identify the most efficient adsorbent. To test the capability of the adsorbent for rapid adsorption in its actual application, a simple calculation was completed. Using the pseudo second-order $q_e$, the mass of adsorbent needed to completely remove the concentration of IL-6, IL-8, and TNF-α from the blood after 5 minutes was found. Based on the average cost of GNP production according to the XG Sciences, the cost of the material needed was also obtained.

FIGS. 31A-31D display the normalized adsorption capacity for the materials tested. Only the average values for each triplicate per cytokine are displayed in the graphs. From this information, the most efficient adsorbent for a given cytokine was determined and its efficacy was compared against other materials. The best performing adsorbent for IL-6 was vacuum annealed C-500 GNP, with a normalized adsorption capacity of 36 µg/mg (picograms of cytokine per milligram of adsorbent). For IL-8, the vacuum annealed, air oxidized, and aminated C-500 had the highest capacity, with 88 µg/mg adsorbed. TNF-α was adsorbed by ARC-750 at a capacity of 53 µg/mg.

Assuming a total blood volume of a patient is about 6.3 liters (based on the average weight of an adult in North America (80.7 kg (S. C. Walpole, D. Prieto-Merino, P. Edwards, J. Cleland, G. Stevens, and I. Roberts, "The weight of nations: an estimation of adult human biomass," *BMC PUBLIC HEALTH*, vol. 12, pp. 439-439, 2012.)) and blood volume per unit mass being 78 ml/kg (N/A, "2.5.1 Estimated Blood Volumes," in *Protection in Nuclear Medicine and Ultrasound Diagnostic Procedures in Children*: (Report No. 73), ed: National Council on Radiation Protection and Measurements (NCRP).)), and a cytokine concentration of 1000 µg/mL, a person with sepsis requires 6.3 µg of each cytokine to be removed from the blood. Based on the normalized adsorption data after 5 minutes, the mass of adsorbent can be calculated based on the mass of cytokine to be adsorbed. FIG. 32 displays these calculations for the three cytokines, with the smallest mass to adsorb these protein levels in 5 minutes is from ARC-500 GNP at 422 grams. XG Sciences states that their manufacturing process can produce GNP at a cost of $40 per kilogram, so the cost per patient for the adsorbent would be $17. This small amount is very large improvement from hemodialysis and hemoperfusion treatments that use intensive care resources for hours and sometimes days at a time. Since the treatment of blood is extracorporeal, one can create one large hemoperfusion cartridge for an extremely short treatment.

As those skilled in the art will appreciate, numerous modifications and variations of the present invention are possible in light of these teachings, and all such are contemplated hereby. The disclosures of each patent, patent application, and publication cited or described in this document, are hereby incorporated herein by reference, each in its entirety, for all purposes.

What is claimed:

1. A method of removing proteins or peptides from blood or a blood product, the method comprising contacting the blood or blood product with a carbon form having slit-shaped mesopores and macropores, the pore size dimensions chosen to be comparable to the size of the proteins or peptides, wherein the carbon form comprises graphene nanoplatelets (GNPs) or polymer-derived ceramic carbide-derived carbon (PDC-CDC), and wherein the contacting results in the removal of at least 80% of the protein or the peptide from the blood or blood product in less than 120 minutes.

2. The method of claim 1, wherein the carbon form comprises graphene nanoplatelets (GNPs).

3. The method of claim 1, wherein the carbon form comprises polymer-derived ceramic carbide-derived carbon (PDC-CDC).

4. The method of claim 1, wherein the protein or the peptide has a molecular weight in a range of from 5 to 60 kDa.

5. The method of claim 1, wherein the protein/peptide is a cytokine.

6. The method of claim 5, wherein the cytokine is a chemokine, interferon, interleukin, lymphokine, or tumour necrosis factor.

7. The method of claim 1, wherein the protein is IL-6, IL-8, or TNF-α, lymphotoxin-α (aka TNF-β).

8. The method of claim 1, wherein at least 80% of the protein or the peptide is removed from the blood or blood product in less than 60 minutes.

9. The method of claim 1, wherein the carbon form is dispersed within a polymer composite.

10. The method of claim 2 wherein the GNPs are vacuum-annealed C-500 GNPs.

11. The method of claim 10 wherein the C-500 GNPs have been vacuum-annealed, air oxidized, and aminated.

12. The method of claim 2, wherein the GNPs comprise ARC-750.

13. The method of claim 1, wherein the protein is or comprises IL-6.

14. The method of claim 1, wherein the protein is or comprises IL-8.

15. The method of claim 1, wherein the protein is or comprises TNF-α.

16. A method of treating sepsis in a patient in need thereof, comprising performing the method of claim 1 to the blood of the patient.

17. The method of claim 16, wherein the blood or blood products are processed through a hemoperfusion cartridge.

\* \* \* \* \*